United States Patent
Bull et al.

(10) Patent No.: US 6,376,490 B1
(45) Date of Patent: Apr. 23, 2002

(54) QUINOXALINEDIONES

(75) Inventors: David John Bull; Christopher Lee Carr; Michael Jonathan Fray; Elisabeth Colette Louise Gautier; Charles Eric Mowbray; Alan Stobie, all of Sandwich (GB)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 09/157,806

(22) Filed: Sep. 4, 1998

Related U.S. Application Data

(63) Continuation of application No. PCT/EP97/00995, filed on Feb. 27, 1997.

(51) Int. Cl.[7] .................. A61K 31/5377; A61K 31/498; C07D 401/14; C07D 403/04; C07D 403/14
(52) U.S. Cl. .................... 514/234.8; 514/249; 544/116; 544/238; 544/295; 544/354
(58) Field of Search ................. 544/354, 116, 544/238, 295; 514/249, 234.8

(56) References Cited

U.S. PATENT DOCUMENTS

| | | | |
|---|---|---|---|
| 5,283,244 A | 2/1994 | Sakamoto et al. | 514/249 |
| 6,143,733 A | * 11/2000 | Huth et al. | 514/85 |

FOREIGN PATENT DOCUMENTS

| | | | |
|---|---|---|---|
| EP | 0556393 | | 8/1993 |
| EP | 572852 | | 12/1993 |
| JP | 22811294 | | 8/1994 |
| JP | 32408495 | | 12/1995 |
| WO | 9608485 | | 3/1996 |
| WO | 98/38186 | * | 9/1998 |

OTHER PUBLICATIONS

Lipton, *TINS*, vol. 16, p. 527–532, 1993.*
McBurney, *Neurobiology of Aging*, vol. 15, pp. 271–273, 1994.*

* cited by examiner

*Primary Examiner*—Emily Bernhardt
(74) *Attorney, Agent, or Firm*—Peter C. Richardson; Paul H. Ginsburg; A. David Joran

(57) ABSTRACT

The invention provides compounds of the formula (I)

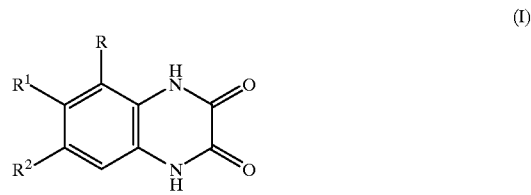

(I)

or a pharmaceutically acceptable salt thereof, wherein R is a 5-membered ring heteroaryl group containing 3 or 4 nitrogen heteroatoms which is linked to the quinoxalinedione ring by a ring carbon or nitrogen atom said group being optionally benzo-fused and optionally substituted, including in the benzo-fused portion, by 1 or 2 substituents each independently selected from $C_1$–$C_4$ alkyl, $C_2$–$C_4$ alkenyl, $C_3$–$C_7$ cycloalkyl, halo, hydroxy, $C_1$–$C_4$ alkoxy, $C_3$–$C_7$ cycloalkyloxy, —COOH, $C_1$–$C_4$ alkoxycarbonyl, —CONR$^3$R$^4$, —NR$^3$R$^4$, —S(O)$_p$($C_1$–$C_4$ alkyl), —SO$_2$NR$^3$R$^4$, aryl, aryloxy, aryl($C_1$–$C_4$)alkoxy, and het, said $C_1$–$C_4$alkyl being optionally substituted by $C_3$–$C_7$ cycloalkyl, halo, hydroxy, $C_1$–$C_4$ alkoxy, halo($C_1C_4$)alkoxy, $C_3$–$C_7$ cycloalkyloxy, $C_3$–$C_7$ cycloalkyl ($C_1$–$C_4$) alkoxy, —COOH, $C_1$–$C_4$ alkoxycarbonyl, —CONR$^3$R$^4$, —NR$^3$R$^4$,—S(O)$_p$($C^1$–$C_4$ alkyl), —SO$_2$(aryl), —SO$_2$NR$^3$R$^4$ morpholino, aryl, aryloxy, aryl($C_1$–$C_4$)alkoxy or het, and said $C_2$–$C_4$ alkenyl being optionally substituted by aryl; and $R^1$ and $R^2$ are each independently selected from H, fluoro, chloro, bromo, $C_1$–$C_4$ alkyl and halo($C_1$–$C_4$)alkyl. The compounds are useful as NDMA receptor antagonists for treating acute neurodegenerative and chronic neurological disorders.

16 Claims, No Drawings

QUINOXALINEDIONES

This Application is a continuation under 35 U.S.C. § 120 of PCT Application No. PCT/EP97/00995 filed Feb. 27, 1997, which, in turn, was based on U.K. Application No. 9605027.3 filed Mar. 9. 1996.

This invention relates to 2,3(1H,4H)-quinoxalinedione derivatives which are selective antagonists of N-methyl-D-aspartate receptors. More particularly, this invention relates to 5-heteroaryl-2,3(1H,4H)-quinoxalinedione derivatives and to the preparation of, compositions containing, the uses of and the intermediates used in the synthesis of, such derivatives.

L-Glutamic acid is an excitatory amino acid neurotransmitter whose physiological role in the brain involves interaction with four receptors, three of which are named after the selective agonists NMDA (N-methyl-D-aspartate), AMPA (2-amino-3-hydroxy-5-methyl-4-isoxazolepropionic acid) and kainate. The fourth receptor is termed the metabotropic receptor. In addition to a binding site for glutamic acid, the NMDA receptor possesses high affinity binding sites for dissociative anaesthetics (e.g. ketamine), polyamines (e.g. spermine), glycine and certain metal ions (e.g. $Mg^{2+}, Zn^{2+}$). Since the NMDA receptor has an absolute requirement to bind glycine for activation to occur, glycine antagonists can act as functional NMDA antagonists.

In the region of a cerebral infarct, anoxia, for example, causes abnormally high concentrations of glutamic acid to be released. This leads to an over-stimulation of NMDA receptors resulting in the degeneration and death of neurones. Thus, NMDA receptor antagonists, which have been shown to block the neurotoxic effects of glutamic acid in vitro and in vivo, may be useful in the treatment and/or prevention of any pathological condition in which NMDA receptor activation is thought to be important. Examples of such conditions include acute neurodegenerative disorders arising from events such as stroke, transient ischaemic attack, peri-operative ischaemia, global ischaemia (following cardiac arrest) and traumatic head injury to the brain or spinal cord. In addition, NMDA antagonists may be of use in treating certain chronic neurological disorders such as senile dementia, Parkinson's disease and Alzheimer's disease. They may also have utility in conditions in which peripheral nerve function has been impaired such as retinal and macular degeneration.

Furthermore, NMDA antagonists have been shown to possess anti-convulsant and anxiolytic activity and may therefore be used to treat epilepsy and anxiety. NMDA antagonists may also attenuate the effects of alcohol withdrawal from physically dependent animals (K.A. Grant et al., J Pharm.Exp.Ther., 260, 1017 (1992)) and thus NMDA antagonists may be of use in the treatment of alcohol addiction and pain. NMDA antagonists may also be useful in the treatment of hearing disorders (e.g. tinnitus), migraine and psychiatric disorders.

EP-A-0572852 describes pyrrol-1-yl-substituted 2,3(1H,4H)-quinoxalinedione derivatives useful for the treatment of neurodegenerative illnesses and neurotoxic disorders of the central nervous system.

EP-A-0556393 disclosed, inter alia, imidazolyl- or triazolyl-substituted 2,3(1H,4H)-quinoxalinedione derivatives with glutamate receptor antagonising activity, particularly NMDA-glycine receptor and AMPA receptor antagonising activities. However, no 5-triazolyl-substituted compounds are specifically described therein.

The present compounds are potent antagonists of the NMDA (glycine site) receptor. In addition, they are highly selective antagonists for the NMDA (glycine site) receptor in comparison to the AMPA receptor to which they have little, if any, affinity.

The present invention relates to a compound of the formula:

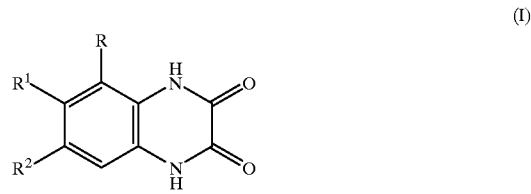

(I)

or a pharmaceutically acceptable salt thereof, wherein

R is a 5-membered ring heteroaryl group containing 3 or 4 nitrogen heteroatoms which is linked to the quinoxalinedione ring by a ring carbon or nitrogen atom, or is a 6-membered ring heteroaryl group containing from 1 to 3 nitrogen heteroatoms which is linked to the quinoxalinedione ring by a ring carbon atom, either of said groups being optionally benzo-fused and optionally substituted, including in the benzo-fused portion, by 1 or 2 substituents each independently selected from $C_1-C_4$ alkyl, $C_2-C_4$ alkenyl, $C_3-C_7$ cycloalkyl, halo, hydroxy, $C_1-C_4$ alkoxy, $C_3-C_7$ cycloalkyloxy, —COOH, $C_1-C_4$ alkoxycarbonyl, —CONR³R⁴, —NR³R⁴, —S(O)$_p$($C_1-C_4$ alkyl), —SO₂NR³R⁴, aryl, aryloxy, aryl($C_1-C_4$)alkoxy and het, said $C_1-C_4$ alkyl being optionally substituted by $C_3-C_7$ cycloalkyl, halo, hydroxy, $C_1-C_4$ alkoxy, halo($C_1-C_4$)alkoxy, $C_3-C_7$ cycloalkyloxy, $C_3-C_7$ cycloalkyl($C_1-C_4$)alkoxy, —COOH, $C_1-C_4$ alkoxycarbonyl, —CONR³R⁴, —NR³R⁴, —S(O)$_p$($C_1-C_4$ alkyl), —SO₂(aryl), —SO₂NR³R⁴, morpholino, aryl, aryloxy, aryl($C_1-C_4$) alkoxy or het, and said $C_2-C_4$ alkenyl being optionally substituted by aryl;

R¹ and R² are each independently selected from H, fluoro, chloro, bromo, $C_1-C_4$ alkyl and halo($C_1-C_4$)alkyl;

R³ and R⁴ are either each independently selected from H and $C_1-C_4$ alkyl or, when taken together, are $C_5-C_7$ alkylene;

p is 0, 1 or 2;

"aryl", used in the definition of R and "het", means phenyl or naphthyl, each optionally substituted by 1 or 2 substitutents each independently selected from $C_1-C_4$ alkyl, $C_1-C_4$ alkoxy, hydroxy, halo, halo($C_1-C_4$)alkyl and —NR³R⁴;

"het", used in the definition of R, means furyl, thienyl, pyrrolyl, pyrazolyl, imidazolyl, triazolyl, tetrazolyl, oxazolyl, isoxazolyl, thiazolyl, isothiazolyl, oxadiazolyl, thiadiazolyl, pyridinyl, pyridazinyl, pyrimidinyl or pyrazinyl, each being optionally benzo-fused and optionally substituted, including in the benzo-fused portion, by 1 or 2 substituents each independently selected from $C_1-C_4$ alkyl, $C_3-C_7$ cycloalkyl, $C_1-C_4$ alkoxy, halo, hydroxy, —COOH, $C_1-C_4$ alkoxycarbonyl, allyloxycarbonyl, —CONR³R⁴, —NR³R⁴, —S(O)$_p$($C_1-C_4$ alkyl), —SO₂NR³R⁴, halo($C_1-C_4$)alkyl, hydroxy($C_1-C_4$) alkyl, $C_1-C_4$ alkoxy($C_1-C_4$)alkyl, R³R⁴NCO($C_1-C_4$) alkyl, aryl, arylalkyl, het¹ and het¹($C_1-C_4$)alkyl, and/or by an oxido substituent on a ring nitrogen heteroatom when "het" includes a pyridinyl, pyridazinyl, pyrimidinyl or pyrazinyl group; and "het¹", used in the definition of "het", means furyl, thienyl, pyrrolyl, pyrazolyl, imidazolyl, triazolyl, tetrazolyl. oxazolyl, isoxazolyl, thiazolyl, isothiazolyl, oxadiazolyl, thiadiazolyl, pyridinyl, pyridazinyl, pyrimidinyl or pyrazinyl, each optionally substituted by 1 or 2 $C_1$–$C_4$ alkyl substituents.

In the above definitions, "halo" means fluoro, chloro, bromo or iodo and alkyl, alkoxy and alkylene groups having three or more carbon atoms and alkenyl groups having 4 or more carbon atoms can be straight- or branched-chain.

The definition "$C_1$–$C_4$ alkyl" covers methyl, ethyl, n-propyl, isopropyl, n-butyl, sec-butyl and tert-butyl groups. The definition "$C_1$–$C_4$ alkoxy" covers the corresponding alkoxy groups.

Where R is a 5-membered ring heteroaryl group, this definition covers 1,2,3-triazolyl, 1,2,4-triazolyl and tetrazolyl.

Where R is a 6-membered ring heteroaryl group, this definition includes, in particular, 2-, 3- and 4-pyridinyl, 3- or 4pyridazinyl, 2-, 4- or 5-pyrimidinyl and 2-pyrazinyl.

Where "het" is a benzo-fused heteroaryl group, this may be attached to the remainder of the molecule via the heteroaryl or benzo-fused portion of the "het" group.

Preferably, R is triazolyl or tetrazolyl, each substituted by 1 or 2 substituents each independently selected from $C_1$–$C_4$ alkyl, $C_2$–$C_4$ alkenyl, $C_3$–$C_7$ cycloalkyl, halo, hydroxy, $C_1$–$C_4$ alkoxycarbonyl, aryl and het, said $C_1$–$C_4$ alkyl being optionally substituted by halo, hydroxy, $C_1$–$C_4$ alkoxy, halo $(C_1$–$C_4)$alkoxy, $C_3$–$C_7$ cycloalkyl$(C_1$–$C_4)$alkoxy, —COOH, $C_1$–$C_4$ alkoxycarbonyl, —$NR^3R^4$, —$SO_2$(aryl), morpholino, aryl, aryloxy, aryl$(C_1$–$C_4)$alkoxy or het; or is pyridinyl or pyrimidinyl.

More preferably, R is 1,2,3-triazol-4-yl, 1,2,4-triazol-3yl, 1,2,4-triazol-4-yl or tetrazol-5yl, each substituted by 1 or 2 substituents each independently selected from $C_1$–$C_4$ alkyl, $C_2$–$C_4$ alkenyl, $C_3$–$C_7$ cycloalkyl, halo, hydroxy, $C_1$–$C_4$ alkoxycarbonyl, aryl and het, said $C_1$–$C_4$ alkyl being optionally substituted by halo, hydroxy, $C_1$–$C_4$ alkoxy, halo $(C_1$–$C_4)$alkoxy, $C_3$–$C_7$ cycloalkyl$(C_1$–$C_4)$alkoxy. —COOH, $C_1$–$C_4$ alkoxycarbonyl, —$NR^3R^4$, —$SO_2$(aryl), morpholino, aryl, aryloxy, aryl$(C_1$–$C_4)$alkoxy or het; or is pyridin-2-yl, pyridin-3-yl, pyridin-4-yl, pyrimidin-2-yl or pyrimidin-5-yl. Yet more preferably, R is 1,2,3-triazol-4yl, 1,2,4-triazol-3yl, 1,2,4-triazol-4-yl or tetrazol-5-yl, each substituted by 1 or 2 substituents each independently selected from methyl, ethyl, propyl, allyl, cyclopropyl, cyclohexyl, bromo, hydroxy, ethoxycarbonyl, 2-chlorophenyl, 3-chlorophenyl, 4-chlorophenyl, 4-dimethylaminophenyl, 2-hydroxyphenyl, 2-methoxyphenyl, 3-methoxyphenyl, -4-methoxyphenyl, 2-methylphenyl, phenyl, 4-trifluoromethylphenyl, 2-amino-1,3,4-oxadiazol-5-yl, 2-carboxypyridin-5-yl, 1.5-dimethyl-1H-pyrazol-3-yl, 1H-imidazol-1-yl, 1-methylimidazol-2-yl, 1-methylimidazol-4-yl, 1-methylimidazol-5-yl, 3-methylisothiazol-4-yl, 4-methyl-1H-imidazol-5-yl, 3-methyl-1,2,4-oxadiazol-5-yl, 1-methyl-1H-pyrazol-4yl, 5-methyl-1H-pyrazol-3-yl, 1-methyl-1H-pyrazol-5-yl, 1-oxidopyridin-3-yl, 2-methylpyridin-3-yl, 2-methypyridin-5-yl, 1-phenylimidazol-4-yl, 5-phenylpyridin-3-yl, 2-phenylpyridin-5-yl, 1-methylpyrrol-2-yl, 4-methyl-1,2,3-thiadiazol-5yl, 2-methylthiazol-4-yl, 1-methyl-1H-1,2,4-triazol-5-yl, 3-(prop-1-yl)-1H-pyrazol-5-yl, pyrazin-2-yl, 1H-pyrazol-4-yl, pyridazin-4-yl, pyridin-2-yl, pyridin-3-yl, pyridin-4-yl, pyrimidin-2-yl, thien-2-yl, 1H-1,2,4-triazol-5yl, 1H-1,2,3-triazol-5-yl, quinolin-3-yl and quinolin-6-yl, said methyl, ethyl or propyl being optionally substituted by fluoro, hydroxy, methoxy, ethoxy, 2,2,2-trifluoroethoxy, cyclohexylmethoxy, cyclopentylmethoxy, —COOH, methoxycarbonyl, dimethylamino, 4-chlorophenylsulphonyl, morpholino, phenyl, phenoxy, benzyloxy, pyridin-2-yl, pyridin-3-yl or pyridin-4-yl; or is pyridin-2-yl, pyridin-3-yl, pyridin-4-yl, pyrimidin-2-yl or pyrimidin-5-yl.

Examples of R include:

1-(2-hydroxyethyl)-5-phenyl-1,2,3-triazol-4-yl, 1-(2-hydroxyethyl)-4-phenyl-1,2,3-triazol-5-yl, 2-(2-hydroxyethyl)-5-phenyl-1,2,3-triazol-4-yl, 1-methyl-5-phenyl-1,2,3-triazol-4-yl, 1-methyl-4-phenyl-1,2,3-triazol-5-yl, 2-methyl-5phenyl-1,2,3-triazol-4-yl, 5-phenyl-1H-1,2,3-triazol-4-yl.

1-methyl-1H-1,2,4-triazol-3-yl, 2-methyl-2H-1,2,4-triazol-3-yl, 4-(2-hydroxyethyl)-4H-1,2,4-triazol-3-yl, 4-methyl-4H-1,2,4-triazol-3-yl, 3(2-amino-1,3,4-oxadiazol-5-yl)-5-methyl-4H-1,2,4-triazol-4-yl, 3-benzyl-5-(pyridin-3-yl)-4H-1,2,4-triazol-4-yl, 3-benzyloxymethyl-5-(pyridin-3-yl)-4H-1,2,4-triazol-4-yl, 3-bromo-5-(pyridin-3-yl)-4H-1,2,4-triazol-4-yl, 3-(3-carboxyprop-1-yl)-5-(pyridin-3-yl)-4H-1,2,4-triazol-4-yl, 3-(2-carboxypyridin-5-yl)-5-methoxymethyl-4H-1,2,4-triazol-4-yl, 3-(2-chlorophenyl)-5-methoxymethyl-4H-1,2,4-triazol-4-yl, 3-(2-chlorophenyl)-5-methyl-4H-1,2,4-triazol-4-yl, 3-(3-chlorophenyl)-5-methyl-4H-1,2,4-triazol-4-yl, 3-(4-chlorophenyl)-5-methyl-4H-1,2,4-triazol-4-yl, 3-(4-chlorophenylsulphonylmethyl)-5-methyl-4H-1,2,4-triazol-4-yl, 3-cyclohexylmethoxymethyl-5-(pyridin-3-yl)-4H-1,2,4-triazol-4-yl, 3-cyclopentylmethoxymethyl-5-(pyridin-3-yl)-4H-1,2,4-triazol-4-yl, 3-cyclopropyl-5-methyl-4H-1,2,4-triazol-4yl, 3,5-di(methoxymethyl)-4H-1,2,4-triazol-4-yl, 3-(N,N-dimethylaminomethyl)-5-ethyl-4H-1,2,4-triazol-4-yl, 3-(N,N-dimethylaminomethyl)-5_(pyridin-3-yl)-4H-1,2,4-triazol-4-yl, 3-(4-dimethylaminophenyl)-5methyl-4H-1,2,4-triazol-4-yl, 3-(1,5-dimethyl-1H-pyrazol-3-yl)-5-methoxymethyl-4H-1,2,4-triazol-4yl, 3-(1,5-dimethyl-1H-pyrazol-3-yl)-5-methyl-4H-1,2,4-triazol-4-yl, 3,5-dimethyl-4H-1,2,4-triazol-4-yl, 3,5-diphenyl-4H-1,2,4-triazol-4-yl, 3-(2-ethoxyethyl)-5-(pyridin-3-yl)-4H-1,2,4-triazol-4-yl, 3-ethoxymethyl-5-(pyridin-3-yl)-4H-1,2,4-triazol-4-yl, 3-ethoxycarbonyl-4H-1,2,4-triazol-4-yl, 3-ethyl-5-(2-chlorophenyl)-4H-1,2,4-triazol-4-yl, 3-ethyl-5-(2-methoxyphenyl)-4H-1,2,4-triazol-4-yl, 3-ethyl-5-(1-methylpyrazol-5-yl)-4H-1,2,4-triazol-4-yl, 3-ethyl-5-methyl-4H-1,2,4-triazol-4-yl, 3-ethyl-5-morpholinomethyl-4H-1,2,4-triazol-4-yl,
3-ethyl-5-(pyridin-3-yl)-4H-1,2,4-triazol-4-yl,
3-ethyl-4H-1,2,4-triazol-4-yl,
3-(2-hydroxyethyl)-5-methyl-4H-1,2,4-triazol-4-yl,
3-hydroxymethyl-5-methyl-4H-1,2,4-triazol-4-yl,
3-hydroxymethyl-5-phenyl-4H-1,2,4-triazol-4-yl,
3-hydroxymethyl-5-(pyridin-3-yl)-4H-1,2,4-triazol-4-yl,
3-hydroxymethyl-4H-1,2,4-triazol-4-yl,
3-hydroxy-5-methyl-4H-1,2,4-triazol-4-yl,
3-(2-hydroxyphenyl)-5-methyl-4H-1,2,4-triazol-4-yl,
3-(1H-imidazol-1-yl)-5-methyl-4H-1,2,4-triazol-4yl,
3-(2-methoxyethyl)-5-(pyridin-3-yl)-4H-1,2,4-triazol-4yl,
3-methoxymethyl-5-(1-methyl-1H-pyrazol-5-yl)-4H-1,2,4-triazol-4-yl,
3-methoxymethyl-5-(1-methylpyridin-5-yl)-4H-1,2,4-triazol-4-yl,
3-methoxymethyl-5-(2-methylthiazol-4yl)-4H-1,2,4-triazol-4-yl,
3-methoxymethyl-5-(1-oxidopyridin-3-yl)-4H-1,2,4-triazol-4-yl,
3-methoxymethyl-5-(1-phenylimidazol-4-yl)-4H-1,2,4-triazol-4-yl,
3-methoxymethyl-5-(5-phenylpyridin-3-yl)-4H-1,2,4-triazol-4-yl,
3-methoxymethyl-5-(2-phenylpyridin-5-yl)-4H-1,2,4-triazol-4-yl,
3-methoxymethyl-5-(pyridin-3-yl)-4H-1,2,4-triazol-4-yl,
3-methoxymethyl-5-(pyridin-3-ylmethyl)-4-H1,2,4-triazol-4-yl,
3-methoxymethyl-5-(quinolin-3-yl)-4H-1,2,4-triazol-4-yl,
3-methoxymethyl-5-(quinolin-6-yl)-4H-1,2,4-triazol-4-yl,
3-(2-methoxyphenyl)-5-methyl-4H-1,2,4-triazol-4-yl,
3-(3-methoxyphenyl)-5-methyl-4H-1,2,4-triazol-4-yl,
3-(4-methoxyphenyl)-5-methyl-4H-1,2,4-triazol-4-yl
3-methyl-5-(1-methylimidazol-2-yl)-4H-1,2,4-triazol-4-yl,
3-methyl-5-(1-methylimidazol-4-yl)-4H-1,2,4-triazol-4-yl,
3-methyl-5-(1-methylimidazol-5-yl)-4H-1,2,4-triazol-4-yl,
3-(3-methylisothiazol-4-yl)-5-methyl-4H-1,2,4-triazol-4-yl,
3-methyl-5-(4-methyl-1H-imidazol-5-yl)-4H-1,2,4-triazol-4-yl,
3-methyl-5-(3-methyl-1,2,4-oxadiazol-5-yl)-4H-1,2,4-triazol-4-yl,
3-methyl-5-(2-methylpyridin-3-yl)-4H-1,2,4-triazol-4-yl,
3-methyl-5-(2-methylpyridin-5-yl)-4H-1,2,4-triazol-4-yl,
3-methyl-5-(1-methylpyrazol-5-yl)-4H-1,2,4-triazol-4-yl,
3-methyl-5-(5-methyl-1H-pyrazol-3-yl)-4H-1,2,4-triazol-4-yl,
3-methyl-5-(2-methylphenyl)-4H-1,2,4-triazol-4-yl,
3-methyl-5-(1-methylpyrrol-2-yl)-4H-1,2,4-triazol-4-yl,
3-methyl-5-(4-methyl-1,2,3-thiadiazol-5yl)-4H-1,2,4-triazol-4-yl,
3-methyl-5-(2-methylthiazol-4-yl)-4H-1,2,4-triazol-4-yl,
3-methyl-5-(1-methyl-1H-1,2,4-triazol-5-yl)-4H-1,2,4-triazol-4-yl,
3-methyl-5-(1-methyl-1H-pyrazol-4-yl)-4H-1,2,4-triazol-4-yl,
3-(3-methyl-1,2,4-oxadiazol-5-yl)-5-(pyridin-3-yl)-4H-1,2,4-triazol-4-yl,
3-methyl-5-phenyl-4H-1,2,4-triazol-4yl,
3-methyl-5-(3-[prop-1-yl]-1H-pyrazol-5-yl)-4H-1,2,4-triazol-4-yl,
3-methyl-5-(pyrazin-2-yl)-4H-1,2,4-triazol-4-yl,
3-methyl-5-(1H-pyrazol-4-yl)-4H1,2,4-triazol-4-yl,
3-methyl-5-(pyridin-2-yl)-4H-1,2,4-triazol-4-yl,
3-methyl-5-(pyridin-3-yl)-4H-1,2,4-triazol-4-yl,
3-methyl-5-(pyridin-4-yl)-4H-1,2,4-triazol-4-yl,
3-methyl-5-(pyridin-2-ylmethyl)-4H-1,2,4-triazol-4-yl,
3-methyl-5-(pyridin-3-ylmethyl)-4H-1,2,4-triazol-4-yl,
3-methyl-5-(pyridin-4-ylmethyl)-4H-1,2,4-triazol-4-yl,
3-methyl-5-(pyridazin-4-yl)-4H-1,2,4-triazol-4-yl,
3-methyl-5-(pyrimidin-2-yl)-4H-1,2,4-triazol-4-yl,
3-methyl-5-(thien-2-yl)-4H-1,2,4-triazol-4-yl,
3-methyl-4H-1,2,4-triazol-4-yl,
3-methyl-5-(1H-1,2,3-triazol-5-yl)-4H-1,2,4-triazol-4-yl,
3-methyl-5-(1H-1,2,4-triazol-5-yl)-4H-1,2,4-triazol-4-yl,
3-morpholinomethyl-5-(pyridin-3-yl)-4H-1,2,4-triazol-4-yl,
3-phenoxymethyl-5-(pyridin-3-yl)-4H-1,2,4-triazol-4-yl,
3-(2-phenylethyl)-5-(pyridin-3-yl)-4H-1,2,4-triazol-4-yl,
3-(pyridin-3-yl)-4H-1,2,4-triazol-4-yl,
3-methyl-5-(4-trifluoromethylphenyl)-4H-1,2,4-triazol-4-yl,
1-allytetrazol-5-yl,
1-benzyltetrazol-5-yl,
1-carboxymethyltetrazol-5-yl,
1-cyclohexyltetrazol-5-yl,
1-ethyltetrazol-5-yl,
1-(2-hydroxyethyl)tetrazol-5-yl,
1-(3-hydroxypropyl)tetrazol-5-yl,
1-methoxycarbonylmethyltetrazol-5-yl,
1-(2-methoxyethyl)tetrazol-5yl,
1-methyltetrazol-5-yl,
1-(2-phenylethyl)tetrazol-5-yl,
1-phenyltetrazol-5-yl,
1-(prop-2-yl)tetrazol-5-yl,
1-(2,2,2-trifluoroethyl)tetrazol-5-yl,
pyridin-2-yl,
pyridin-3-yl,
pyridin-4-yl,
pyrimidin-2-yl and
pyrimidin-5-yl.
Most preferably R is
1-(3-hydroxypropyl)tetrazol-5-yl,
4-methyl-4H-1,2,4-triazol-3-yl,
1-(2-hydroxyethyl)-5-phenyl-1,2,3-triazol-4-yl,
3-methyl-5-(pyridin-3-yl)-4H-1,2,4-triazol-4-yl,
3-methyl-5-(pyridin-3-ylmethyl)-4H-1,2,4-triazol-4-yl,
3-methoxymethyl-5-(pyridin-3-yl)-4H-1,2,4-triazol-4-yl,
3-methoxymethyl-5-(quinolin-3-yl)-4H-1,2,4-triazol-4-yl,
3-methoxymethyl-5-(quinolin-6-yl)-4H-1,2,4-triazol-4-yl or 3-(1,5-dimethyl-1H-pyrazol-3-yl)-5-methyl-4H-1,2,4-triazol-4-yl.

Preferably, $R^1$ and $R^2$ are each independently selected from chloro and $C_1$–$C_4$ alkyl, especially methyl or ethyl. Most preferably, $R^1$ and $R^2$ are each chloro.

Preferably, $R^3$ and $R^4$ are each independently selected from H and $C_1$–$C_4$ alkyl. Most preferably, $R^3$ and $R^4$ are each methyl.

Preferably, "aryl" means phenyl optionally substituted by 1 or 2 substituents each independently selected from methyl, methoxy, hydroxy, chloro, trifluoromethyl and dimethylamino. Examples of "aryl" include 2-chlorophenyl, 3-chlorophenyl, 4-chlorophenyl, 4-dimethylaminophenyl, 2-hydroxyphenyl, 2-methoxyphenyl, 3-methoxyphenyl, 4-methoxyphenyl, 2-methylphenyl, phenyl and 4-trifluoromethylphenyl.

Preferably, "het" means thienyl, pyrrolyl, pyrazolyl, imidazolyl, triazolyl, thiazolyl, isothiazolyl, oxadiazolyl, thiadiazolyl, pyridinyl, pyridazinyl, pyrimidinyl or pyrazinyl, each being optionally benzo-fused and optionally substituted by 1 or 2 substituents each independently selected from $C_1$–$C_4$ alkyl, —COOH, —$NR^3R^4$ and phenyl, and/or by an oxido substituent on a ring nitrogen heteroatom of said pyridinyl, pyridazinyl, pyrimidinyl or pyrazinyl group.

Examples of "het" include thien-2yl, 1-methylpyrrol-2yl, 1H-pyrazol-4-yl, 1-methyl-1H-pyrazol-4-yl, 5-methyl-1H-pyrazol-3-yl, 1-methyl-1H-pyrazol-4-yl, 1,5-dimethyl-1H-pyrazol-3-yl, 3-(prop-1-yl)-1H-pyrazol-5-yl, 1H-imidazol-1-yl, 1-methylimidazol-2-yl, 1-methylimidazol-4yl, 1-methylimidazol-5-yl, 4-methyl-1H-imidazol-5-yl, 1-phenylimidazol-4-yl, 1H-1,2,3-triazol-5-yl, 1H-1,2,4-triazol-5-yl, 1-methyl-1H-1,2,4-triazol-5-yl, 2-methylthiazol-4-yl, 3-methylisothiazol-4-yl, 2-amino-1,3,4-oxadiazol-5-yl, 3-methyl-1,2,4-oxadiazol-5-yl, 4-methyl-1,2,3-thiadiazol-5-yl, pyridin-2-yl, pyridin-3-yl, pyridin-4-yl, 2-methylpyridin-3-yl, 2-methylpyridin-5-yl, 1-oxidopyridin-3-yl, 2-carboxypyridin-5-yl, 5-phenylpyridin-3-yl, 2-phenylpyridin-5-yl, pyridazin-4yl, pyrimidin-2-yl, pyrazin-2-yl, quinolin-3yl and quinolin-6-yl.

The pharmaceutically acceptable salts of the compounds of the formula (I) include the acid addition and the base salts thereof.

Suitable acid addition salts are formed from acids which form non-toxic salts and examples are the hydrochloride, hydrobromide, hydroiodide, sulphate, hydrogen sulphate, nitrate, phosphate, hydrogen phosphate, acetate, maleate, fumarate, lactate, tartrate, citrate, gluconate, succinate, benzoate, methanesulphonate, benzenesulphonate and p-toluenesulphonate salts.

Suitable base salts are formed from bases which form non-toxic salts and examples are the calcium, lithium, magnesium, potassium, sodium, zinc, ethanolamine, diethanolamine and triethanolamine salts.

For a review on suitable salts see Berge et al, J. Pharm. Sci., 66, 1–19 (1977).

A compound of the formula (I) may contain one or more asymmetric carbon atoms and may therefore exist in two or more stereoisomeric forms, or it may exist as tautomers. The present invention includes the individual stereoisomers and tautomers of the compounds of the formula (I) and mixtures thereof.

Separation of diastereoisomers may be achieved by conventional techniques, e.g. by fractional crystallisation, chromatography or H.P.L.C. of a stereoisomeric mixture of a compound of the formula (I) or a suitable salt or derivative thereof. An individual enantiomer of a compound of the formula (I) may also be prepared from a corresponding optically pure intermediate or by resolution, such as by H.P.L.C. of the corresponding racemate using a suitable chiral support or by fractional crystallisation of the diastereoisomeric salts formed by reaction of the corresponding racemate with a suitable optically active acid or base.

Certain compounds of the formula (I) can exist in the form of particular stereoisomers known as atropisomers. Atropisomers are isomers that can be separated only because rotation about single bonds is prevented or greatly slowed (see "Advanced Organic Chemistry", Third Edition, Jerry March, John Wiley and Sons (1985)). They can be separated by conventional methods such as by those described in the preceding paragraph. The present invention includes the individual atropisomers of the compounds of the formula (I) and mixtures thereof.

Preferred examples of the compounds of the formula (I) are those wherein (i) R is 1-(3-hydroxypropyl)tetrazol-5-yl, $R^1$ is chloro and $R^2$ is chloro;

(ii) R is 4-methyl-4H-1,2,4-triazol-3-yl, $R^1$ is chloro and $R^2$ is chloro;

(iii) R is 1-(2-hydroxyethyl)-5-phenyl-1,2,3-triazol-4-yl, $R^1$ is chloro and $R^2$ is chloro;

(iv) R is 3-methyl-5-(pyridin-3-yl)-4H-1,2,4-triazol-4-yl, $R^1$ is chloro and $R^2$ is chloro;

(v) R is 3-methyl-5-(pyridin-3-ylmethyl)-4H-1,2,4-triazol-4-yl, $R^1$ is chloro and $R^2$ is chloro;

(vi) R is 3-methoxymethyl-5-(pyridin-3-yl)-4H-1,2,4-triazol-4-yl, $R^1$ is chloro and $R^2$ is chloro;

(vii) R is 3-(1,5-dimethyl-1H-pyrazol-3-yl)-5-methyl-4H-1,2,4-triazol-4-yl, $R^1$ is chloro and $R^2$ is chloro;

(viii) R is 3-methoxymethyl-5-(pyridin-3-yl)-4H-1,2,4-triazol-4-yl, $R^1$ is chloro and $R^2$ is methyl;

(ix) R is 3-methoxymethyl-5-(pyridin-3-yl)-4H-1,2,4-triazol-4-yl, $R^1$ is methyl and $R^2$ is chloro;

(x) R is 3-methoxymethyl-5-(quinolin-3-yl)-4H-1,2,4-triazol-4-yl, $R^1$ is chloro and $R^2$ is chloro; or (xi) R is 3-methoxymethyl-5-(quinolin-6-yl)-4H-1,2,4-triazol-4-yl, $R^1$ is chloro and $R^2$ is chloro: or an individual stereoisomer or a pharmaceutically acceptable salt of any thereof. Particularly preferred compounds of the formula (I) are (i) R-(-)-6,7-dichloro-5-[3-methoxymethyl-5-(3-pyridyl)-4H-1,2,4-triazol-4-yl]-2,3(1H,4H)-quinoxalinedione or a pharmaceutically acceptable salt there of and (ii) R-(-)-6,7-dichloro-5-[3-methoxymethyl-5-(3-pyridyl)-4H-1,2,4-triazol-4-yl]-2,3(1H,4H)-quinoxalinedione sodium salt.

All the compounds of the formula (I) can be prepared by acidic or basic hydrolysis of a compound of the formula:

(II)

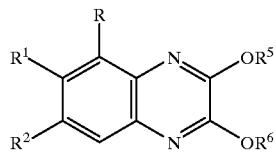

wherein R, $R^1$ and $R^2$ are as previously defined for a compound of the formula (I) and $R^5$ and $R^6$, either when taken alone or together, represent a group or groups that can be hydrolytically cleaved under acidic or basic conditions to provide a quinoxalinedione of the formula (I). Such group or groups are conventional and suitable examples will be well-known to the skilled person.

Preferably $R^5$ and $R^6$ are either each independently selected from $C_1$–$C_4$ alkyl (preferably methyl or ethyl) and benzyl, optionally ring-substituted by from 1 to 3 substituents each independently selected from $C_1$–$C_4$ alkyl, $C_1$–$C_4$ alkoxy, halo, nitro and trifluoromethyl, or, when taken together, represent $C_1$–$C_5$ alkylene, CH(phenyl), CH(4-methoxyphenyl) or CH(3,4-dimethoxyphenyl).

Preferably, the reaction is carried out by acidic hydrolysis of a compound of the formula (II).

In a typical procedure, a compound of the formula (II) is treated with an aqueous solution of a suitable acid, e.g. a mineral acid such as hydrochloric acid, optionally in the presence of a suitable organic co-solvent, e.g. 1,4-dioxane. The reaction is usually carried out by heating the mixture at up to the reflux temperature of the solvent(s). The intermediates of the formula (II) can be prepared by a variety of conventional methods, for example, as described below.

(a) The compounds of the formula (II) where R is a substituted tetrazol-5-yl group can be prepared by the route shown in Scheme I:

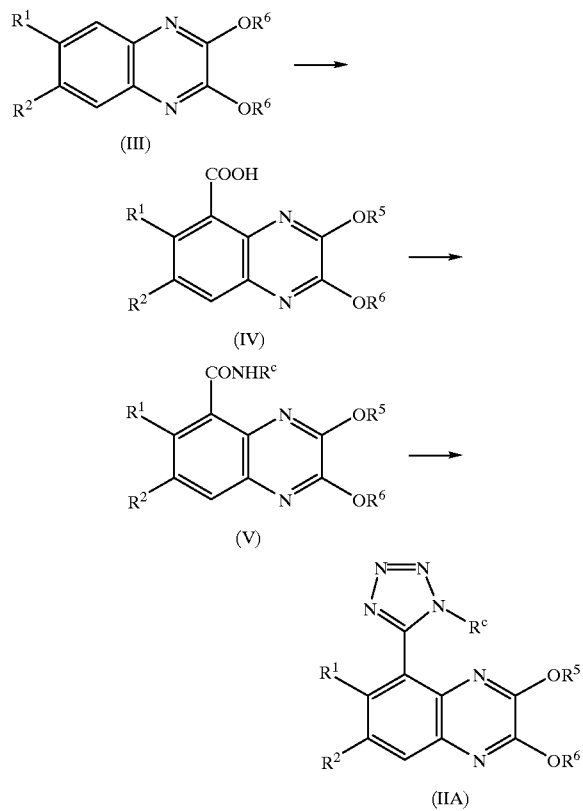

Scheme I wherein $R^1$, $R^2$, $R^5$ and $R^6$ are as previously defined for a compound of the formula (II) and $R^c$ is a suitable substituent as previously defined for R for a compound of the formula (I). In a typical procedure, a compound of the formula (III) is first deprotonated with a suitable base, e.g. lithium diisopropylamide, in a suitable solvent, e.g. tetrahydrofuran, and the carbanion obtained is then treated with carbon dioxide. The carboxylic acid of the formula (IV) obtained is converted to the corresponding acid chloride using oxalyl chloride and a catalytic amount of N,N-dimethylformamide in a suitable solvent, e.g. dichloromethane, which is then converted to the secondary amide of the formula (V) by in situ treatment with an amine of the formula:

$$R^cNH_2.$$

The amide of the formula (V) is first treated with phosphorus pentachloride in a suitable solvent, e.g. toluene, and the intermediate obtained is reacted in situ with trimethylsilyl azide to provide a compound of the formula (IIA).

(b) The compounds of the formula (II) where R is an optionally benzo-fused/substituted 5-or 6-membered ring heteroaryl group which is linked to the quinoxaline ring by a ring carbon atom, can be prepared by the route shown in Scheme II:

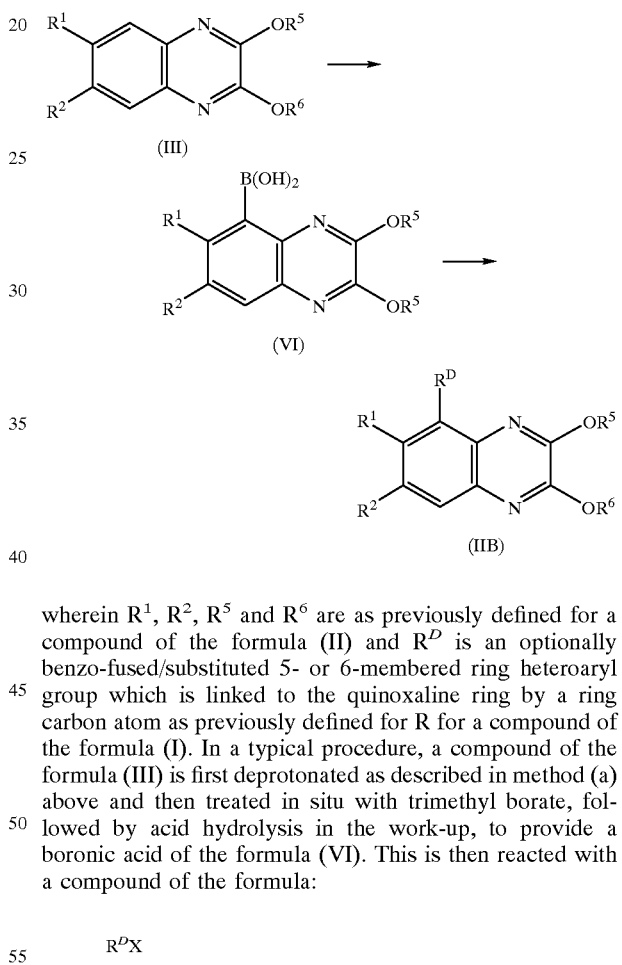

Scheme II wherein $R^1$, $R^2$, $R^5$ and $R^6$ are as previously defined for a compound of the formula (II) and $R^D$ is an optionally benzo-fused/substituted 5- or 6-membered ring heteroaryl group which is linked to the quinoxaline ring by a ring carbon atom as previously defined for R for a compound of the formula (I). In a typical procedure, a compound of the formula (III) is first deprotonated as described in method (a) above and then treated in situ with trimethyl borate, followed by acid hydrolysis in the work-up, to provide a boronic acid of the formula (VI). This is then reacted with a compound of the formula:

$$R^DX$$

wherein X is bromo, iodo, or trifluoromethylsulphonyloxy, and $R^D$ is as defined above, in the presence of a suitable catalyst, e.g. tetrakis(triphenylphosphine)palladium (O), and under suitable conditions to provide a compound of the formula (IIB).

(c) The compounds of the formula (II) where R is an optionally 4-substituted-4H-1,2,4-triazol-3-yl group can be prepared by treatment of a compound of the formula (V) first with phosphorus pentachloride in a suitable solvent, e.g. toluene, followed by reaction of the intermediate obtained in situ with formyl hydrazine in the presence of a suitable base, e.g. triethylamine.

(d) The compounds of the formula (II) where R is a 1- or 2-(optionally substituted $C_1$–$C_4$ alkyl)-substituted-1,2,4-triazol-3-yl group can be prepared by treatment of a compound of the formula (V) where $R^C$ is H with a N,N-di ($C_1$–$C_4$ alkyl)formamide di($C_1$–$C_4$ alkyl)acetal, preferably N,N-dimethylformamide dimethyl acetal, reacting the intermediate formamidine obtained with hydrazine in the presence of a suitable acid, e.g. acetic acid, and then by treatment of the resulting tautomeric mixture of 5-(1H-and 2H-1,2,4-triazol-3-yl)-substituted quinoxalines first with a suitable base, e.g. sodium hydride, in a suitable solvent, e.g. N,N-dimethylformamide, followed by a suitable optionally substituted $C_1$–$C_4$ alkyl halide (e.g. iodomethane to prepare N-methyl-substituted products). The mixture of 1- and 2-(optionally substituted $C_1$–$C_4$ alkyl)-substituted-1,2,4-triazol-3-yl products obtained can be separated by a conventional method e.g. chromatography.

(e) The compounds of the formula (II) where R is an optionally substituted 1,2,4-triazol-4-yl group can be prepared by the route shown in Scheme III:

Scheme III

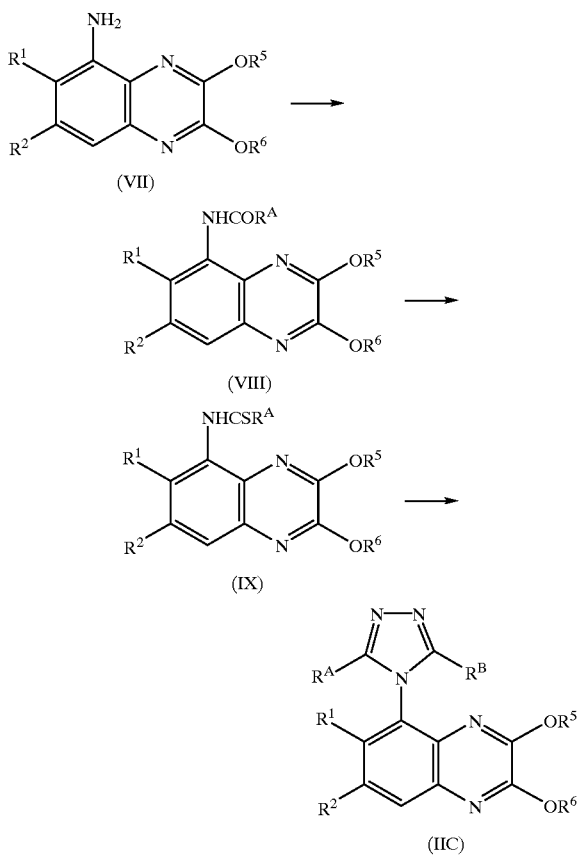

wherein $R^1$, $R^2$, $R^5$ and $R^6$ are as previously defined for a compound of the formula (II) and $R^A$ and $R^B$ are each independently H or a suitable substituent as previously defined for R for a compound of the formula (I). In a typical procedure, a 5-aminoquinoxaline of the formula (VII) is reacted with a compound of the formula:

$R^A COX^1$ wherein $X^1$ is a suitable leaving group, e.g. chloro or bromo, in a suitable solvent, e.g. toulene or dichloromethane, and optionally in the presence of a suitable acid acceptor, e.g. pyridine, to provide an amide of the formula (VIII). An amide of the formula (VIII) can be converted to a thioamide of the formula (IX) by treatment with 2,4-bis(4-methoxyphenyl)-1,3-dithia-2,4-diphosphetane-2,4-disulphide (Lawesson's reagent) in a suitable solvent, e.g. toulene or tetrahydrofuran. A thioamide of the formula (IX) can be converted to a compound of the formula (IIC) by treatment with a compound of the formula:

$R^B CONHNH_2$ in the presence of mercury (II) oxide, optionally a desiccant, e.g. 4A molecular sieves, and a suitable solvent, e.g. n-butanol.

(f) The compounds of the formula (II) where R is an optionally benzo-fused/substituted 5- or 6-membered ring heteroaryl group which is linked to the quinoxaline ring by a ring carbon atom can be prepared by coupling a compound of the formula:

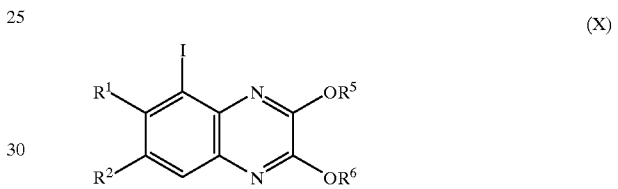

where $R^1$, $R^2$, $R^5$ and $R^6$ are as previously defined for a compound of the formula (II), with a compound of the formula:

$R^E X^2$ where $X^2$ is Sn($C^1$–$C^4$ alkyl)$_3$, ZnCl, ZnBr, ZnI or —B(OH)$_2$, and $R^E$ is as defined for this method for R, in the presence of a suitable catalyst, e.g. tetrakis(triphenylphosphine) palladium (O), under suitable conditions.

(g) The compounds of the formula (II) where R is an optionally substituted 1,2,3-triazol-4-yl group can be prepared by the route shown in Scheme IV:

Scheme IV

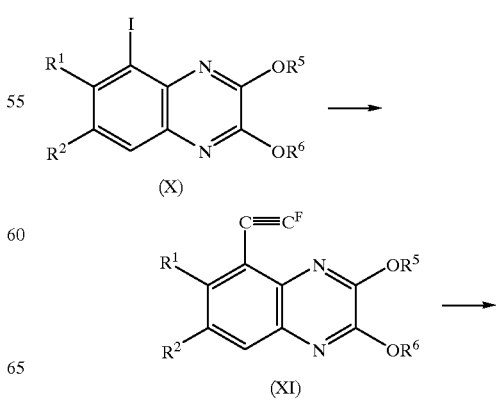

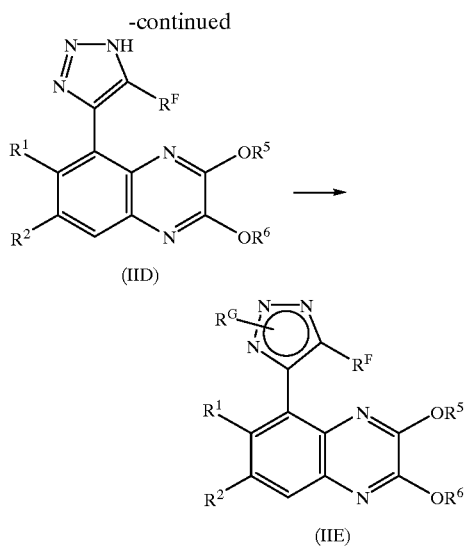

(IID)

(IIE)

wherein $R^1$, $R^2$, $R^5$ and $R^6$ are as previously defined for a compound of the formula (II) and $R^F$ is H, or $R^F$ and $R^G$ are each independently a suitable substituent as previously defined for R for a compound of the formula (I). In a typical procedure, a 5-iodoquinoxaline of the formula (X) is coupled with an acetylene of the formula:

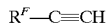

$R^F$—C≡CH under suitable conditions, e.g. using bis(triphenylphosphine) palladium (II) chloride, copper (I) iodide and triethylamine. The compound of the formula (XI) prepared is then reacted with trimethylsilyl azide to provide a compound of the formula (IID) which can be converted to a compound of the formula (IIE) by a conventional method, e.g. where $R^G$ is $C_1$–$C_4$ alkyl, by first deprotonating a compound of the formula (IID) using a suitable base, e.g. sodium hydride, followed by reaction with a $C_1$–$C_4$ alkyl halide, e.g. iodomethane. Where a mixture of the 1-, 2- and 3-substituted-1,2,3-triazol-4-yl isomers of a compound of the formula (IIE) is obtained, these may be separated by a conventional method, e.g. chromatography.

It will be realised that certain compounds of the formula (I) or (II) may be converted to other compounds of the formula (I) or (II), respectively, by conventional methods, e.g. by functional group interconversion techniques.

All of the above reactions and the preparations of novel starting materials used in the preceding methods are conventional and appropriate reagents and reaction conditions for their performance or preparation as well as procedures for isolating the desired products will be well known to those skilled in the art with reference to literature precedents and the Examples and Preparations hereto.

A pharmaceutically acceptable acid addition or base salt of a compound of the formula (I) may be readily prepared by mixing together solutions of a compound of the formula (I) and the desired acid or base, as appropriate. The salt may precipitate from solution and be collected by filtration or may be recovered by evaporation of the solvent.

The binding affinity of the compounds of the formula (I) and their salts for the glycine site of the NMDA receptor may be measured by testing their ability to displace a selective glycine site radioligand from rat brain membranes as described in Brit. J. Pharm., 104, 74 (1991). In a variation of this method, thoroughly washed membrane protein is incubated with [$^3$H]-L-689,560 (Mol.Pharmacol., 41, 923 (1992)) for 90 minutes using tris-acetate buffer (pH 7.4). Displacement of the radioligand, using a range of test compound concentrations, is used to derive $IC_{50}$ (50% inhibitory concentration) values.

Functional in vitro glycine antagonism is demonstrated by the ability of the compounds to inhibit the depolarizations in rat cortical slices induced by NMDA by a similar method to that described in J. Med. Chem., 33, 789 (1990) and Brit. J. Pharm., 84, 381 (1985). In a variation of the procedure, the response to a standard concentration of NMDA is measured in the presence of a range of test compound concentrations and the results obtained are used to derive $EC_{50}$ (50% effective concentration) values.

The binding affinity of the compounds of the invention for the AMPA receptor may be measured by testing their ability to displace for radioligand [$^3$H]-AMPA from rat brain membranes. Membrane homogenate is incubated with radioligand (10 nM) in the presence or absence of test compounds at various concentrations at 4° C. for 45 minutes. Free and bound radiolabel are separated by rapid filtration and radioactivity is measured by liquid scintillation counting.

The compounds of the formula (I) and their salts can be administered to a subject to be treated alone, but will generally be administered in admixture with a pharmaceutically acceptable diluent or carrier selected with regard to the intended route of administration and standard pharmaceutical practice. For example, they can be administered orally, including sublingually, in the form of tablets containing such excipients as starch or lactose, or in capsules or ovules either alone or in admixture with excipients, or in the form of elixirs, solutions or suspensions containing flavouring or colouring agents. They can be injected parenterally, for example, intravenously, intramuscularly or subcutaneously. For parenteral administration, they are best used in the form of a sterile aqueous solution which may contain other substances, for example, enough salts or glucose to make the solution isotonic with blood.

The compounds have potential for absorption through the gastrointestinal tract and thus administration by slow release formulations is also possible.

In general, a therapeutically effective daily oral dose of the compounds of formula (I) and their salts is likely to range from 0.1 to 100 mg/kg body weight of the subject to be treated, preferably 1 to 20 mg/kg, and an intravenous daily dose is likely to range from 0.01–20 mg/kg body weight of subject to be treated, preferably 0.1–20 mg/kg. The compounds of the formula (I) and their salts may also be administered by intravenous infusion at a dose which is likely to range from 0.01–10 mg/kg/hr.

Tablets or capsules of the compounds may be administered singly or two or more at a time, as appropriate.

The physician will determine the actual dosage which will be most suitable for an individual patient and it will vary with the age, weight and response of the particular patient. The above dosages are exemplary of the average case. There can, of course, be individual instances where higher or lower dosage ranges are merited, and such are within the scope of this invention.

Alternatively, the compounds of the formula (I) can be administered by inhalation or in the form of a suppository or pessary, or they may be applied topically in the form of a lotion, solution, cream, ointment or dusting powder. An alternative means of transdermal administration is by use of a skin patch. For example, they can be incorporated into a cream consisting of an aqueous emulsion of polyethylene glycols or liquid paraffin. They can also be incorporated, at a concentration of between 1 and 10% by weight, into an ointment consisting of a white wax or white soft paraffin base together with such stabilisers and preservatives as may be required.

It is to be appreciated that reference to treatment includes prophylaxis as well as the alleviation of established symptoms of the disease.

Thus the invention further provides:

i) a pharmaceutical composition comprising a compound of the formula (I), or a pharmaceutically acceptable salt thereof, together with a pharmaceutically acceptable diluent or carrier;

ii) a compound of the formula (I), or a pharmaceutically acceptable salt or composition thereof, for use as a medicament;

iii) the use of a compound of the formula (I), or of a pharmaceutically acceptable salt or composition thereof, for the manufacture of a medicament for the treatment of a disease by producing an antagonist effect at a NMDA receptor;

iv) use as in (iii) where the disease is an acute neurodegenerative or a chronic neurological disorder;

v) a method of treatment of a mammal to treat a disease by producing an antagonist effect at a NMDA receptor, which comprises treating said mammal with an effective amount of a compound of the formula (I) or with a pharmaceutically acceptable salt or composition thereof;

vi) a method as in (v) where the disease is an acute neurodegenerative or a chronic neurological disorder; and vii) a compound of the formula (II).

The following Examples and Preparations illustrate the preparation of the compounds of the formula (I) together with intermediates used in their synthesis.

Melting points were determined using a Buchi apparatus in glass capillary tubes and are uncorrected. Low Resolution Mass Spectroscopic (LRMS) data were recorded on a Fisons Trio 1000 Mass Spectrometer (thermospray using ammonium acetate in aqueous methanol as the carrier or atmospheric pressure chemical ionisation (APCI) using 97.5:2.5, by volume, methanol:acetic acid and gaseous nitrogen as the carrier). NMR data were recorded on a Bruker AC300 or a Varian Unity 300 NMR instrument (both 300 MHz) or a Unity Inova-400 (400 MHz) instrument and were consistent with the assigned structures. Flash chromatography was accomplished on Kieselgel 60 (230–400 mesh) from E. Merck, Darmstadt, Kieselgel 60 $F_{254}$ plates from E. Merck were used for thin layer chromatography (TLC) and the compounds were visualized with UV light or chloroplatinic acid/potassium iodide solution. In cases where compounds analysed as hydrates, the presence of water was evident by the enhanced peak due to water in the proton NMR spectra. The purity of the compounds was carefully assessed using analytical TLC and proton NMR (300 MHz) and the latter technique was used to calculate the amount of solvent in solvated samples. In multistep sequences, the purity and structure of intermediates were verified spectroscopically by proton NMR. Proton NMR shifts are quoted in parts per million downfield from tetramethylsilane.

Some abbreviations familiar to those skilled in the art have been used in the Examples and Preparations.

EXAMPLE 1

6,7-Dichloro-5-(4-pyridyl)-2,3(1H,4H)-quinoxalinedione

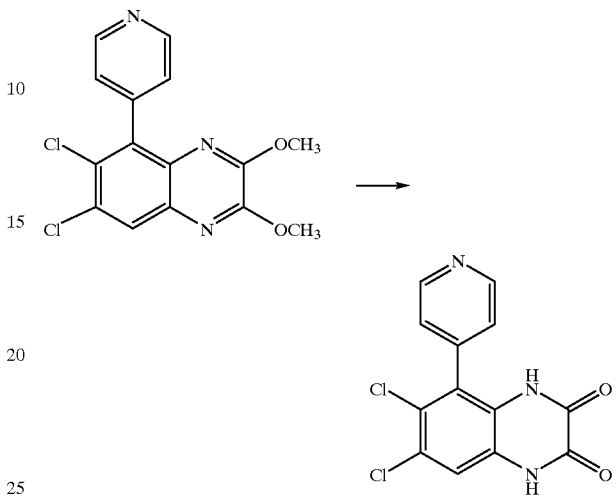

A mixture of 6,7-dichloro-2,3-dimethoxy-5-(4-pyridyl) quinoxaline (Preparation 2, 110 mg, 0.327 mmol), 2M aqueous hydrochloric acid solution (1 mL) and 1,4-dioxane (7 ml) was heated under reflux for 2 hours, cooled, and concentrated under reduced pressure. The solid residue was triturated with water, collected by filtration and washed with water and diethyl ether to give the title compound (17 mg, 17%) as a white solid, mp >300° C.

m/z (thermospray) 308 (MH$^+$).

Analysis (%): Found: C, 49.58; H, 2.36; N, 12.93. $C_{13}H_7Cl_2N_3O_2$. 0.5$H_2O$ requires C, 49.24; H, 2.54; N, 13.25.

EXAMPLES 2–107

The following tabulated Examples of the general formula:

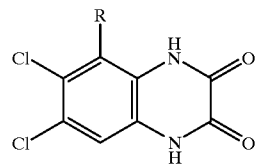

were prepared by a similar method to that of Example 1, using the corresponding 2,3-dimethoxyquinoxaline derivatives indicated and a reaction period that corresponded approximately to the complete consumption of starting material by TLC. In Examples 8, 82 and 84, concomitant ester hydrolysis occurred, while in Examples 104 to 106 the trityl group is cleaved.

TABLE 1

| Ex. No. | R | mp (° C.) | Molecular formula |
|---|---|---|---|
| 2 | 2-pyridyl | >300 | $C_{13}H_7Cl_2N_3O_2 \cdot 0.3H_2O$ |
| 3 | 2-pyrimidinyl | >300 | $C_{12}H_6Cl_2N_4O_2 \cdot 0.25H_2O$ |
| 4 | 5-pyrimidinyl | >300 | $C_{12}H_6Cl_2N_4O_2$ |
| 5 | 1-methyl-tetrazol-5-yl | >300 | $C_{10}H_6Cl_2N_6O_2 \cdot 0.25$ 1,4-dioxane |
| 6 | 1-cyclohexyl-tetrazol-5-yl | >300 | $C_{15}H_{14}Cl_2N_6O_2$ |
| 7 | 1-(2-phenylethyl)-tetrazol-5-yl | >300 | $C_{17}H_{12}Cl_2N_6O_2$ |
| 8 | 1-(carboxymethyl)-tetrazol-5-yl | 286–287 | $C_{11}H_6Cl_2N_6O_4 \cdot H_2O \cdot 0.1$ 1,4-dioxane |
| 9 | 1-isopropyl-tetrazol-5-yl | >300 | $C_{12}H_{10}Cl_2N_6O_2 \cdot 0.25\ H_2O$ |
| 10 | 1-ethyl-tetrazol-5-yl | >300 | $C_{11}H_8Cl_2N_6O_2 \cdot 0.25$ 1,4-dioxane |

TABLE 1-continued

| # | Structure | mp (°C) | Formula |
|---|---|---|---|
| 11 | [tetrazole with N-CH2-phenyl] | >300 | C₁₆H₁₀Cl₂N₆O₂ |
| 12 | [tetrazole with N-CH2CH2-OCH3] | 294–295 | C₁₂H₁₀Cl₂N₆O₃·0.1 1,4-dioxane |
| 13 | [tetrazole with N-phenyl] | >300 | C₁₅H₈Cl₂N₆O₂ |
| 14 | [tetrazole with N-CH2-CF3] | 297 | C₁₁H₅Cl₂F₃N₆O₂ |
| 15 | [tetrazole with N-allyl] | >300 | C₁₂H₈Cl₂N₆O₂ |
| 16 | [tetrazole with N-(CH2)3-OH] | 303–305 | C₁₂H₁₀Cl₂N₆O₃·H₂O |
| 17 | [tetrazole with N-CH2CH2-OH] | 219–221 | C₁₁H₈Cl₂N₆O₃ |
| 18 | [triazole with N-CH2CH2-OH] | >300 | C₁₂H₉Cl₂N₅O₃·H₂O |
| 19 | [triazole with N-CH3] | >300 | C₁₁H₇Cl₂N₅O₂·0.5H₂O |
| 20 | [triazole with N-CH3] | >300 | C₁₁H₇Cl₂N₅O₂·H₂O |

TABLE 1-continued

| # | Structure | mp (°C) | Formula |
|---|---|---|---|
| 21 | (1-methyl-1,2,4-triazol-3-yl) | >300 | $C_{11}H_7Cl_2N_5O_2 \cdot 0.75H_2O$ |
| 22 | 5-methyl-3-(3-chlorophenyl)-1,2,4-triazol-4-yl | 272–274 | $C_{17}H_{10}Cl_3N_5O_2 \cdot HCl \cdot 2.5H_2O$ |
| 23 | 5-ethyl-3-(pyridin-3-yl)-1,2,4-triazol-4-yl | 268–270 | $C_{17}H_{12}Cl_2N_6O_2 \cdot 2HCl \cdot 0.5H_2O$ |
| 24 | 3-ethyl-5-methyl-1,2,4-triazol-4-yl | >315 | $C_{13}H_{11}Cl_2N_5O_2$ |
| 25 | 5-ethyl-3-(2-methoxyphenyl)-1,2,4-triazol-4-yl | 236–237 | $C_{19}H_{15}Cl_2N_5O_3 \cdot HCl \cdot 0.55H_2O$ |
| 26 | 5-ethyl-3-(2-chlorophenyl)-1,2,4-triazol-4-yl | 264 (decomp.) | $C_{18}H_{12}Cl_3N_5O_2 \cdot HCl \cdot 0.5H_2O \cdot 0.25$ diisopropyl ether |
| 27 | 5-ethyl-1,2,4-triazol-4-yl | >315 | $C_{12}H_9Cl_2N_5O_2 \cdot HCl \cdot 0.95H_2O$ |
| 28 | 5-ethyl-3-(1-methylpyrazol-5-yl)-1,2,4-triazol-4-yl | >300 | $C_{16}H_{13}Cl_2N_7O_2$ |
| 29 | 5-ethyl-3-(dimethylaminomethyl)-1,2,4-triazol-4-yl | solid foam | $C_{15}H_{16}Cl_2N_6O_2 \cdot HCl \cdot 5H_2O \cdot 0.2CH_2Cl_2$ |
| 30 | 5-ethyl-3-(morpholinomethyl)-1,2,4-triazol-4-yl | 273–276 | $C_{17}H_{18}Cl_2N_6O_3 \cdot 2HCl \cdot 2.5H_2O$ |

TABLE 1-continued

| No. | Structure | mp (°C) | Formula |
|---|---|---|---|
| 31 | (5-methyl-triazole, 4-pyridyl) | 284 (decomp.) | $C_{16}H_{10}Cl_2N_6O_2 \cdot 2HCl \cdot 3H_2O$ |
| 32 | (5-methyl-triazole, 2-pyridyl) | >300 | $C_{16}H_{10}Cl_2N_6O_2 \cdot H_2O$ |
| 33 | (5-methyl-triazole, 2-pyrazinyl) | >300 | $C_{15}H_9Cl_2N_7O_2 \cdot 2H_2O$ |
| 34 | (5-methyl-triazole, 2-pyrimidinyl) | >300 | $C_{15}H_9Cl_2N_7O_2 \cdot 1.4H_2O$ |
| 35 | (5-methyl-triazole, 3-pyridyl) | >300 | $C_{16}H_{10}Cl_2N_6O_2 \cdot HCl \cdot 0.33H_2O$ |
| 36 | (5-methyl-triazole, 2-methyl-thiazol-4-yl) | 279–282 | $C_{15}H_{10}Cl_2N_6O_2S \cdot 0.1MeOH \cdot 0.04$ 1,4-dioxane $\cdot HCl \cdot H_2O$ |
| 37 | (5-methyl-triazole, 1-methyl-pyrrol-2-yl) | 252–256 (decomp.) | $C_{16}H_{12}Cl_2N_6O_2$ |
| 38 | (5-methyl-triazole, 4-pyridazinyl) | 284–292 (decomp.) | $C_{15}H_9Cl_2N_7O_2 \cdot 0.3$ 1,4-dioxane $\cdot 4.5H_2O$ |
| 39 | (5-methyl-triazole, 3-methyl-isothiazol-4-yl) | 263–265 (decomp.) | $C_{15}H_{10}Cl_2N_6O_2S$ |
| 40 | (5-methyl-triazole, 2-pyridylmethyl) | 286 | $C_{17}H_{12}Cl_2N_6O_2$ |

TABLE 1-continued

| # | Structure | mp (°C) | Formula |
|---|---|---|---|
| 41 | 3-methyl-5-(pyridin-3-ylmethyl)-4H-1,2,4-triazole N-oxide | 280 | $C_{17}H_{12}Cl_2N_6O_2 \cdot 2HCl \cdot 3.75H_2O$ |
| 42 | 3-methyl-5-(pyridin-4-ylmethyl)-4H-1,2,4-triazole N-oxide | 297 | $C_{17}H_{12}Cl_2N_6O_2 \cdot 2HCl \cdot 3H_2O$ |
| 43 | 3-methyl-5-(5-methyl-1H-pyrazol-3-yl)-4H-1,2,4-triazole N-oxide | >300 | $C_{15}H_{11}Cl_2N_7O_2$ |
| 44 | 3-methyl-5-(4-methyl-1,2,3-thiadiazol-5-yl)-4H-1,2,4-triazole N-oxide | >300 | $C_{14}H_9Cl_2N_7O_2S \cdot HCl \cdot 1.5H_2O$ |
| 45 | 3-methyl-5-(2-chlorophenyl)-4H-1,2,4-triazole N-oxide | 290–294 | $C_{17}H_{10}Cl_3N_5O_2$ |
| 46 | 3-methyl-5-(2-methylphenyl)-4H-1,2,4-triazole N-oxide | solid foam | $C_{18}H_{13}Cl_2N_5O_2$ |
| 47 | 3-methyl-5-(2-methylpyridin-3-yl)-4H-1,2,4-triazole N-oxide | 290–293 | $C_{17}H_{12}Cl_2N_6O_2 \cdot HCl \cdot 3.5H_2O$ |
| 48 | 3-methyl-5-(2-methoxyphenyl)-4H-1,2,4-triazole N-oxide | 274–277 | $C_{18}H_{13}Cl_2N_5O_3$ |
| 49 | 3-methyl-5-(4-methyl-1H-imidazol-5-yl)-4H-1,2,4-triazole N-oxide | solid foam | $C_{15}H_{11}Cl_2N_7O_2$ |

TABLE 1-continued

| # | Structure | mp (°C) | Formula |
|---|---|---|---|
| 50 | 5-methyl-3-(6-methylpyridin-3-yl)-4H-1,2,4-triazole N-oxide | 273–279 | $C_{17}H_{12}Cl_2N_6O_2 \cdot HCl \cdot 2H_2O$ |
| 51 | 5-methyl-3-(3-methoxyphenyl)-4H-1,2,4-triazole N-oxide | 285–286 | $C_{18}H_{13}Cl_2N_5O_3 \cdot HCl \cdot 2H_2O$ |
| 52 | 5-methyl-3-(1,5-dimethylpyrazol-3-yl)-4H-1,2,4-triazole N-oxide | 218 (decomp.) | $C_{16}H_{13}Cl_2N_7O_2$ |
| 53 | 5-methyl-3-(4-trifluoromethylphenyl)-4H-1,2,4-triazole N-oxide | >300 | $C_{18}H_{10}N_5O_2Cl_2F_3 \cdot HCl \cdot 0.4H_2O$ |
| 54 | 5-methyl-3-(5-propylpyrazol-3-yl)-4H-1,2,4-triazole N-oxide | 274–278 | $C_{17}H_{15}N_7O_2Cl_2$ |
| 55 | 5-methyl-3-(4-dimethylaminophenyl)-4H-1,2,4-triazole N-oxide | >300 | $C_{19}H_{16}Cl_2N_6O_2 \cdot 2HCl \cdot 0.75H_2O$ |
| 56 | 5-methyl-3-(1-methylpyrazol-4-yl)-4H-1,2,4-triazole N-oxide | >300 | $C_{15}H_{11}Cl_2N_7O_2 \cdot HCl \cdot 0.25H_2O$ |
| 57 | 5-methyl-3-(3-methylpyrazol-4-yl)-4H-1,2,4-triazole N-oxide | 272–275 | $C_{15}H_{11}Cl_2N_7O_2 \cdot 2HCl \cdot 2.75H_2O$ |
| 58 | 5-methyl-3-(1-methylimidazol-4-yl)-4H-1,2,4-triazole N-oxide | >300 | $C_{15}H_{11}Cl_2N_7O_2 \cdot 2HCl \cdot 2H_2O$ |
| 59 | 5-methyl-3-(1H-1,2,3-triazol-5-yl)-4H-1,2,4-triazole N-oxide | >300 | $C_{13}H_8Cl_2N_8O_2 \cdot 2HCl \cdot 2H_2O$ |

TABLE 1-continued

| No. | Structure | mp (°C) | Formula |
|---|---|---|---|
| 60 | (structure) | >300 | $C_{15}H_{11}Cl_2N_7O_2 \cdot HCl \cdot 0.33$ 1,4-dioxane $\cdot H_2O$ |
| 61 | (structure) | 257 (decomp.) | $C_{18}H_{12}Cl_3N_5O_4S \cdot HCl \cdot 0.13$ 1,4-dioxane $\cdot H_2O$ |
| 62 | (structure) | >300 | $C_{15}H_{11}Cl_2N_7O_2 \cdot HCl \cdot 1.5H_2O$ |
| 63 | (structure) | >300 | $C_{14}H_{10}Cl_2N_8O_2 \cdot HCl \cdot H_2O$ |
| 64 | (structure) | >300 | $C_{13}H_8Cl_2N_8O_3 \cdot 3H_2O$ |
| 65 | (structure) | >300 | $C_{14}H_9Cl_2N_7O_2 \cdot HCl \cdot 0.5H_2O \cdot 0.5$ 1,4-dioxane |
| 66 | (structure) | >300 | $C_{15}H_9Cl_2N_5O_2S \cdot HCl$ |
| 67 | (structure) | 273–275 (decomp) | $C_{17}H_{11}Cl_2N_5O_3 \cdot HCl \cdot 0.25H_2O$ |
| 68 | (structure) | >300 | $C_{17}H_{10}Cl_3N_5O_2 \cdot HCl \cdot 0.5H_2O$ |
| 69 | (structure) | 282–284 (decomp) | $C_{18}H_{13}Cl_2N_5O_3 \cdot HCl \cdot 0.4H_2O$ |

TABLE 1-continued

| # | Structure | mp (°C) | Formula |
|---|---|---|---|
| 70 | (3,5-dimethyl-4H-1,2,4-triazol-4-yl N-oxide) | >310 | $C_{12}H_9Cl_2N_5O_2$ |
| 71 | (3-methyl-4H-1,2,4-triazol-4-yl N-oxide) | >310 | $C_{11}H_7Cl_2N_5O_2 \cdot HCl \cdot 0.4H_2O$ |
| 72 | (3-methyl-5-cyclopropyl-4H-1,2,4-triazol-4-yl N-oxide) | 260 (decomp) | $C_{14}H_{11}Cl_2N_5O_2 \cdot HCl \cdot 0.5H_2O$ |
| 73 | (3-methyl-5-phenyl-4H-1,2,4-triazol-4-yl N-oxide) | 274–276 | $C_{17}H_{11}Cl_2N_5O_2 \cdot HCl \cdot 1.2H_2O$ |
| 74 | (3-methyl-5-hydroxy-4H-1,2,4-triazol-4-yl N-oxide) | >310 | $C_{11}H_7Cl_2N_5O_3$ |
| 75 | (3-methoxymethyl-5-(1,5-dimethylpyrazol-3-yl)-4H-1,2,4-triazol-4-yl N-oxide) | solid foam | $C_{17}H_{15}Cl_2N_7O_3 \cdot 0.1\ 1,4\text{-dioxane} \cdot 1.75H_2O$ |
| 76 | (3-methoxymethyl-5-(2-chlorophenyl)-4H-1,2,4-triazol-4-yl N-oxide) | 175 (decomp) | $C_{18}H_{12}Cl_3N_5O_3$ |
| 77 | (3-methoxymethyl-5-(pyridin-3-ylmethyl)-4H-1,2,4-triazol-4-yl N-oxide) | 241 (decomp) | $C_{18}H_{14}Cl_2N_6O_3 \cdot 2HCl \cdot 2H_2O$ |
| 78 | (3-methoxymethyl-5-(6-methylpyridin-3-yl)-4H-1,2,4-triazol-4-yl N-oxide) | 234 | $C_{18}H_{14}Cl_2N_6O_3 \cdot 2HCl \cdot 2H_2O \cdot 0.4\ 1,4\text{-dioxane} \cdot 0.2\ \text{diethyl ether}$ |
| 79 | (3-methoxymethyl-5-(1-methylpyrazol-5-yl)-4H-1,2,4-triazol-4-yl N-oxide) | 200 (decomp) | $C_{16}H_{13}Cl_2N_7O_3$ |

TABLE 1-continued

| | | | |
|---|---|---|---|
| 80 | 3,5-bis(methoxymethyl)-4H-1,2,4-triazole structure | 302–304 | $C_{14}H_{13}Cl_2N_5O_4$ |
| 81 | 3-(methoxymethyl)-5-(2-methylthiazol-5-yl)-4H-1,2,4-triazole structure | 210–212 | $C_{16}H_{12}Cl_2N_6O_3S$ |
| 82 | 3-(methoxymethyl)-5-(6-carboxypyridin-3-yl)-4H-1,2,4-triazole structure | 253–254 | $C_{18}H_{12}Cl_2N_6O_5 \cdot$ HCl. $2H_2O$ |
| 83 | 3-(2-methoxyethyl)-5-(pyridin-3-yl)-4H-1,2,4-triazole structure | >306 | $C_{18}H_{14}Cl_2N_6O_3 \cdot$ 2HCl. $H_2O$ |
| 84 | 3-(3-carboxypropyl)-5-(pyridin-3-yl)-4H-1,2,4-triazole structure | >305 | $C_{19}H_{14}Cl_2N_6O_4 \cdot$ HCl |
| 85 | 3-(ethoxycarbonyl)-4H-1,2,4-triazole structure | >300 | $C_{13}H_9Cl_2N_5O_4 \cdot$ $H_2O$ |
| 86 | 3,5-diphenyl-4H-1,2,4-triazole structure | >305 | $C_{22}H_{13}Cl_2N_5O_2 \cdot$ $H_2O$. 1,4-dioxane |
| 87 | 3-(3-methyl-1,2,4-oxadiazol-5-yl)-5-(pyridin-3-yl)-4H-1,2,4-triazole structure | 268–270 | $C_{18}H_{10}Cl_2N_8O_3 \cdot$ HCl. $1.5H_2O$ |
| 88 | 3-methyl-5-(3-methyl-1,2,4-oxadiazol-5-yl)-4H-1,2,4-triazole structure | 225–228 | $C_{14}H_9Cl_2N_7O_3 \cdot$ HCl. $H_2O$ |
| 89 | 3-(pyridin-3-yl)-4H-1,2,4-triazole structure | 277–279 | $C_{15}H_8Cl_2N_6O_2 \cdot$ HCl. $2H_2O$ |

TABLE 1-continued

| | Structure | mp (°C) | Formula |
|---|---|---|---|
| 90 | (5-bromo-3-(pyridin-3-yl)-4H-1,2,4-triazol-4-yl) | >330 | $C_{15}H_7BrCl_2N_6O_2 \cdot 2.5H_2O$ |
| 91 | (5-methyl-3-(1H-imidazol-1-yl)-4H-1,2,4-triazol-4-yl) | 197–199 (decomp) | $C_{14}H_9Cl_2N_7O_2$ |
| 92 | (5-(hydroxymethyl)-3-(pyridin-3-yl)-4H-1,2,4-triazol-4-yl) | 284–285 | $C_{16}H_{10}Cl_2N_6O_3 \cdot HCl \cdot 3.5H_2O$ |
| 93 | (5-methyl-3-(hydroxymethyl)-4H-1,2,4-triazol-4-yl) | >315 | $C_{12}H_9Cl_2N_5O_3$ |
| 94 | (5-((dimethylamino)methyl)-3-(pyridin-3-yl)-4H-1,2,4-triazol-4-yl) | 264–265 | $C_{18}H_{15}Cl_2N_7O_2 \cdot 2HCl \cdot 2H_2O$ |
| 95 | (5-(morpholinomethyl)-3-(pyridin-3-yl)-4H-1,2,4-triazol-4-yl) | 268–270 | $C_{20}H_{17}Cl_2N_7O_3 \cdot 2HCl \cdot 2H_2O$ |
| 96 | (5-(hydroxymethyl)-3-phenyl-4H-1,2,4-triazol-4-yl) | 260 (decomp) | $C_{17}H_{11}Cl_2N_5O_3 \cdot 0.5H_2O$ |
| 97 | (5-(hydroxymethyl)-4H-1,2,4-triazol-4-yl) | >300 | $C_{11}H_7Cl_2N_5O_3 \cdot H_2O$ |
| 98 | (5-methyl-3-(2-hydroxyethyl)-4H-1,2,4-triazol-4-yl) | >300 | $C_{13}H_{11}Cl_2N_5O_3$ |
| 99 | (pyridin-3-yl) | >300 | $C_{13}H_7Cl_2N_3O_2 \cdot HCl \cdot 2H_2O$ |

TABLE 1-continued

| # | Structure | mp | Formula |
|---|---|---|---|
| 100 | 1H-triazole-phenyl | >300 | $C_{16}H_9Cl_2N_5O_2 \cdot H_2O$ |
| 101 | 2-CH₃-triazole-phenyl | >300 | $C_{17}H_{11}Cl_2N_5O_2 \cdot 0.75H_2O$ |
| 102 | 1-CH₃-triazole-phenyl | >300 | $C_{17}H_{11}Cl_2N_5O_2 \cdot 1.75H_2O$ |
| 103 | 1-CH₃-triazole-phenyl (isomer) | >300 | $C_{17}H_{11}Cl_2N_5O_2 \cdot 0.5H_2O$ |
| 104 | 2-(2-hydroxyethyl)-triazole-phenyl | >300 | $C_{18}H_{13}Cl_2N_5O_3 \cdot 0.75H_2O$ |
| 105 | 1-(2-hydroxyethyl)-triazole-phenyl | >300 | $C_{18}H_{13}Cl_2N_5O_3 \cdot HCl \cdot 0.33H_2O \cdot 0.1$ diethyl ether |
| 106 | 1-(2-hydroxyethyl)-triazole-phenyl (isomer) | >300 | $C_{18}H_{13}Cl_2N_5O_3$ |
| 107 | 5-methyl-4-(1H-triazol-5-yl)-triazole | 291–293 (decomp.) | $C_{13}H_8N_8O_2Cl_2 \cdot HCl \cdot H_2O$ |

TABLE 1-continued

| Ex. No. | Analytical Data:<br>Analysis (% Found (Required))<br>or ¹H-NMR (300 MHz, DMSO-$d_6$<br>(unless otherwise stated))<br>or LRMS (m/z) | Starting<br>material<br>Preparation<br>no. | Trituration<br>Solvent<br>(a) water<br>(b) diethyl ether<br>(c) methanol<br>(d) 1,4-dioxane<br>(e) ethyl acetate<br>(f) diisopropyl ether<br>(g) dichloromethane<br>(h) acetone |
|---|---|---|---|
| 2 | C, 49.74; H, 2.01; N, 12.93<br>(C, 49.80; H, 2.44; N, 13.40)<br>(thermospray) 308 (MH⁺). | 3 | a |
| 3 | C, 45.84; H, 1.86; N, 17.85<br>(C, 46.03; H, 2.09; N, 17.89)<br>δ = 7.40(1H, s), 7.57(1H, t, J=5Hz),<br>8.92(2H, d, J=5Hz), 11.25(1H, s),<br>12.1(1H, s). | 4 | a then b |
| 4 | δ = 7.40(1H, s), 8.72(2H, s), 9.28<br>(1H, s), 11.33(1H, s), 12.12(1H, s).<br>(thermospray) 326 (MNH₄⁺). | 5 | note 1 |
| 5 | C, 39.42; H, 2.40; N, 25.08<br>(C, 39.05; H, 2.17; N, 24.78)<br>δ = 3.80(3H, s), 7.50(1H, s), 11.64<br>(1H, br, s), 12.26(1H, br, s). | 8 | a, b |
| 6 | δ = 1.24(3H, m), 1.60(1H,<br>m), 1.78(4H, m), 2.00(2H,<br>m), 4.08(1H, m), 7.50(1H, s),<br>11.70(1H, br s), 12.16<br>(1H, br s).<br>(thermospray) 381 (MH⁺). | 9 | a |
| 7 | δ = 3.10(2H, m), 4.42(2H,<br>m), 7.18(5H, m), 7.46(1H, s),<br>11.58(1H, br s), 12.14<br>(1H, br s).<br>(thermospray) 403 (MH⁺). | 10 | a |
| 8 | C, 35.64; H, 2.02; N, 21.74<br>(C, 35.66; H, 2.31; N, 21.89) | 11 | a |
| 9 | C, 41.68; H, 2.62; N, 23.67<br>(C, 41.69; H, 2.94; N, 23.88)<br>δ = 1.48(6H, d, J=8Hz), 4.94<br>(1H, m), 7.48(1H, s), 11.78<br>(1H, br, s), 12.24(1H, br, s). | 12 | a |
| 10 | C, 41.19; H, 2.62; N, 23.67<br>(C, 41.28; H, 3.06; N, 24.31)<br>(thermospray) 327 (MH⁺). | 13 | a |
| 11 | δ = 5.46(2H, m), 7.10(2H, m),<br>7.20(3H, m), 7.42(1H, s), 11.66<br>(1H, br s), 12.16(1H, br s).<br>(thermospray) 389 (MH⁺). | 14 | a |
| 12 | C, 40.62; H, 3.01; N, 22.70<br>(C, 40.70; H, 2.97; N, 22.96) | 15 | a |
| 13 | δ = 7.42(1H, s), 7.50(5H, m),<br>11.86(1H, br s), 12.16<br>(1H, br s).<br>(thermospray) 375 (MH⁺). | 16 | a |
| 14 | δ = 5.38(1H, m), 5.62(1H, m),<br>7.50(1H, s), 11.90(1H, br.s),<br>12.24(1H, br.s).<br>(thermospray) 398 (MNH₄⁺). | 17 | a |
| 15 | δ = 4.88(2H, d, J=8Hz), 5.20<br>(2H, m), 5.88(1H, m), 7.50<br>(1H, s), 11.66(1H, br s), 12.16<br>(1H, br s).<br>(thermospray) 339 (MH⁺). | 19 | a |
| 16 | C, 38.73; H, 3.43; N, 22.64<br>(C, 38.41; H, 3.22; N, 22.40) | 20 | a |
| 17 | δ = 3.70(2H, m), 4.14(1H, m),<br>4.34(1H, m), 4.76(1H, m), 7.48<br>(1H, s), 11.38(1H, br.s), 12.16<br>(1H, br.s).<br>(thermospray) 343 (MH⁺). | 21 | a |
| 18 | C, 39.77; H, 3.06; N, 19.08<br>(C, 40.02; H, 3.08; N, 19.45)<br>(thermospray) 342 (MH⁺). | 22 | f, note 2 |
| 19 | C, 41.00; H, 2.78; N, 21.56<br>(C, 41.14; H, 2.51; N, 21.81)<br>δ = 3.42(3H, s), 7.46(1H, s), 8.67 | 23 | a |

TABLE 1-continued

| | | | |
|---|---|---|---|
| | (1H, s), 11.33(1H, br, s), 12.15 (1H, br, s). | | |
| 20 | C, 39.76; H, 2.62; N, 21.27 (C, 40.02; H, 2.75; N, 21.21) δ = 3.67(3H, s), 7.46(1H, s), 8.13 (1H, s), 11.48(1H, br, s), 12.16 (1H, br, s). | 25 isomer 1 | a |
| 21 | C, 40.55; H, 2.32; N, 21.57 (C, 40.57; H, 2.63; N, 21.51) δ = 3.97(3H, s), 7.40(1H, s), 8.71 (1H, s), 11.14(1H, br, s), 12.08 (1H, br, s). | 25 isomer 2 | a |
| 22 | C, 40.68; H, 3.17; N, 13.96 (C, 40.50; H, 3.20; N, 13.89) | 27 | b |
| 23 | C, 42.06; H, 3.16; N, 17.10 (C, 42.09; H, 3.12; N, 17.32) | 28 | b |
| 24 | δ ($CD_3OD$) = 1.37(3H, t, J=7Hz), 2.50(3H, s), 1.43(2H, q, J=7Hz), 6.35(1H, s). (thermospray) 340 ($MH^+$). | 29 | b |
| 25 | C, 47.71; H, 3.46; N, 14.48 (C, 47.68; H, 3.60; N, 14.63) | 30 | b, c, e |
| 26 | C, 46.08; H, 3.50; N, 13.79 (C, 46.13; H, 3.47; N, 13.79) | 31 | c, f |
| 27 | C, 37.93; H, 3.17; N, 18.19 (C, 37.96; H, 3.16; N, 18.44) (thermospray) 326 ($MH^+$). | 32 | b, c |
| 28 | δ = 1.18(3H, t, J=8Hz), 2.47(2H, m, obscured), 4.18(3H, s), 5.85 (1H, s), 7.34(1H, s), 7.43 (1H, s), 12.14(2H, br s). (thermospray) 405.5 ($MH^+$). | 33 | b |
| 29 | C, 34.45; H, 3.40; N, 15.55 (C, 34.66; H, 3.24; N, 15.95) (thermospray) 383 ($MH^+$). | 34 | b |
| 30 | C, 37.68; H, 4.24; N, 15.31 (C, 37.59; H, 4.64; N, 15.47) | 35 | b |
| 31 | C, 37.39; H, 3.37; N, 16.50 (C, 37.23; H, 3.52; N, 16.28) | 36 | a |
| 32 | C, 47.03; H, 3.11; N, 20.34 (C, 47.19; H, 2.97; N, 20.64) (thermospray) 389 ($MH^+$). | 37 | a |
| 33 | C, 42.28; H, 2.70; N, 22.69 (C, 42.27; H, 3.07; N, 23.00) (thermospray) 390 ($MH^+$). | 38 | a, b |
| 34 | C, 43.40; H, 2.57; N, 23.28 (C, 43.37; H, 2.86; N, 23.60) (thermospray) 390 ($MH^+$). | 39 | a, b |
| 35 | C, 44.58; H, 2.79; N, 19.55 (C, 44.52; H, 2.72; N, 19.47) (thermospray) 389 ($MH^+$). | 40 | a |
| 36 | C, 39.18; H, 2.98; N, 17.75 (C, 38.96; H, 2.94; N, 17.86) | 41 | b, c, d |
| 37 | δ = 2.10(3H, s), 3.88(3H, s), 5.64(1H, m), 5.87(1H, m), 6.88 (1H, m), 7.43(1H, s), 12.10(1H, s), 12.15(1H, s). (thermospray) 391 ($MH^+$). | 42 | a, c |
| 38 | C, 39.16; H, 3.90; N, 19.61 (C, 39.10; H, 4.12; N, 19.70) | 43 | a |
| 39 | δ = 2.15(3H, s), 2.65(3H, s), 7.40(1H, s), 8.59(1H, s), 12.12 (1H, s), 12.23(1H, s). (thermospray) 409 ($MH^+$). | 44 | a, c |
| 40 | δ = 2.17(3H, s), 4.20(2H, s), 7.39(3H, m), 7.46(1H, s), 7.87 (1H, t, J=4Hz), 8.44(1H, s), 12.22(1H, s). (thermospray) 403.4 ($MH^+$). | 45 | b |
| 41 | C, 37.85; H, 3.81; N, 15.20 (C, 37.55; H, 3.99; N, 15.46) | 46 | b |
| 42 | C, 38.60; H, 3.79; N, 15.51 (C, 38.51; H, 3.80; N, 15.85) | 47 | b |
| 43 | δ = 2.17(3H, s), 2.18(3H, s), 6.41(1H, s), 7.47(1H, s), 12.21 (2H, br s). (thermospray) 292.0 ($MH^+$). | 48 | b |

TABLE 1-continued

| | | | |
|---|---|---|---|
| 44 | C, 35.90; H, 2.64; N, 20.59 (C, 35.91; H, 2.67; N, 20.94) (thermospray) 409 (MH⁺). | 49 | b |
| 45 | δ = 2.19(3H, s), 7.21(2H, m), 7.38(1H, s), 7.40(1H, d, J=4Hz), 7.50(1H, d, J=4Hz), 12.10(2H, br s). (thermospray) 421.6 (MH⁺). | 50 | b |
| 46 | δ = 2.19(3H, s), 2.41(3H, s), 6.98(1H, d, J=4Hz), 7.22(2H, m), 7.39(1H, s), 7.07(1H, m), 12.14(1H, s), 12.30(1H, s). (thermospray) 402 (MH⁺). | 51 | b |
| 47 | C, 38.20; H, 3.72; N, 15.09 (C, 37.87; H, 3.93; N, 15.59) | 52 | b |
| 48 | δ = 2.21(3H, s), 3.42(3H, s), 6.97(2H, m), 7.41(3H, m), 12.19(1H, s), 12.20(1H, s). (thermospray) 418.2 (MH⁺). | 53 | b |
| 49 | δ = 2.17(3H, s), 2.40(3H, s), 7.49(1H, s), 7.74(1H, s), 12.26 (2H, br s). (thermospray) 391.9 (MH⁺). | 54 | b |
| 50 | C, 42.78; H, 4.02; N, 18.13 (C, 42.92; H, 3.60; N, 17.67) | 55 | b |
| 51 | C, 44.28; H, 3.44; N, 13.87 (C, 44.06; H, 3.70; N, 14.27) | 56 | b |
| 52 | δ = 2.00(3H, s), 2.12(3H, s), 4.00(3H, s), 5.66(1H, s), 7.48 (1H, s), 12.15(2H, br.s). (thermospray) 406.4 (MH⁺). | 57 | f |
| 53 | C, 43.58; H, 2.78; N, 13.80 (C, 43.25; H, 2.38; N, 14.01) (thermospray) 456 (MH⁺). | 58 | b |
| 54 | δ = 0.83(3H, t, J=8Hz), 1.55(2H, m), 2.15(3H, s), 2.50(2H, t, obscured), 6.45(1H, s), 7.48 (1H, s), 12.10(1H, s), 12.20 (1H, s). (thermospray) 420.2 (MH⁺). | 59 | b |
| 55 | C, 41.49; H, 3.96; N, 15.08 (C, 41.21; H, 4.28; N, 15.18) (thermospray) 431 (MH⁺). | 60 | b |
| 56 | C, 41.50; H, 2.87; N, 22.26 (C, 41.59; H, 2.91; N, 22.63) (thermospray) 392 (MH⁺). | 61 | b |
| 57 | C, 35.12; H, 3.66; N, 18.98 (C, 35.01; H, 3.62; N, 19.05) | 62 | b |
| 58 | C, 36.08; H, 3.31; N, 19.59 (C, 35.95; H, 3.42; N, 19.56) (APCI) 392 (MH⁺). | 63 | b |
| 59 | C, 34.66; H, 2.86; N, 22.31 (C, 34.46; H, 2.96; N, 22.45) (thermospray) 379 (MH⁺). | 64 | b |
| 60 | C, 38.90; H, 3.22; N, 20.65 (C, 38.62; H, 3.50; N, 21.02) (thermospray) 392 (MH⁺). | 65 | b |
| 61 | C, 39.01; H, 2.91; N, 12.20 (C, 39.25; H, 2.85; N, 12.36) | 66 | b |
| 62 | C, 39.25; H, 3.13; N, 21.20 (C, 39.54; H, 3.32; N, 21.52) (thermospray) 392 (MH⁺). | 69 | b |
| 63 | C, 37.76; H, 2.70; N, 25.17 (C, 37.56; H, 2.93; N, 25.03) (thermospray) 393 (MH⁺). | 70 | b |
| 64 | C, 34.66; H, 2.96; N, 24.63 (C, 34.76; H, 3.14; N, 24.94) δ = 2.16(3H, s), 7.44(1H, s), 7.92(1H, br, s), 10.36(1H, br, s), 11.97(1H, br, s), 12.18 (1H, br, s). | 71 | b |
| 65 | C, 41.18; H, 3.03; N, 21.37 (C, 41.09; H, 3.23; N, 20.96) δ = 2.12(3H, s), 7.57(1H, s), 7.78(2H, s), 12.12(1H, br, s), 12.22(1H, br, s). | 72 | d, b |
| 66 | C, 42.32; H, 2.54; N, 16.05 (C, 41.83; H, 2.34; N, 16.26) δ = 2.12(3H, s), 6.90(1H, d, | 73 | a |

TABLE 1-continued

| | | | |
|---|---|---|---|
| | J=4Hz), 6.95(1H, m), 7.50 (1H, s), 7.62(1H, d, J=4Hz), 12.35(1H, s), 12.37(1H, s). | | |
| 67 | C, 45.79; H, 2.78; N, 15.66 (C, 45.87; H, 2.83; N, 15.73) | 74 | a, h |
| 68 | C, 43.45; H, 2.34; N, 14.98 (C, 43.62; H, 2.58; N, 14.96) (thermospray) 422 (MH$^+$). | 75 | a, h |
| 69 | C, 47.11; H, 2.85; N, 14.78 (C, 46.81; H, 3.23; N, 15.16) | 76 | a, c, h |
| 70 | δ = 2.21(6H, s), 7.54(1H, s), 12.04(1H, s), 12.33(1H, s). (thermospray) 326 (MH$^+$). | 77 | c |
| 71 | C, 36.90; H, 2.74; N, 19.02 (C, 36.76; H, 2.58; N, 19.49) (thermospray) 312 (MH$^+$). | 78 | c, b |
| 72 | C, 42.41; H, 3.19; N, 17.76 (C, 42.29; H, 3.30; N, 17.61) | 79 | c |
| 73 | C, 46.12; H, 3.43; N, 15.22 (C, 45.75; H, 3.25; N, 15.69) | 80 | c |
| 74 | δ = 1.84(3H, s), 7.38(1H, s), 11.55(1H, s), 12.27(1H, s), 12.31(1H, s). (thermospray) 345 (MNH$_4^+$). | 81 | b, h |
| 75 | C, 44.26; H, 3.88; N, 20.27 (C, 43.85; H, 4.08; N, 20.57) (thermospray) 436 (MH$^+$). | 82 | b |
| 76 | δ = 3.15(3H, s), 4.40(2H, s), 7.40(5H, m), 12.10(1H, br s), 12.20(1H, br s). (thermospray) 452 (MH$^+$). | 83 | b |
| 77 | C, 39.86; H, 3.79; N, 15.62 (C, 39.87; H, 3.72; N, 15.50) | 84 | b |
| 78 | C, 41.24; H, 4.31; N, 13.98 (C, 41.51; H, 4.30; N, 14.24) (APCI) 433 (MH$^+$). | 85 | b |
| 79 | δ = 3.18(3H, s), 4.16(3H, s), 4.40(2H, m), 5.96(1H, s), 7.38 (1H, s), 7.50(1H, s), 12.10(1H, br s), 12.6(1H, br s). (thermospray) 422 (MH$^+$). | 86 | g |
| 80 | δ = 3.10(6H, s), 4.30(4H, m), 7.42(1H, s), 11.84(1H, br s), 12.14(1H, br s). (APCI) 386 (MH$^+$). | 87 | b, c |
| 81 | δ = 2.42(3H, s), 3.14(3H, s), 4.34(2H, m), 7.48(1H, s), 7.90 (1H, s), 12.08(1H, br s), 12.20 (1H, br s). (thermospray) 439 (MH$^+$). | 88 | d |
| 82 | C, 40.21; H, 3.65; N, 15.58 (C, 40.36; H, 3.20; N, 15.69) | 89 | a, b |
| 83 | C, 41.02; H, 3.51; N, 15.78 (C, 41.24; H, 3.46; N, 16.03) (APCI) 433 (MH$^+$). | 90 | a |
| 84 | C, 45.51; H, 3.10; N, 16.50 (C, 45.85; H, 3.04; N, 16.89) (thermospray) 461 (MH$^+$). | 91 | a |
| 85 | C, 40.18; H, 2.86; N, 18.01 (C, 40.23; H, 2.86; N, 18.04) (thermospray) 370 (MH$^+$). | 92 | a |
| 86 | C, 56.30; H, 4.07; N, 12.16 (C, 56.11; H, 4.16; N, 12.59) (thermospray) 450 (MH$^+$). | 95 | a |
| 87 | C, 41.59; H, 2.74; N, 21.15 (C, 41.52; H, 2.71; N, 21.52) | 96 | a |
| 88 | C, 37.67; H, 2.76; N, 21.52 (C, 37.48; H, 2.70; N, 20.85) | 97 | b |
| 89 | C, 40.65; H, 2.81; N, 18.87 (C, 40.24; H, 2.92; N, 18.70) | 98 | a, b |
| 90 | C, 36.06; H, 2.53; N, 16.45 (C, 36.10; H, 2.42; N, 16.83) (thermospray) 453 (MH$^+$). | 99 | h |
| 91 | δ = 2.12(3H, s), 7.49(1H, s), 7.63(2H, s), 9.02(1H, s), 12.18(1H, br s), 14.25 (1H, br s). | 100 | no trituration |
| 92 | C, 38.84; H, 3.62; N, 16.27 (C, 38.77; H, 3.59; N, 16.65) | 101 | a, b |

TABLE 1-continued

| | | | |
|---|---|---|---|
| 93 | δ = 2.06(3H, s), 4.32(2H, m), 5.05(1H, br s), 7.43(1H, s), 11.93(1H, br s), 12.11(1H, br s). (thermospray) 342 (MH$^+$). | 102 | a |
| 94 | C, 40.11; H, 3.88; N, 18.43 (C, 39.94; H, 3.91; N, 18.11) | 103 | a, b |
| 95 | C, 41.70; H, 4.01; N, 16.69 (C, 41.32; H, 3.97; N, 16.81) | 104 | a, b |
| 96 | C, 49.51; H, 3.00; N, 16.80 (C, 49.41; H, 2.93; N, 16.95) | 105 | c |
| 97 | C, 38.10; H, 2.51; N, 20.53 (C, 38.17; H, 2.62; N, 20.23) (thermospray) 328 (MH$^+$). | 106 | a |
| 98 | δ = 2.25(3H, s), 2.69(2H, m), 3.63(2H, m), 7.58(1H, s), 11.90(1H, br s), 12.24 (1H, br s). (thermospray) 356 (MH$^+$). | 107 | note 3 |
| 99 | C, 41.21; H, 2.85; N, 10.90 (C, 41.02; H, 3.18; N, 11.04) δ = 7.48(1H, s), 8.02(1H, m), 8.30(1H, m), 8.84(1H, s), 8.96 (1H, m), 11.20(1H, br, s), 12.26 (1H, br, s). | 109 | a |
| 100 | C, 48.93; H, 2.78; N, 18.15 (C, 49.00; H, 2.83; N, 17.86) δ = 7.38(5H, m), 7.42(1H, s), 11.20(1H, br, s), 12.11 (1H, br, s), 15.34(1H, br, s). | 110 | a |
| 101 | C, 50.86; H, 3.06; N, 17.11 (C, 50.83; H, 3.14; N, 17.43) δ = 4.23(3H, s), 7.37(5H, m), 7.44(1H, s), 11.14(1H, br, s), 12.06(1H, br, s). | 111 isomer 1 | a |
| 102 | C, 48.70; H, 3.04; N, 16.51 (C, 48.65; H, 3.48; N, 16.68) δ = 3.79(3H, s), 7.31(3H, m), 7.42(2H, m), 7.55(1H, s), 11.54 (1H, br, s), 12.15(1H, br, s). | 111 isomer 2 | a |
| 103 | C, 51.55; H, 3.33; N, 16.02 (C, 51.62; H, 3.46; N, 16.43) δ = 4.00(3H, s), 7.39(6H, m), 11.00(1H, br, s), 12.01 (1H, br, s). | 111 isomer 3 | a |
| 104 | C, 50.07; H, 3.46; N, 15.79 (C, 50.08; H, 3.39; N, 16.22) δ = 3.98(2H, m), 4.53(2H, m), 4.80(1H, br, s), 7.37(6H, m), 10.93(1H, br, s), 12.04 (1H, br, s). | 112 isomer 1 | a |
| 105 | C, 47.13; H, 3.13; N, 14.78 (C, 47.21; H, 3.37; N, 14.96) δ = 3.65(2H, m), 4.01(1H, m), 4.16(1H, m), 7.27(3H, m), 7.41 (2H, m), 7.51(1H, s), 11.26 (1H, br, s), 12.14(1H, br, s). | 112 isomer 2 | a |
| 106 | δ = 3.84(2H, m), 4.33(2H, m), 7.36(5H, m), 8.21(1H, s), 10.82(1H, br s), 11.98 (1H, br s). (thermospray) 418 (MH$^+$). | 112 isomer 3 | a |
| 107 | C, 36.05; H, 2.55; N, 25.73 (C, 36.01; H, 2.56; N, 25.84). | Note 4 | b |

Notes

1) The reaction was carried out as described for Example 1 but at 50° C. for 9 hours. The crude product was purified by flash chromatography on silica gel eluting with 95:5, by volume, dichloromethane:methanol then 80:20:1, by volume, dichloromethane:methanol:acetic acid.
2) The solid obtained was dissolved in hot water (4 mL), cooled to 0° C. and collected by filtration.
3) The product was obtained as an orange oil which was dissolved in distilled water (4 mL) and freeze-dried.
4) The starting material was prepared by a similar method to that of Preparation 27 and the hydrazide intermediate by a similar method to that of Preparation 117.

EXAMPLE 108

6,7-Dichloro-5-(1-methoxycarbonylmethyltetrazol-5-yl)-2,3(1H,4H)-quinoxalinedione

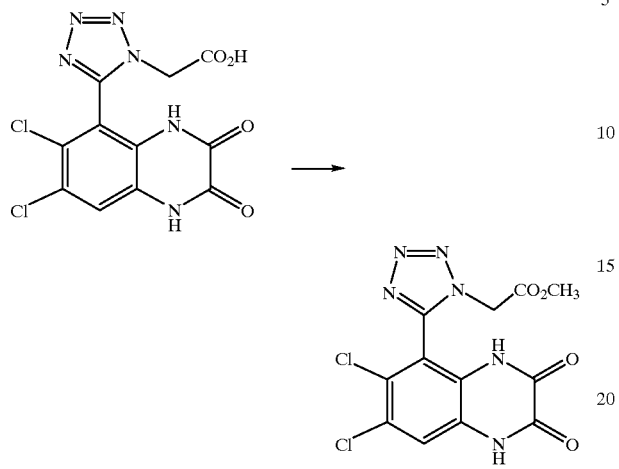

A solution of 6,7-dichloro-5-(1-carboxymethyltetrazol-5-yl)-2,3(1H,4H)-quinoxalinedione (Example 8, 42 mg, 0.12 mmol) in saturated methanolic hydrogen chloride (5 mL) was heated under reflux under nitrogen for 2 days. The reaction mixture was concentrated under reduced pressure and the residue partitioned between water (10 mL) and dichloromethane (10 mL). The aqueous phase was separated and extracted with dichloromethane (2×25 mL). The combined organic extracts were dried (MgSO$_4$) and concentrated under reduced pressure. The residue was triturated with diethyl ether and filtered to afford the title compound (24 mg, 55%) as a pale grey solid, mp 281–283° C.

$^1$H-NMR (300 MHz, DMSO-d$_6$): δ=3.60 (3H, s), 5.32 (2H, m), 7.44 (1H, s), 11.60 (1H, br s), 12.12 (1H, br s).

m/z (thermospray) 371 (MH$^+$).

EXAMPLE 109

6-Chloro-7-methyl-5-[5-methoxymethyl-3-(3-pyridyl)-4H-1,2,4-triazol-4-yl]-2,3(1H,4H)-quinoxalinedione

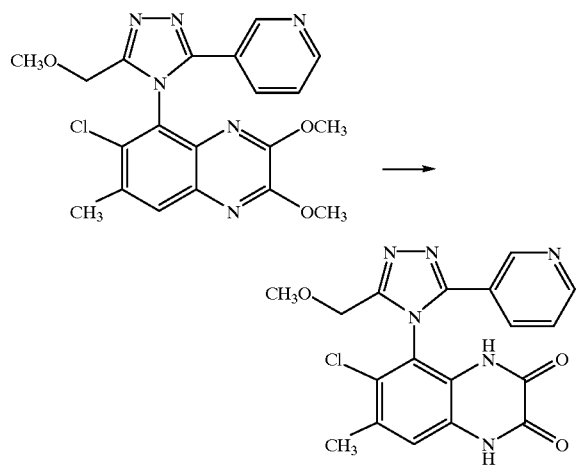

The title compound was prepared by a similar method to that of Example 1 using 6-chloro-2,3-dimethoxy-7-methyl-5-[5-methoxymethyl-3-(3-pyridyl)-4H-1,2,4-triazol-4-yl] quinoxaline (Preparation 114) in place of 6,7-dichloro-2,3-dimethoxy-5-(4-pyridyl)quinoxaline. The residue obtained on concentrating the reaction mixture was dissolved in 1M aqueous sodium hydroxide solution, the mixture was adjusted to pH 6 with 2M aqueous hydrochloric acid and cooled to 0° C. The solid formed was collected by filtration and washed with water to give an off-white solid, mp 229–231° C.

Analysis (%): Found: C, 51.33; H, 4.16; N, 19.99. C$_{18}$H$_{15}$ClN$_6$O$_3$. 0.25H$_2$O requires: C, 51.31; H, 4.19; N, 19.95.

EXAMPLE 110

7-Chloro-6-methyl-5-[5-methoxymethyl-3-(3-pyridyl)-4H-1,2,4-triazol-4-yl]-2,3(1H,4H)-quinoxalinedione

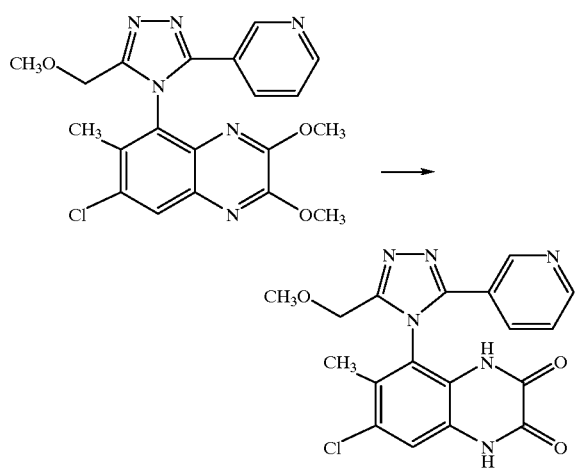

The title compound was prepared by the method of Example 1 using 7-chloro-2,3-dimethoxy-6-methyl-5-[5-methoxymethyl-3-(3-pyridyl)-4H-1,2,4-triazol-4-yl] quinoxaline (Preparation 115) in place of 6,7-dichloro-2,3-dimethoxy-5-(4-pyridyl)quinoxaline. The residue obtained on concentrating the reaction mixture was dissolved in 1M aqueous sodium hydroxide solution, the solution was adjusted to pH6 with 2M aqueous hydrochloric acid solution and cooled to 0° C. The solid formed was collected by filtration and washed with water to give a pale yellow solid, mp >300° C.

m/z (thermospray) 399 (MH$^+$).

Analysis (%): Found: C, 52.60; H, 3.91; N, 20.34. C$_{18}$H$_{15}$ClN$_6$O$_3$. 0.75H$_2$O requires: C, 52.43; H, 4.03; N, 20.38.

EXAMPLE 111

(±)-, (−)- and (+)-6,7-Dichloro-5-[3-methoxymethyl-5-(3-pyridyl)-4H-1,2,4-triazol-4-yl]-2,3(1H,4H)-quinoxalinedione

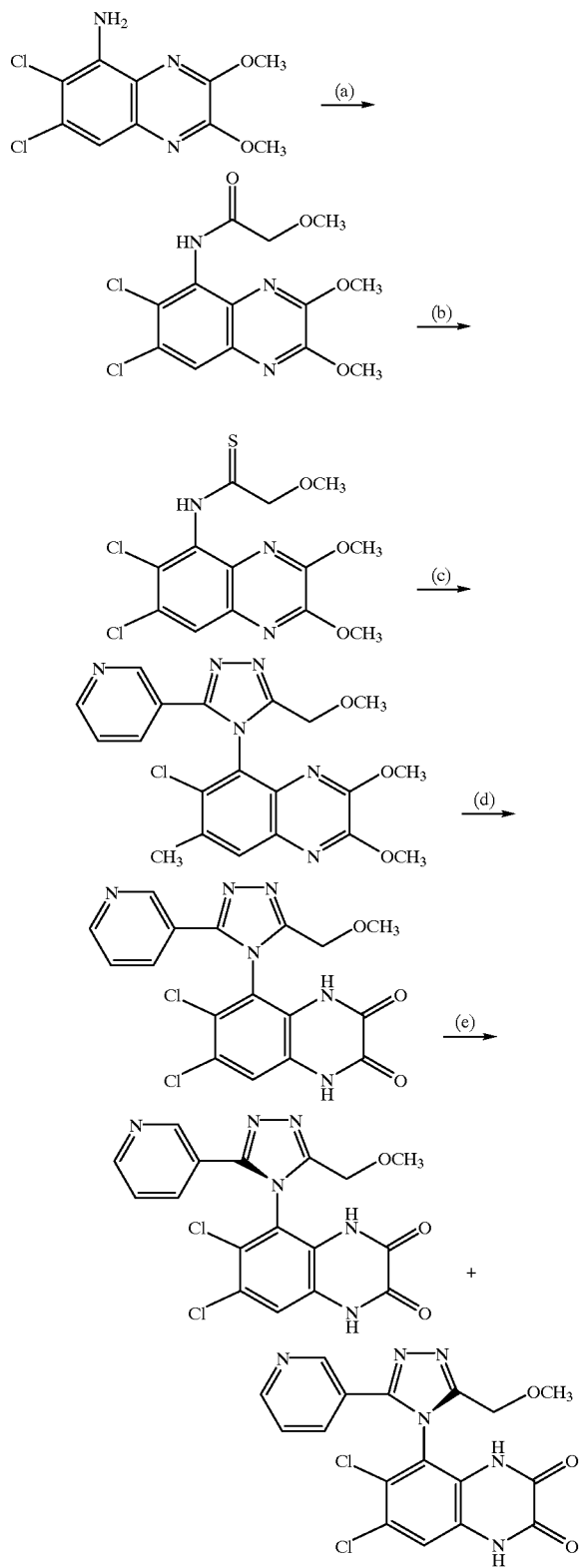

(a) Methoxyacetylchloride (27.3 mL, 32.4 g, 0.30 mol) was added to a stirred mixture of 5-amino-6,7-dichloro-2,3-dimethoxyquinoxaline (Preparation 26, 73.8 g, 0.27 mol) and pyridine (26.4 mL, 25.8 g, 0.33 mol) in dichloromethane (1.2L) at room temperature under nitrogen. After 18 hours stirring at room temperature, the mixture was washed with 2M aqueous hydrochloric acid solution followed by brine, then dried ($MgSO_4$) and concentrated under reduced pressure. The residue was triturated with methanol and filtered to give 6,7-dichloro-2,3-dimethoxy-5-methoxyacetamidoquinoxaline (82.0 g, 88%) as an off-white solid, mp 171–173° C.

Analysis (%): Found: C, 44.97; H, 3.75; N, 12.03. $C_{13}H_{13}Cl_2N_3O_4$ requires C, 45.11; H, 3.79; N, 12.14.

(b) 2,4-Bis(4-methoxyphenyl)-1,3-dithia-2,4-diphosphetane-2,4-disulphide (Lawesson's reagent) (19.5 g, 48.2 mmol) was added to a solution of 6,7-dichloro-2,3-dimethoxy-5-methoxyacetamidoquinoxaline (27 g, 78 mmol) in tetrahydrofuran (480 mL) and the mixture was stirred for 18 hours at room temperature, then evaporated under reduced pressure. The residue was purified by flash chromatography on silica gel, by gradient elution using hexane:dichloromethane (1:1 changing to 1:4, by volume) as the eluent to give 6,7-dichloro-2,3-dimethoxy-5-methoxythioacetamidoquinoxaline (29.1 g, >100%) as a white solid, mp 198–200° C., containing a minor impurity.

Analysis (%): Found: C, 43.06; H, 3.65; N, 11.59. $C_{13}H_{13}Cl_2N_3O_3S$ requires C, 43.11; H, 3.62; N, 11.60.

(c) A mixture of 6,7-dichloro-2,3-dimethoxy-5-methoxythioacetamidoquinoxaline (25.3 g, 69.9 mmol), nicotinic acid hydrazide (19.3 g, 140.8 mmol), mercury(II) oxide (15.1 g, 69.7 mmol) and 1,4-dioxane (600 mL) was heated under reflux for 18 hours. After cooling, the mixture was filtered through ARBOCEL (trade mark) filter aid and the residue washed with dichloromethane. The filtrate was concentrated under reduced pressure to afford a light brown solid which was partitioned between ethyl acetate and 2M aqueous hydrochloric acid solution. The layers were separated and the aqueous layer was extracted with dichloromethane (2×500 mL, 4×100 mL). The combined dichloromethane extracts were dried ($MgSO_4$) and concentrated under reduced pressure. The residue was crystallised from ethyl acetate/methanol to give (±)-6,7-dichloro-2,3-dimethoxy-5-[3-methoxymethyl-5-(3-pyridyl)-4H-1,2,4-triazol-4-yl)]quinoxaline (11.6 g, 37%) as a pale yellow solid, mp 189–191° C.

Analysis (%): Found: C, 50.10; H, 3.57; N, 18.53. $C_{19}H_{16}Cl_2N_6O_3$. $0.5H_2O$ requires: C, 50.01; H, 3.76; N, 18.42.

(d) A mixture of (±)-6,7-dichloro-2,3-dimethoxy-5-[3-methoxymethyl-5-(3-pyridyl)-4H-1,2,4-triazol-4-yl]quinoxaline (3.0 g, 6.7 mmol), 2M aqueous hydrochloric acid solution (10 mL) and 1,4-dioxane (50 mL) was heated under reflux for 9 hours, cooled, and concentrated under reduced pressure. The residue was dissolved in 1M aqueous sodium hydroxide solution and acidified to pH 4.5 with concentrated hydrochloric acid to afford a thick white precipitate. This was collected by filtration and washed with water to give (±)-6,7-dichloro-5-[3-methoxymethyl-5-(3-pyridyl)-4H-1,2,4-triazol-4-yl]-2,3(1H,4H)-quinoxalinedione (2.0 g, 68%) as an off-white solid, mp 230–232° C.

Analysis (%): Found: C, 46.23; H, 2.93; N, 19.00. $C_{17}H_{12}Cl_2N_6O_3$. $1.25H_2O$ requires: C, 46.22; H, 3.31; N, 19.02.

(e)(i) (−)-N-Methylephedrine (0.88 g, 4.9 mmol) and then methanol (66 mL) were added to a stirred suspension of (±)-6,7-dichloro-5-[3-methoxymethyl-5-(3-pyridyl)-4H-1,2,4-triazol-4-yl]-2,3(1H,4H)-quinoxalinedione (1.9 g, 4.3 mmol) in ethyl acetate (400 mL) at room temperature. The mixture was heated to its boiling point. The mixture was filtered, the filtrate concentrated to three quarters of its volume and then cooled to room temperature. The solid obtained was collected by filtrate and washed with ethyl acetate. The solid was crystallised from ethyl acetate/methanol to give a single diastereoisomer of the quinoxalinedione starting material as the (−)-N-methylephedrine salt (1.28 g, 43%), mp 162–164° C.

Analysis (%): Found: C, 55.74; H, 5.38; N, 14.38. $C_{28}H_{29}Cl_2N_7O_4 \cdot CH_3CO_2C_2H_5$ requires: C, 55.98; H, 5.43; N, 14.28.

$[\alpha]^{25}_D$ −135° (c=0.1, ethanol).

(ii) A suspension of the (−)-N-methylephedrine salt (1.2 g, 1.7 mmol) from part (e)(i) in water (13 mL) at room temperature was acidified to pH 5 with concentrated hydrochloric acid and the suspension was stirred for 1 hour. The solid obtained was collected by filtration, washed with water and crystallised from water/ethanol to give (−)-6,7-dichloro-5-[3-methoxymethyl-5-(3-pyridyl)-4H-1,2,4-triazol-4-yl]-2,3(1H,4H)-quinoxalinedione (0.48 g, 62%) as a white solid, mp 220–222° C.

Analysis (%): Found: C, 45.49; H, 3.21; N, 18.72. $C_{17}H_{12}Cl_2N_6O_3 \cdot 1.5H_2O$ requires C, 45.76; H, 3.39; N, 18.83.

$[\alpha]^{25}_D$ −214° (c=0.1, ethanol).

(iii) The combined filtrates from part (e)(i) were concentrated to dryness, the residue dissolved in water (20 mL), acidified to pH 3 with concentrated hydrochloric acid and the solid obtained was collected by filtration, washed with water and dried. (+)-N-Methylephedrine (0.37 g, 2.06 mmol) and then methanol (28 mL) were added to a stirred suspension of this solid (0.80 g, 1.87 mmol) in ethyl acetate (170 mL) at room temperature and the mixture was heated to its boiling point. The mixture was filtered, concentrated to three quarters of its volume and then cooled to room temperature. The solid obtained was collected by filtration and washed with ethyl acetate. The solid was crystallised from ethyl acetate/methanol to give a single diastereoisomer of the quinoxalinedione strating material as the (+)-N-methylephedrine salt (0.93 g, 32%) as a white solid, mp 165–167° C.

Analysis (%): Found: C, 55.88; H, 5.40; N, 14.31. $C_{28}H_{29}Cl_2N_7O_4 \cdot 0.8CH_3CO_2C_2H_5$ requires: C, 56.01; H, 5.33; N, 14.66.

$[\alpha]^{25}_D$ +127° (c=0.1, ethanol).

(iv) A suspension of the (+)-N-methylephedrine salt (0.90 g, 1.35 mmol) from part (e)(iii) in water (10 mL) at room temperature was acidified to pH 5 with concentrated hydrochloric acid and the suspension was stirred for 1 hour. The solid was collected by filtration and washed with water to give (+)-6,7-dichloro-5-[3-methoxymethyl-5-(3-pyridyl)-4H-1,2,4-triazol-4-yl]-2,3(1H,4H)-quinoxalinedione (0.41 g, 69%) as a white solid, mp 222–224° C.

Analysis (%): Found: C, 46.44; H, 3.18; N, 19.01. $C_{17}H_{12}Cl_2N_6O_3 \cdot 1.25H_2O$ requires C, 46.22; H, 3.31; N, 19.02.

$[\alpha]^{25}_D$ +212° (c=0.1, ethanol).

EXAMPLE 112

6-Chloro-7-ethyl-5-[3-methoxymethyl-5-(3-pyridyl)-4H-1,2,4-triazol-4-yl]-2,3(1H,4H)-quinoxalinedione

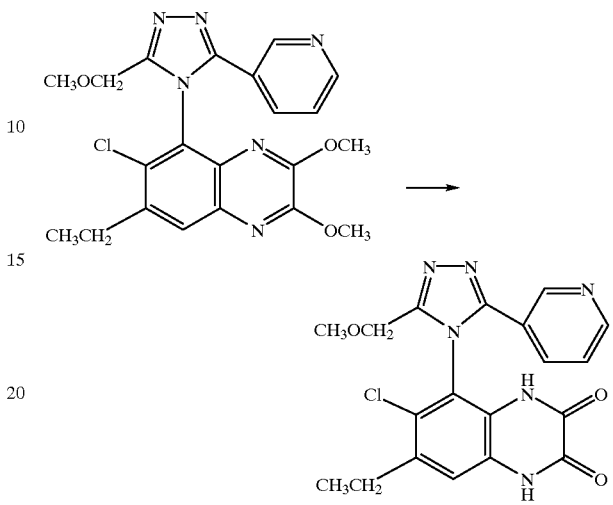

The title compound was prepared from the starting material shown (which was prepared by similar methods to those described in Preparation 113, steps (c), (d) and (e), Preparation 114 and Preparation 115 from 6-chloro-7-ethyl-5-nitro-2,3(1H,4H)-quinoxalinedione (see WO-A-95/12417)) by a similar method to that of Example 109. It was isolated as a yellow foam.

Analysis (%): Found: C, 48.68; H, 4.18; N, 17.60. $C_{19}H_{17}N_6O_3Cl \cdot HCl \cdot H_2O$ requires: C, 48.83; H, 4.31; N, 17.98.

m/z (thermospray) 413.0 (MH⁺).

EXAMPLE 113

7-Chloro-6-ethyl-5-[3-methoxymethyl-5-(3-pyridyl)-4H-1,2,4-triazol-4-yl]-2,3(1H,4H)-quinoxalinedione

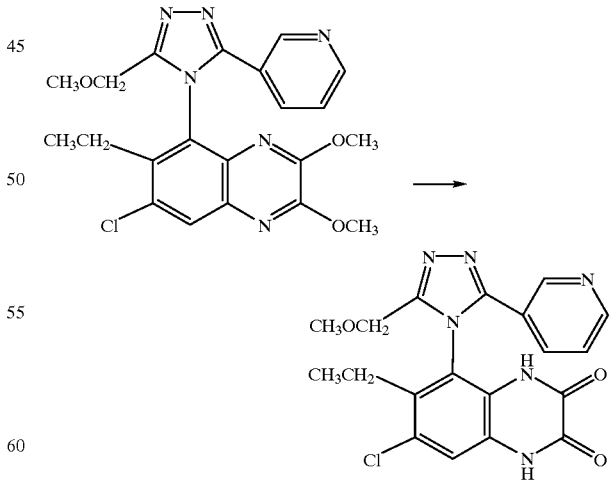

The title compound was prepared from the starting material shown (which was prepared by similar methods to those described in Preparation 113, steps (c), (d) and (e), Preparation 114 and Preparation 115 from 7-chloro-6-ethyl-5- nitro-2,3(1H,4H)-quinoxalinedione (see WO-A-95/12417)) by a similar method to that of Example 109. It was isolated as a yellow foam.

Analysis (%): Found: C, 46.28; H, 4.17; N, 16.70. $C_{19}H_{17}N_6O_3Cl \cdot 2HCl \cdot \frac{1}{3} H_2O$ requires: C, 46.41; H, 4.03; N, 17.09.

m/z (thermospray) 413.0 ($MH^+$).

EXAMPLE 114

(−)-6,7-Dichloro-5-[3-methoxymethyl-5-(1-oxidopyridin-3-yl)-4H-1,2,4-triazol-4-yl]-2,3(1H,4H)-quinoxalinedione

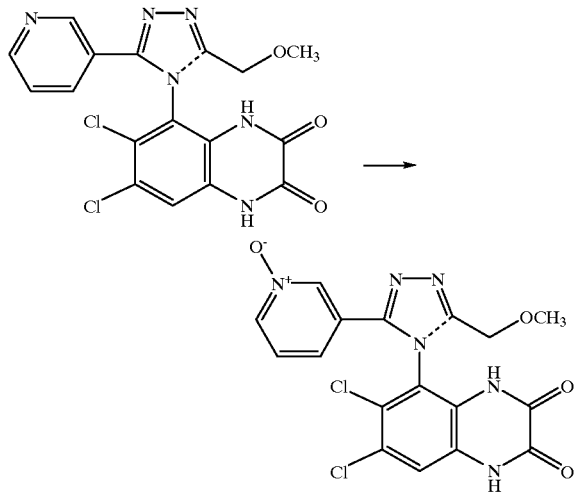

A solution of 3-chloroperoxybenzoic acid (0.85 g, 4.93 mmol) in acetone (20 ml) was added in one portion to a suspension of (−)-6,7-dichloro-5-[3-methoxymethyl-5-(3-pyridyl)-4H-1,2,4-triazol-4-yl]-2,3(1H,4H)-quinoxalinedione (see Example 111) (1.0 g, 2.24 mmol) in acetone (40 ml) which caused all the solid to dissolve. The reaction was stirred at room temperature for 40 minutes after which time a white solid began to form. The reaction mixture was allowed to stir at room temperature for 3 days. The white solid was collected by filtration and purified by flash chromatography on silica gel using dichloromethane:methanol:glacial acetic acid (90:10:1, by volume) as eluent, to give after combination and concentration of the appropriate fractions, the title compound (0.16 g, 17%) as a white solid, m.p. >310° C.

$[\alpha]^{25}_D$ −235° (c=1.0, ethanol).

EXAMPLES 115 TO 129

The following tabulated Examples of the general formula:

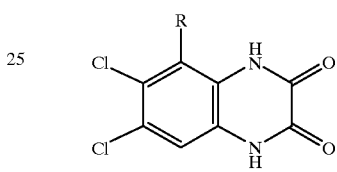

were prepared by a similar method to that of Example 1 using the corresponding 2,3-dimethoxyquinoxaline derivatives and a reaction period that corresponded approximately to the complete consumption of starting material by TLC.

TABLE 2

| Ex. No. | R | mp (° C.) | Molecular formula |
|---|---|---|---|
| 115 | | 226–229 | $C_{22}H_{14}Cl_2N_6O_3 \cdot$ 2HCl. 0.5 $H_2O$ |
| 116 | | 220–223 | $C_{23}H_{16}Cl_2N_6O_3 \cdot$ HCl.$H_2O$ |
| 117 | | 254 (decomp) | $C_{23}H_{16}Cl_2N_6O_3 \cdot$ 2HCl.$H_2O$ |

TABLE 2-continued

| # | Structure | mp (°C) | Formula |
|---|---|---|---|
| 118 | 3-pyridyl-triazole-CH₂OCH₂-cyclohexyl | 243 (decomp) | C₂₃H₂₂Cl₂N₆O₃·HCl·1.5 H₂O |
| 119 | 3-pyridyl-triazole-CH₂OCH₂-cyclopentyl | 248 (decomp) | C₂₂H₂₀Cl₂N₆O₃·HCl·1.2 H₂O |
| 120 | 3-pyridyl-triazole-CH₂OCH₂CF₃ | 257 (decomp) | C₁₈H₁₁Cl₂F₃N₆O₃·HCl·H₂O |
| 121 | CH₃-triazole-(1H-triazol-5-yl) | 291–293 | C₁₃H₈N₈O₂Cl₂·HCl·H₂O |
| 122 | 3-pyridyl-triazole-CH₂CH₂-phenyl | 290–292 | C₂₃H₁₆N₆O₂Cl₂·H₂O |
| 123 | 3-pyridyl-triazole-CH₂-phenyl | >300 | C₂₂H₁₄N₆O₂Cl₂·1.75 H₂O |
| 124 | 3-pyridyl-triazole-CH₂OCH₂CH₃ | Solid Foam | C₁₈H₁₄Cl₂N₆O₃·HCl·0.33 dioxane·1.1 H₂O |
| 125 | CH₃OCH₂-triazole-quinolin-3-yl | Solid Foam | C₂₁H₁₄N₆O₃Cl₂·2HCl·2 H₂O |
| 126 | 3-pyridyl-triazole-CH₂CH₂OCH₂CH₃ | >300 | C₁₉H₁₆N₆O₃Cl₂·2 HCl·1.4 H₂O |
| 127 | CH₃OCH₂-triazole-quinolin-6-yl | Solid Foam | C₂₁H₁₄N₆O₃Cl₂·0.6 H₂O·0.06 dioxane |

TABLE 2-continued

| Ex. No. | Structure | m.p. (°C) | Formula |
|---|---|---|---|
| 128 | CH₃O-[triazole]-[1-phenyl-imidazole] | 231–233 | $C_{21}H_{15}N_7O_3Cl_2 \cdot 1.5 H_2O$ |
| 129 | CH₃O-[triazole]-[2-phenylpyridin-5-yl] | 230–232 | $C_{23}H_{16}N_6O_3Cl_2 \cdot 1.5 H_2O$ |

| Ex. No. | Analytical Data: Analysis (% Found (Required)) or ¹H-NMR (300 MHz, DMSO-d₆ (unless otherwise stated)) or LRMS (m/z) | Starting material Preparation no. | Trituration Solvent (a) water (b) diethyl ether (c) methanol (d) 1,4-dioxane (e) ethyl acetate (f) diisopropyl ether (g) dichloromethane (h) acetone |
|---|---|---|---|
| 115 | C, 46.94; H, 3.26; N, 14.42 (C, 46.92; H, 3.04; N, 14.92) | 135 | b |
| 116 | C, 50.62; H, 3.40; N, 15.32 (C, 50.25; H, 3.48; N, 15.29) | 136 | a |
| 117 | C, 47.09; H, 3.58; N, 14.07 (C, 47.12; H, 3.44; N, 14.30) | 137 | b |
| 118 | C, 48.96; H, 4.48; N, 14.88 (C, 48.91; H, 4.64; N, 14.88) | 138 | b |
| 119 | C, 48.42; H, 4.25; N, 15.37 (C, 48.45; H, 4.32; N, 15.41) | 139 | b |
| 120 | C, 39.92; H, 2.65, N, 15.27 (C, 39.91; H, 2.61; N, 15.51) | 140 | b |
| 121 | C, 36.05; H, 2.55; N, 25.73 (C, 36.01; H, 2.56; N, 25.86) | 141 | b |
| 122 | C, 55.65; H, 3.43; N, 16.76 (C, 55.55; H, 3.65; N, 16.90) | 142 | b |
| 123 | C, 53.11; H, 3.12; N, 16.84 (C, 53.19; H, 3.55; N, 16.92) | 143 | b |
| 124 | C, 45.08; H, 3.81; N, 15.74 (C, 44.75; H, 3.86; N, 16.20) | 144 | b |
| 125 | C, 43.93; H, 3.48; N, 14.23 (C, 43.62; H, 3.49; N, 14.53) | 145 | b |
| 126 | C, 42.05; H, 3.52; N, 15.28 (C, 41.84; H, 3.84; N, 15.41) | 146 | b |
| 127 | C, 45.99; H, 3.35; N, 14.66 (C, 45.69; H, 3.19; N, 15.05) | 147 | b |
| 128 | C, 49.60; H, 3.28; N, 19.22 (C, 49.33; H, 3.55; N, 9.17) | 148 | a then b |
| 129 | C, 53.09; H, 3.40; N, 15.87 (C, 52.89; H, 3.67; N, 16.09) | 149 | a |

EXAMPLE 130

(−)-6,7-Dichloro-5-[3-methoxymethyl-5-(3-pyridyl)-4H-1,2,4-triazol-4-yl]-2,3(1H,4H)-quinoxalinedione Sodium Salt Sodium hydroxide (0.959 ml of a 1 molar aqueous solution, 0.959 mmol) was added to a stirred suspension of (−)-6,7-dichloro-5-[3-methoxymethyl-5-(3-pyridyl)-4H-1,2,4-triazol-4-yl]-2,3(1H,4H)-quinoxalinedione (see Example 111) (0.428 g, 0.959 mmol) in water (10 ml) and the mixture stirred for 0.5 hour. The resulting solution was filtered and the filtrate freeze-dried to give the title compound (0.43 g, 94%) as a white solid, mp 260° C. (dec).

Analysis (%): Found: C, 42.90; H, 2.89; N, 17.76. $C_{17}H_{11}Cl_2N_6NaO_3 \cdot 1.5H_2O$ requires: C, 42.78; H, 3.17; N, 17.61.

$[\alpha]^{25}_D = -228°$ (c=0.1, H₂O).

EXAMPLE 131

Intravenous Formulation of (−)-6,7-Dichloro-5-[3-methoxymethyl-5-(3-pyridyl)-4H-1,2,4-triazol-4-yl]-2,3(1H,4H)-quinoxalinedione Sodium Salt A formulation suitable for administering a 20 mg/ml dose of the active component by intravenous injection was made up using (−)-6,7-dichloro-5-[3-methoxymethyl-5-(3-pyridyl)-4H-1,2,4-triazol-4-yl]-2,3(1H,4H)-quinoxalinedione sodium salt, 1.5 H₂O (see Example 130)

(22.4 mg per unit dose), sodium chloride (9.0 mg per unit dose) and water for injections (to 1.0 ml).

To prepare the formulation, sodium chloride is dissolved in 75% of the total volume of water in a suitable vessel with mixing. (−)-6,7-Dichloro-5-[3-methoxymethyl-5-(3-pyridyl)-4H-1,2,4-triazol-4-yl]-2,3(1H,4H)-quinoxalinedione sodium salt, 1.5 H₂O is then added and dissolved by mixing. The solution is then made up to volume with water and filtered through a clarifying 0.2 micron filter. The filtrate is filled into sterile 10 ml glass ampoules under aseptic conditions using a terminal clarifying filter and the ampoules sealed.

The following Preparations illustrate the synthesis of certain intermediates used in the preceeding Examples.

PREPARATION 1

6,7-Dichloro-2,3-dimethoxyquinoxaline

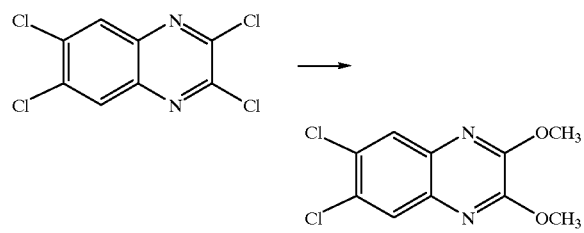

A solution of sodium methoxide (25% wt/v in methanol, 190 mL, 880 mmol) was added dropwise to a stirred suspension of 2,3,6,7-tetrachloroquinoxaline (106 g, 400 mmol) in methanol (1400 mL) at room temperature under nitrogen. After 3 days, a solution of sodium methoxide (25% wt/v in methanol, 40 mL, 190 mmol) was added, followed by tetrahydrofuran (300 mL). The reaction mixture was heated under reflux for 5 minutes, cooled, concentrated to a small volume under reduced pressure and poured into water (500 mL). The precipitate was collected by filtration and washed with water to afford the title compound (97 g, 95%) as a pink solid, mp 144–146° C.

¹H-NMR (300 MHz, CDCl₃): δ=4.14 (6H, s), 7.88 (2H, s).

m/z (thermospray) 259 (MH⁺).

PREPARATION 2

6,7-Dichloro-2,3-dimethoxy-5-(4-pyridyl) quinoxaline

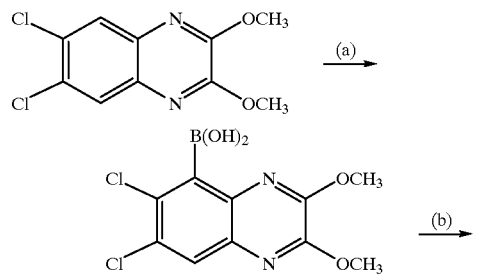

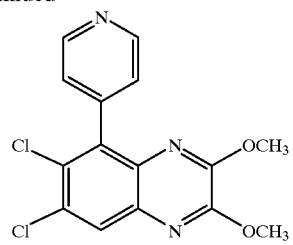

(a) Lithium diisopropylamide mono(tetrahydrofuran) (1.5M in cyclohexane, 6.18 mL, 9.26 mmol) was added to a stirred suspension of 6,7-dichloro-2,3-dimethoxyquinoxaline (Preparation 1, 2.0 g, 7.72 mmol) in dry tetrahydrofuran (150 mL) at −78° C., under nitrogen. After 1 hour at −78° C., trimethyl borate (1.47 mL, 2.0 g, 19.3 mmol) was added. The solution was stirred for a further 1 hour and then left to reach room temperature over 18 hours. Water (50 mL) was added, the solution was acidified to pH 1 with 2M aqueous hydrochloric acid solution and extracted with dichloromethane (3×150 mL). The combined organic extracts were dried (MgSO₄) and concentrated under reduced pressure. The residue was purified by flash chromatography on silica gel, by gradient elution using dichloromethane:methanol (100:0 changing to 99:1, by volume) as the eluent to afford 6,7-dichloro-2,3-dimethoxyquinoxaline-5-boronic acid (0.610 g, 26%) as a light brown solid.

¹H-NMR (300 MHz, DMSO-d₆): δ=3.97 (3H, s), 4.02 (3H, s), 7.88 (1H, s), 8.50 (2H, s).

m/z (thermospray) 303 (MH⁺).

(b) A mixture of 6,7-dichloro-2,3-dimethoxyquinoxaline-5-boronic acid (0.27 g, 0.89 mmol), 4-bromopyridine (0.14 g, 0.89 mmol) and tetrakis(triphenylphosphine)palladium (O) (0.031 g, 0.026 mmol) in a mixture of 2M aqueous sodium carbonate solution (1 mL), ethanol (0.5 mL) and toluene (10 mL) was heated under nitrogen under reflux for 24 hours. After being cooled the mixture was partitioned between water (20 mL) and dichloromethane (20 mL). The phases were separated and the aqueous phase was extracted with dichloromethane (3×50 mL). The combined organic extracts were dried (MgSO₄) and concentrated under reduced pressure to give a brown solid which was purified by flash chromatography on silica gel, eluting with hexane-:ethyl acetate (3:1, by volume) to afford the title compound (0.113 g, 38%) as a beige solid.

¹H-NMR (300 MHz, CDCl₃): δ=3.80 (3H, s), 4.17 (3H, s), 7.30 (2H, d, J=5 Hz), 7.97 (1H, s), 8.73 (2H, d, J=5 Hz).

m/z (thermospray) 336 (MH⁺).

PREPARATIONS 3–5

The following tabulated compounds were prepared by a similar method to that of Preparation 2, part b, using 6,7-dichloro-2,3-dimethoxyquinoxaline-5-boronic acid and the appropriate heterocyclic bromides (R—Br) in place of 4-bromopyridine.

| Prep. No. | R | $^1$H NMR (300 MHz, CDCl$_3$) and m/z |
|---|---|---|
| 3 | 2-pyridyl | δ = 3.77(3H, s), 4.14(3H, s), 7.35(2H, m), 7.80 (1H, m), 7.97(1H, s), 8.77(1H, d, J=5Hz). (thermospray) 336 (MH$^+$) |
| 4 | 2-pyrimidinyl | δ = 3.77(3H, s), 4.15(3H, s), 7.38(1H, t, J=3Hz), 8.00(1H, s), 8.95(2H, d, J=3Hz). (thermospray) 337 (MH$^+$) |
| 5 | 5-pyrimidinyl | δ = 3.89(3H, s), 4.19(3H, s), 8.02(1H, s), 8.83 (2H, s), 9.26(1H, s). (thermospray) 337 (MH$^+$) |

PREPARATION 6

6,7-Dichloro-2,3-dimethoxyquinoxaline-5-carboxylic Acid

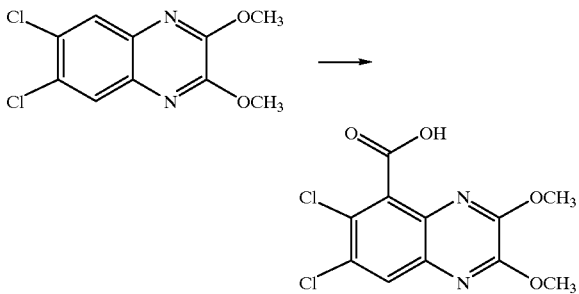

Lithium diisopropylamide mono(tetrahydrofuran) (1.5M in cyclohexane, 15.5 mL, 23.3 mmol) was added to a stirred suspension of 6,7-dichloro-2,3-dimethoxyquinoxaline (Preparation 1, 5.0 g, 19.3 mmol) in dry tetrahydrofuran (150 mL) at −78° C. under nitrogen. The reaction mixture was stirred at this temperature for 1 hour, then anhydrous carbon dioxide was bubbled through the solution at −78° C. for 1 hour. Saturated aqueous ammonium chloride solution (80 mL) was added and the resulting mixture was allowed to reach room temperature, acidified to pH 1 using 2M aqueous hydrochloric acid solution and extracted with ethyl acetate (3×50 mL). The combined organic extracts were then extracted with 1M aqueous sodium hydroxide solution. The aqueous solution was acidified to pH 1 using 2M aqueous hydrochloric acid solution and extracted with dichloromethane (3×50 mL). The combined dichloromethane extracts were dried (MgSO$_4$) and concentrated under reduced pressure to give the title compound (4.0 g, 68%) as a pale brown solid, mp 230–232° C.

$^1$H-NMR (300 MHz, DMSO-d$_6$): δ=3.98 (3H, s), 4.04 (3H, s), 8.02 (1H, s), 13.85 (1H, br s).

PREPARATION 7

6,7-Dichloro-2,3-dimethoxy-5-(N-methylcarbamoyl)quinoxaline

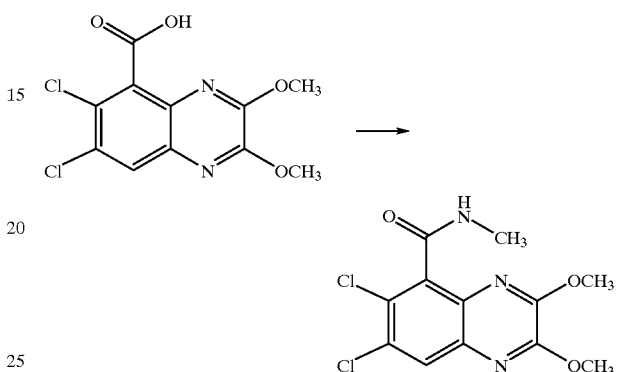

To a solution of 6,7-dichloro-2,3-dimethoxyquinoxaline-5-carboxylic acid (Preparation 6, 0.890 g, 2.93 mmol) in dichloromethane (25 mL) at room temperature under nitrogen was added dry N,N-dimethylformamide (50 μL, 47.2 mg, 0.64 mmol) followed by oxalyl chloride (0.338 mL, 3.8 mmol). After 0.5 hours, the mixture was concentrated under reduced pressure. Dichloromethane (10 mL) was added to the residue at room temperature under nitrogen, followed by methylamine (33% w/w solution in ethanol, 10 mL, 80.3 mol). After 10 minutes, the mixture was evaporated under reduced pressure and the residue was partitioned between dichloromethane (20 mL) and 1M aqueous hydrochloric acid solution. The organic extract was dried (MgSO$_4$) and evaporated under reduced pressure. The residue was purified by flash chromatography on silica gel, by gradient elution using dichloromethane:methanol (100:0 changing to 99:1, by volume) as the eluent to give a solid which was recrystallised from toluene to afford the title compound (0.570 g, 61%) as a white solid.

$^1$H-NMR (300 MHz, CDCl$_3$): δ=3.11 (3H, d, J=3 Hz), 4.10 (3H, s), 4.05 (3H, s), 5.87 (1H, br d, J=3 Hz), 7.87 (1H, s).

m/z (thermospray) 316 (MH$^+$).

PREPARATION 8

6,7-Dichloro-2,3-dimethoxy-5-(1-methyl-1H-tetrazol-5-yl)quinoxaline

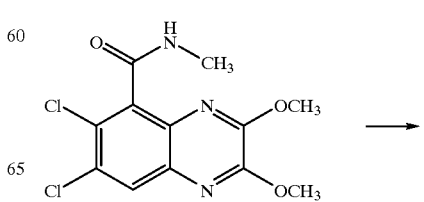

-continued

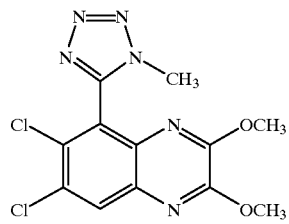

Phosphorous pentachloride (0.136 g, 0.65 mmol) was added to a solution of 6,7-dichloro-2,3-dimethoxy-5-(N-methylcarbamoyl)quinoxaline (Preparation 7, 0.197 g, 0.62 mmol) in toluene (7 mL) and the mixture was heated under reflux under nitrogen for 1 hour. The reaction was cooled to room temperature and trimethylsilyl azide (123 μL, 0.107 g, 0.93 mmol) was added. After stirring at room temperature for 18 hours, dilute aqueous ammonia solution (20 mL) was added and the mixture was extracted with dichloromethane (3×50 mL). The combined organic extracts were dried (MgSO$_4$) and evaporated under reduced pressure. The residue was purified by flash chromatography on silica gel, eluting with dichloromethane to give the title compound (0.080 g, 38%) as a white solid.

$^1$H-NMR (300 MHz, CDCl$_3$): δ=3.84 (3H, s), 3.90 (3H, s), 4.14 (3H, s), 8.15 (1H, s).

m/z (thermospray) 341 (MH$^+$).

PREPARATIONS 9–17

The following tabulated compounds were prepared by similar methods to those of Preparations 7 and 8, using 6,7-dichloro-2,3-dimethoxyquinoxaline-5-carboxylic acid and the appropriate primary amine (R—NH$_2$) in place of methylamine.

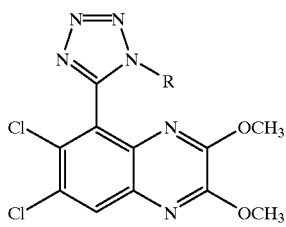

| Prep. No. | R | $^1$H NMR (300 MHz, CDCl$_3$) and m/z | Variations from Preparation 8 |
|---|---|---|---|
| 9 | cyclohexyl-CH$_2$– | δ = 1.18(3H, m), 1.50(1H, m), 1.72(4H, m), 1.94(2H, m), 3.68(3H, s), 4.06(3H, s), 4.08 (1H, m), 8.32(1H, s). (thermospray) 409 (MH$^+$) | No flash chromatography. Trituration with ethyl acetate. |
| 10 | –CH$_2$–C$_6$H$_5$ (benzyl extended) | δ = 3.18(2H, m), 3.76(3H, s), 4.16(3H, s), 4.40(2H, m), 6.92(2H, m), 7.10(3H, m), 8.10 (1H, s). (thermospray) 431 (MH$^+$) | — |
| 11 | –CH$_2$CO$_2$CH$_3$ | δ = 3.64(3H, s), 3.86(3H, s), 4.18(3H, s), 4.84(1H, d, J=18Hz), 5.10(1H, d, J=18Hz), 8.12(1H, s). (thermospray) 399 (MH$^+$) | — |
| 12 | –CH(CH$_3$)$_2$ | δ = 1.58(6H, m), 3.80(3H, s), 4.18(3H, s), 4.28(1H, m), 8.14(1H, s). (thermospray) 369 (MH$^+$) | — |
| 13 | –CH$_2$CH$_3$ | δ = 1.46(3H, t, J=10Hz), 3.82(3H, s), 4.16 (3H, s), 4.20(2H, m), 8.16(1H, s). (thermospray) 355 (MH$^+$) | — |
| 14 | –CH$_2$C$_6$H$_5$ | δ = 3.64(3H, s), 4.14(3H, s), 5.26(1H, d, J=18Hz), 5.44(1H, d, J=18Hz), 6.84(2H, m), 7.12(3H, m), 8.06(1H, s). (thermospray) 417 (MH$^+$) | — |
| 15 | –CH$_2$CH$_2$OCH$_3$ | δ = 3.14(3H, s), 3.66(2H, m), 3.80(3H, s), 4.14(3H, s), 4.24(1H, m), 4.40(1H, m), 8.12 (1H, s). (thermospray) 385 (MH$^+$) | — |

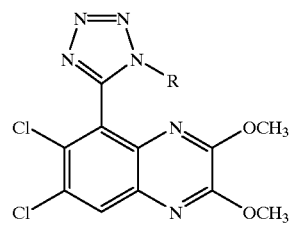

| Prep. No. | R | ¹H NMR (300 MHz, CDCl₃) and m/z | Variations from Preparation 8 |
|---|---|---|---|
| 16 | (phenyl) | δ = 3.80(3H, s), 4.12(3H, s), 7.38(5H, m), 8.06(1H, s).<br>(thermospray) 403 (MH⁺) | Isolated by reverse phase preparative hplc on a Spherisorb (trademark) S5ODS2 column eluting with 70:30, by volume, water:methanol. |
| 17 | —CH₂CF₃ | δ = 3.82(3H, s), 4.16(3H, s), 4.88(2H, q, J=8Hz), 8.18(1H, s).<br>(thermospray) 409 (MH⁺) | Chromatography eluent: gradient elution using hexane: dichloromethane, 1:1 changing to 3:7, by volume. |

PREPARATION 18

6,7-Dichloro-2,3-dimethoxy-5-(N-allylcarbamoyl)quinoxaline

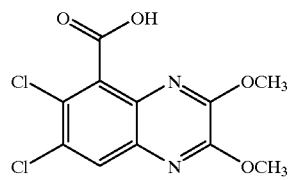

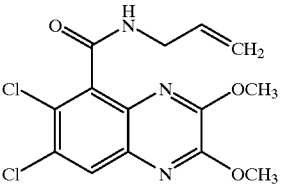

The title compound was prepared by a similar method to that of Preparation 7, using allylamine in place of methylamine.

¹H-NMR (300 MHz, CDCl₃): δ=4.10 (3H, s), 4.14 (3H, s), 4.19 (2H, m), 5.20 (1H, d, J=10 Hz), 5.38 (1H, dd, J=2, 10 Hz), 5.85 (1H, br s), 6.00 (1H, m), 7.88 (1H, s).

m/z (thermospray) 342 (MH⁺).

PREPARATION 19

6,7-Dichloro-2,3-dimethoxy-5-(1-allyl-1H-tetrazol-5-yl)quinoxaline

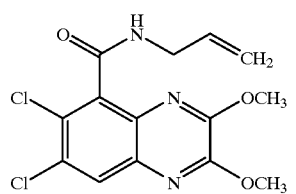

The title compound was prepared by a similar method to that of Preparation 8, using 6,7-dichloro-2,3-dimethoxy-5-(N-allylcarbamoyl)quinoxaline (Preparation 18) in place of 6,7-dichloro-2,3-dimethoxy-5-(N-methylcarbamoyl)quinoxaline.

¹H-NMR (300 MHz, CDCl₃): δ=3.80 (3H, s), 4.14 (3H, s), 4.80 (2H, m), 5.02 (1H, m), 5.16 (1H, m), 5.80 (1H, m), 8.10 (1H, s).

m/z (thermospray) 367 (MH⁺).

PREPARATION 20

6,7-Dichloro-2,3-dimethoxy-5-[1-(3-hydroxypropyl)-1H-tetrazol-5-yl]quinoxaline

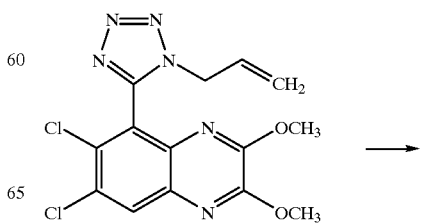

-continued

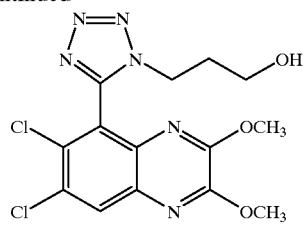

9-Borabicyclo[3.3.1]nonane (0.5M in tetrahydrofuran, 9.1 mL, 4.55 mmol) was added dropwise to a stirred suspension of 6,7-dichloro-2,3-dimethoxy-5-(1-allyl-1H-tetrazol-5-yl)quinoxaline (Preparation 19, 0.67 g, 1.82 mmol) in dry tetrahydrofuran (15 mL) at room temperature under nitrogen. The reaction mixture was heated under reflux for 18 hours, trimethylamine-N-oxide (1.03 g, 13.7 mmol) was added portionwise to the cooled reaction mixture and the mixture was heated under reflux for 2 hours then concentrated under reduced pressure. The residue was purified by flash chromatography on silica gel, by gradient elution using dichloromethane:methanol (100:0 changing to 99.5:0.5, by volume) to give the title compound (0.510 g, 73%) as a white solid, mp 188–189° C.

$^1$H-NMR (300 MHz, CDCl$_3$): δ=2.04 (2H, m), 3.60 (2H, m), 3.82 (3H, s), 4.16 (3H, s), 4.30 (2H, m), 8.12 (1H, s).

m/z (thermospray) 769 (2MH$^+$).

PREPARATION 21

6,7-Dichloro-2,3-dimethoxy-5-[1-(2-hydroxyethyl)-1H-tetrazol-5-yl]quinoxaline

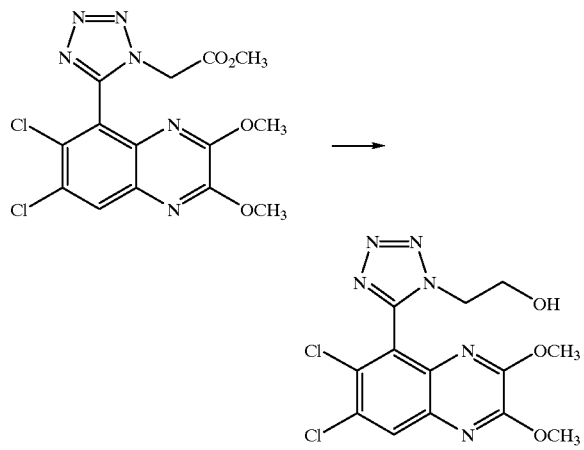

Diisobutylaluminium hydride (1M in tetrahydrofuran, 0.7 mL, 0.7 mmol) was added dropwise to a stirred solution of 6,7-dichloro-2,3-dimethoxy-5-(1-methoxycarbonylmethyl-1H-tetrazol-5-yl)quinoxaline (Preparation 11, 0.126 g, 0.32 mmol) in dichloromethane (15 mL) at −78° C. under nitrogen. After 1 hour, the reaction mixture was allowed to warm to room temperature and diisobutylaluminium hydride (1M in tetrahydrofuran, 0.7 mL, 0.7 mmol) was added, followed 30 minutes later by further diisobutylaluminium hydride (1M in tetrahydrofuran, 0.7 mL, 0.7 mmol). After a further 0.25 hours saturated ammonium chloride solution (20 mL) was added to the mixture and the aqueous phase was extracted with dichloromethane (2×25 mL). The combined organic extracts were washed with brine (50 mL), dried (MgSO$_4$) and concentrated under reduced pressure. The residue was purified by flash chromatography on silica gel, eluting with dichloromethane:methanol (99:1, by volume) to give the title compound (93 mg, 79%) as a white solid.

$^1$H-NMR (300 MHz, CDCl$_3$): δ=3.84 (3H, s), 4.08 (2H, m), 4.18 (3H, s), 4.28 (2H, m), 8.14 (1H, s).

m/z (thermospray) 371 (MH$^+$).

PREPARATION 22

6,7-Dichloro-2,3-dimethoxy-5-[4-(2-hydroxyethyl)-4H-1,2,3-triazol-3-yl]quinoxaline

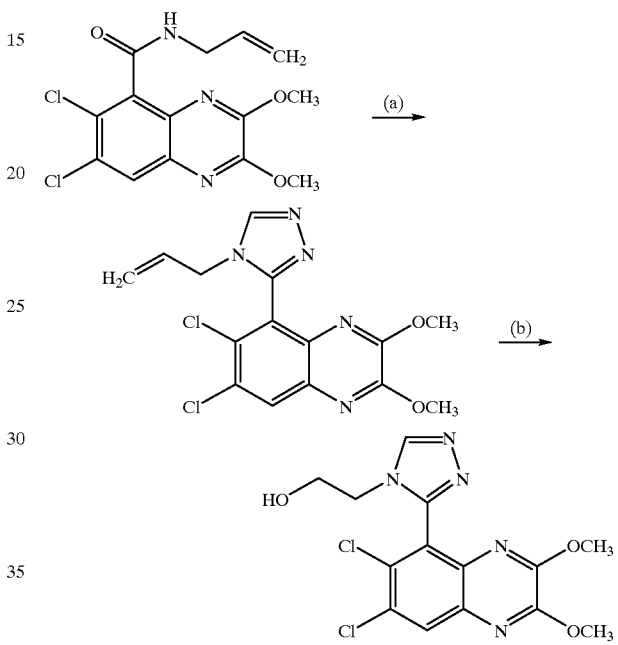

(a) Phosphorus pentachloride (0.67 g, 3.22 mmol) was added to a stirred suspension of 6,7-dichloro-2,3-dimethoxy-5-(N-allylcarbamoyl)quinoxaline (Preparation 18, 1.0 g, 2.93 mmol) in toluene (40 mL) at room temperature and then heated under reflux for 1 hour. After being cooled, formylhydrazine (0.585 g, 8.79 mmol) and triethylamine (0.592 g, 8.79 mmol) were added and the mixture heated under reflux for 1 hour. After being cooled, the mixture was partitioned between ethyl acetate (60 mL) and 10% w/w aqueous potassium carbonate solution (60 mL). The phases were separated and the aqueous phase extracted with ethyl acetate (2×40 mL). The combined organic extracts were dried (MgSO$_4$) and concentrated under reduced pressure. The residue was purified by flash chromatography on silica gel, by gradient elution using toluene-:ethyl acetate (1:0 changing to 1:1, by volume) to afford 6,7-dichloro-2,3-dimethoxy-5-(4-allyl-4H-1,2,4-triazol-3-yl)quinoxaline (0.112 g, 10%) as a white solid, mp 206–208° C.

$^1$H-NMR (300 MHz, CDCl$_3$): δ=3.88 (3H, s), 4.14 (3H, s), 4.37 (2H, d, J=3 Hz), 5.16 (2H, m), 5.79 (1H, m), 8.06 (1H, s), 8.34 (1H, s).

m/z (thermospray) 366 (MH$^+$).

(b) A solution of 6,7-dichloro-2,3-dimethoxy-5-(4-allyl-4H-1,2,4-triazol-3-yl)quinoxaline (0.1 g, 0.273 mmol) in dichloromethane (3 mL) was cooled to −70° C. and a stream of ozone/oxygen passed through for 0.5 hour. A stream of nitrogen was then passed through for 0.25 hour and then methanol (3 mL) and sodium borohydride (0.026 g, 0.683 mmol) were added. After warming to room temperature, the mixture was partitioned between dichloromethane (10 mL) and brine (10 mL). The phases were separated and the aqueous phase extracted with ethyl acetate (2×10 mL). The combined organic extracts were dried (MgSO₄) and concentrated under reduced pressure. The residue was purified by flash chromatography on silica gel, by gradient elution using ethyl acetate:methanol (100:0 changing to 95:5, by volume) to afford the title compound (0.042 g, 40%) as an off-white solid, mp 212–214° C.

¹H-NMR (300 MHz, CDCl₃): δ=3.78 (2H, m), 3.87 (3H, s), 3.92 (2H, m), 4.18 (3H, s), 8.07 (1H, s), 8.63 (1H, s).

m/z (thermospray) 370 (MH⁺).

PREPARATION 23

6,7-Dichloro-2,3-dimethoxy-5-(4-methyl-4H-1,2,4-triazol-3-yl)quinoxaline

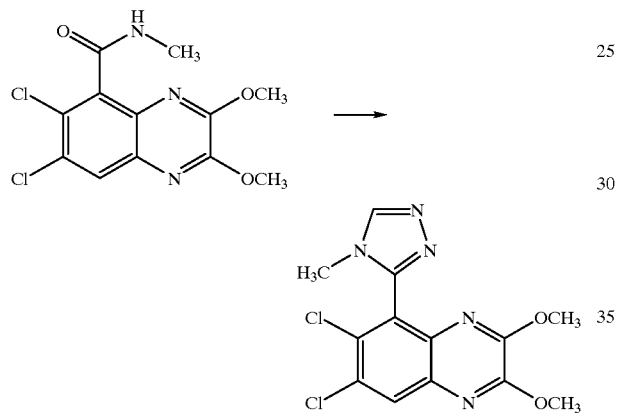

The title compound was prepared by a similar method to that of Preparation 22, step (a), using 6,7-dichloro-2,3-dimethoxy-5-(N-methylcarbamoyl)quinoxaline (Preparation 7) in place of 6,7-dichloro-2,3-dimethoxy-5-(N-allylcarbamoyl)quinoxaline. Purification by flash chromatography on silica gel, by gradient elution using toluene::ethyl acetate (1:1 changing to 0:1, by volume) gave an off-white solid.

¹H-NMR (300 MHz, CDCl₃): δ=3.52 (3H, s), 3.88 (3H, s), 4.17 (3H), 8.07 (1H, s), 8.37 (1H, s).

m/z (thermospray) 340 (MH⁺).

PREPARATION 24

6,7-Dichloro-2,3-dimethoxyquinoxaline-5-carboxamide

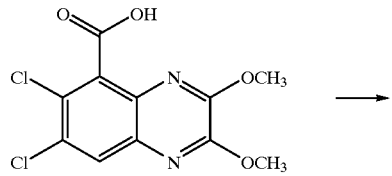

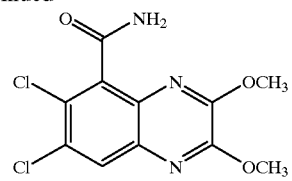

The title compound was prepared by a similar method to that of Preparation 7, using gaseous ammonia in place of methylamine, to afford a pale yellow solid (no chromatography was necessary in the work-up).

¹H-NMR (300 MHz, DMSO-d₆): δ=4.00 (3H, s), 4.06 (3H, s), 7.80 (1H, br.s), 7.92 (1H, br.s), 8.00 (1H, s).

m/z (thermospray) 302 (MH⁺).

PREPARATION 25

6,7-Dichloro-2,3-dimethoxy-5-(2-methyl-2H-1,2,4-triazol-3-yl)quinoxaline (Isomer 1) and 6,7-Dichloro-2,3-dimethoxy-5-(1-methyl-1H-1,2,4-triazol-3-yl)quinoxaline (Isomer 2)

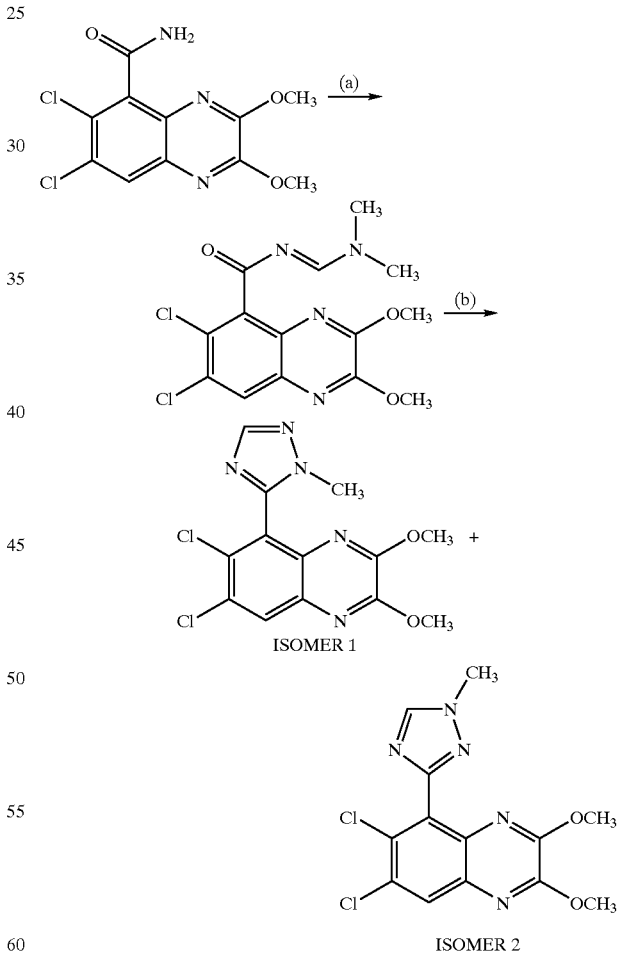

(a) 6,7-Dichloro-2,3-dimethoxyquinoxaline-5-carboxamide (Preparation 24, 1.96 g, 6.49 mmol) in N,N-dimethylformamide dimethyl acetal (25 mL) was heated under reflux for 2 hours. After being cooled the mixture was concentrated under reduced pressure and the residue triturated with diethyl ether to afford N¹,N¹-dimethyl-N²-[6,7-dichloro-2,3-dimethoxyquinoxalin-5-ylcarbonyl]formamidine (2.14 g, 92%) as a pale yellow solid.

$^1$H-NMR (300 MHz, CDCl$_3$): δ=3.18 (3H, s), 3.24 (3H, s), 4.09 (3H, s), 4.15 (3H, s), 7.88 (1H, s), 8.62 (1H, s).

m/z (thermospray) 357 (MH$^+$).

(b) A mixture of N¹,N¹-dimethyl-N²-[6,7-dichloro-2,3-dimethoxyquinoxalin-5-ylcarbonyl]formamidine (2.14 g, 5.99 mmol) and hydrazine hydrate (0.599 g, 11.98 mmol) in glacial acetic acid (80 mL) was heated under reflux for 2 hours. After being cooled, the solid was collected by filtration and washed with diethyl ether. A portion of this solid (1.108 g) was suspended in dry N,N-dimethylformamide (80 mL) at room temperature under nitrogen, and treated with sodium hydride (80% w/w dispersion in oil, 0.122 g, 4.08 mmol). After stirring for 0.25 hour, iodomethane (0.579 g, 4.08 mmol) was added and the mixture heated at 50° C. for 6 hours. The mixture was cooled, filtered and the filtrate concentrated under reduced pressure. The residue was partitioned between dichloromethane (80 mL) and brine (80 mL). The phases were separated and the aqueous phase extracted with dichloromethane (2×80 mL). The combined organic extracts were dried (MgSO$_4$) and concentrated under reduced pressure. The residue was purified by flash chromatography on silica gel, by gradient elution using toluene:ethyl acetate (4:1 changing to 1:1 by volume) to afford as the first eluted product, isomer 1, tentatively assigned as 6,7-dichloro-2,3-dimethoxy-5-(2-methyl-2H-1,2,4-triazol-3-yl)quinoxaline (0.18 g, 10%), as a white solid, mp 208–210° C.

$^1$H-NMR (300 MHz, CDCl$_3$): δ=3.73 (3H, s), 3.89 (3H, s), 4.18 (3H, s), 8.10 (1H, s), 8.13 (1H, s).

m/z (thermospray) 340 (MH$^+$).

The second eluted product, isomer 2, tentatively assigned as 6,7-dichloro-2,3-dimethoxy-5-(1-methyl-1H-1,2,4-triazol-3-yl)quinoxaline, (0.11 g, 6%), was obtained as a white solid, mp 184–186° C.

$^1$H-NMR (300 MHz, CDCl$_3$): δ=3.90 (3H, s), 4.09 (3H, s), 4.16 (3H, s), 8.02 (1H, s), 8.28 (1H, s).

m/z (thermospray) 340 (MH$^+$).

PREPARATION 26

5-Amino-6,7-dichloro-2,3-dimethoxyquinoxaline

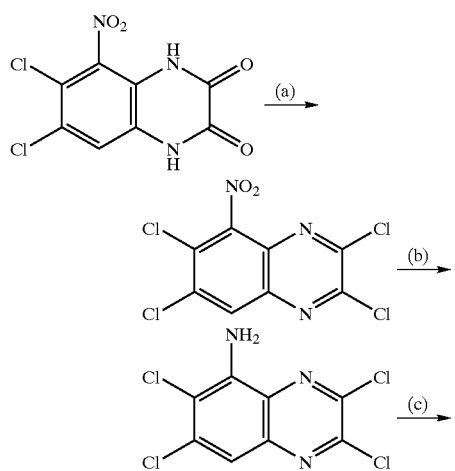

-continued

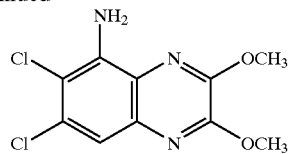

(a) A mixture of 6,7-dichloro-5-nitro-2,3(1H,4)-quinoxalinedione (Example 1 of WO-A-94/00124, 84 g, 0.34 mol), thionyl chloride (840 mL) and dimethylformamide (0.5 mL) was heated under reflux for 3 hours, cooled and concentrated under reduced pressure. Ethyl acetate (300 mL) was added and removed by evaporation under reduced pressure and this procedure was then repeated with petroleum ether (bp 100–120° C.). The solid residue was recrystallised from petroleum ether (bp 100–120° C.) to give 2,3,6,7-tetrachloro-5-nitroquinoxaline (78 g, 73%) as a light yellow solid.

$^1$H-NMR (300 MHz, CDCl$_3$): δ=8.6 (1H, s).

(b) Tin(II) chloride dihydrate (346.3 g, 1.54 mol) was added to a solution of 2,3,6,7-tetrachloro-5-nitroquinoxaline (96.2 g, 0.31 mol) in ethyl acetate (1.8 L). The mixture was heated under reflux for 4 hours, cooled and poured cautiously into an excess of aqueous saturated sodium bicarbonate solution. The mixture was filtered through CELITE (trade mark), washing well with ethyl acetate. The filter cake was macerated with further ethyl acetate and the solid material filtered off. The combined ethyl acetate phases were dried (MgSO$_4$) and concentrated under reduced pressure to give 5-amino-2,3,6,7-tetrachloroquinoxaline (73.4 g, 84%) as a yellow solid.

$^1$H-NMR (300 MHz, CDCl$_3$): δ=5.45 (2H, br, s), 7.47 (1H, s).

m/z (thermospray) 385 (MH$^+$). (In an alternative preparation, this reduction step was performed using iron filings in an aqueous acetic acid).

(c) A solution of sodium methoxide (25% w/w solution in methanol, 274 mL, 1.28 mmol) was added to a suspension of 5-amino-2,3,6,7-tetrachloroquinoxaline (72.4 g, 0.256 mmol) in dry methanol (1 L) and the resulting mixture was heated under reflux for 30 minutes. The mixture was cooled, concentrated under reduced pressure, and the residue partitioned between water and ethyl acetate (total of 8 L). The organic extracts were dried (MgSO$_4$) and concentrated under reduced pressure. The crude product was triturated with methanol then dissolved in dichloromethane (2 L) and filtered. The filtrate was concentrated under reduced pressure to give the title compound as a yellow solid (55.0 g, 79%).

$^1$H-NMR (300 MHz, CDCl$_3$): δ=4.13 (3H, s), 4.14 (3H, s), 5.07 (2H, br s), 7.26 (1H, s).

m/z (thermospray) 274 (MH$^+$).

PREPARATION 27

6,7-Dichloro-2,3-dimethoxy-5-[3-(3-chlorophenyl)-5-methyl-4H-1,2,4-triazol-4-yl]quinoxaline

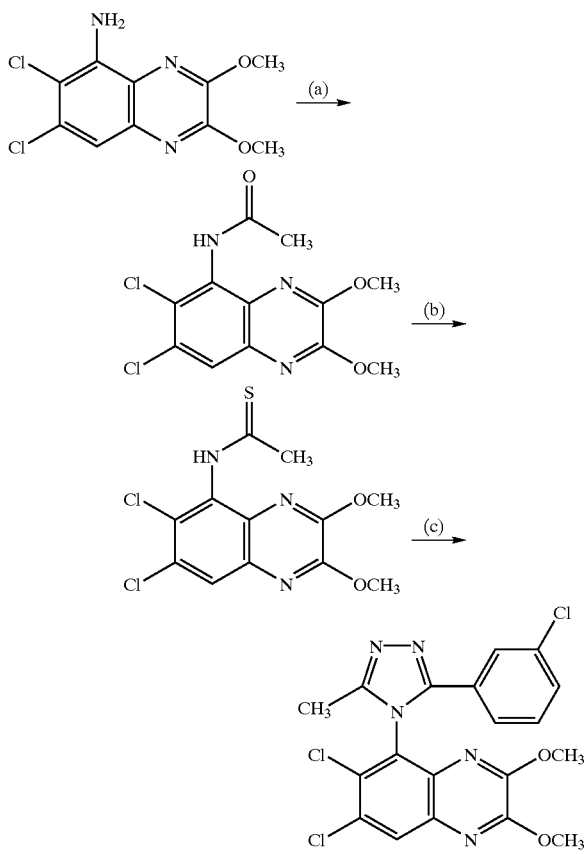

(a) Acetyl chloride (5.71 mL, 6.30 g, 80.3 mmol) was added to a vigorously stirred suspension of 5-amino-6,7-dichloro-2,3-dimethoxyquinoxaline (Preparation 26, 20.49 g, 64.8 mmol) in toluene (500 mL) and the resulting mixture was heated under reflux for 2 hours. After being cooled, the product was collected by filtration, washed with toluene and dried by suction for 15 hours to yield 5-acetamido-6,7-dichloro-2,3-dimethoxyquinoxaline (20.49 g, 89%) as a beige solid.

$^1$H-NMR (300 MHz, DMSO-$d_6$): δ=2.11 (3H, s), 4.04 (3H, s), 4.05 (3H, s), 7.91 (1H, s), 9.80 (1H, s).

m/z (thermospray) 316 (MH$^+$).

(b) 5-Acetamido-6,7-dichloro-2,3-dimethoxyquinoxaline (20.49 g, 64.8 mmol) was added to a stirred suspension of 2,4-bis(4-methoxyphenyl)-1,3-dithia-2,4-diphosphetane-2,4-disulphide (Lawesson's reagent) (15.7 g, 38.9 mmol) in toluene (432 ml) at room temperature under nitrogen. The mixture was warmed to the reflux temperature 25 minutes and was maintained at that temperature for a further 90 minutes. After being cooled the mixture was concentrated under reduced pressure and the residue purified by flash chromatography on silica gel, eluting with dichloromethane. 6,7-Dichloro-2,3-dimethoxy-5-thioacetamidoquinoxaline (17.54 g, 81%) was obtained as a yellow foam.

$^1$H-NMR (300 MHz, DMSO-$d_6$): δ=2.70 (3H, s), 3.99 (3H, s), 4.05 (3H, s), 8.05 (1H, s), 11.74 (1H, s).

m/z (thermospray) 332 (MH$^+$).

(c) A mixture of 6,7-dichloro-2,3-dimethoxy-5-thioacetamidoquinoxaline (250 mg, 0.753 mmol), 3-chlorobenzhydrazide (167 mg, 0.978 mmol), mercury(II) oxide (163 mg, 0.753 mmol), powdered 4 Å molecular sieves (175 mg) and n-butanol (7 mL) was heated under reflux for 18 hours. After being cooled, the mixture was filtered through ARBOCEL (trade mark) filter aid and the residue washed with dichloromethane. The filtrate was concentrated under reduced pressure to afford a green solid which was dissolved in dichloromethane, washed twice with 2M aqueous hydrochloric acid solution followed by brine, then dried (MgSO$_4$) and concentrated under reduced pressure. The residue was purified by flash chromatography on silica gel, eluting with dichloromethane:methanol (98:2, by volume) to give the title compound (120 mg, 35%) as a pale yellow solid.

$^1$H-NMR (300 MHz, CDCl$_3$): δ=2.21 (3H, s), 3.84 (3H, s), 4.14 (3H, s), 7.13 (2H, s), 7.25 (1H, obscured) 7.49 (1H, s), 8.08 (1H, s).

m/z (thermospray) 450 (MH$^+$).

PREPARATIONS 28–95

The following tabulated compounds were prepared by a similar method to that of Preparation 27 using 5-amino-6,7-dichloro-2,3-dimethoxyquinoxaline and the appropriate acid chloride (R$^A$COCl) and hydrazide (R$^B$CONHNH$_2$).

| Prep. No. | R$^A$ from acid chloride | R$^B$ from hydrazide | mp (° C.) |
|---|---|---|---|
| 28 | CH$_3$CH$_2$— | 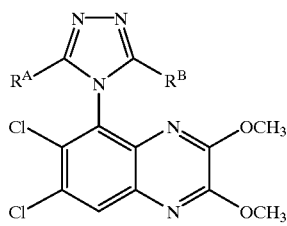 | — |

-continued
| | | | |
|---|---|---|---|
| 29 | CH₃CH₂— | —CH₃ | — |
| 30 | CH₃CH₂— | 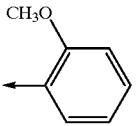 | — |
| 31 | CH₃CH₂— | 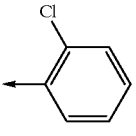 | — |
| 32 | CH₃CH₂— | H | — |
| 33 | CH₃CH₂— | 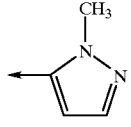 | — |
| 34 | CH₃CH₂— | 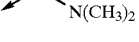 | — |
| 35 | CH₃CH₂— | 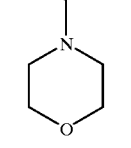 | — |
| 36 | CH₃— | 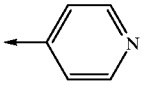 | — |
| 37 | CH₃— | 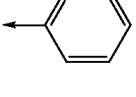 | — |
| 38 | CH₃— | 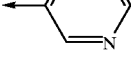 | 200–202 (decomp) |
| 39 | CH₃— | 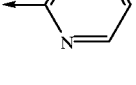 | — |
| 40 | CH₃— | 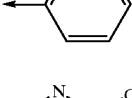 | 183–185 |
| 41 | CH₃— | 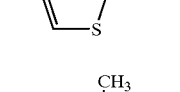 | — |
| 42 | CH₃— | 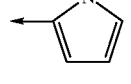 | — |

-continued
| | | | |
|---|---|---|---|
| 43 | CH₃— | 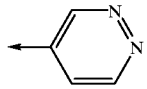 | — |
| 44 | CH₃— | 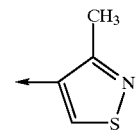 | — |
| 45 | CH₃— | 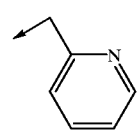 | — |
| 46 | CH₃— | 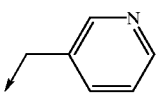 | — |
| 47 | CH₃— | 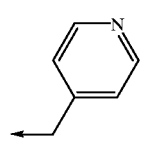 | — |
| 48 | CH₃— | 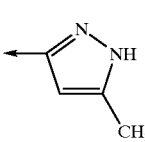 | — |
| 49 | CH₃— | 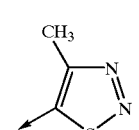 | — |
| 50 | CH₃— | 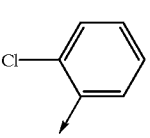 | — |
| 51 | CH₃— | 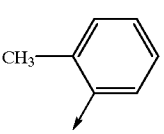 | — |
| 52 | CH₃— | 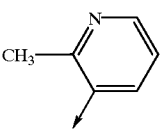 | — |
| 53 | CH₃— | 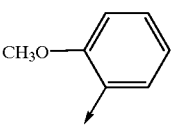 | — |

-continued
| | | | |
|---|---|---|---|
| 54 | CH₃— | 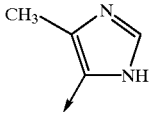 | — |
| 55 | CH₃— | 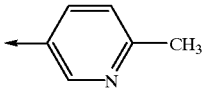 | — |
| 56 | CH₃— | 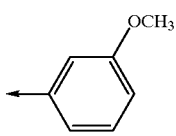 | solid foam |
| 57 | CH₃— | 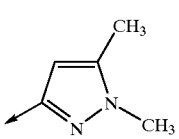 | oil |
| 58 | CH₃— | 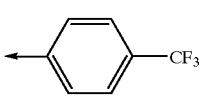 | solid foam |
| 59 | CH₃— | 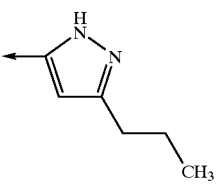 | 232–234 |
| 60 | CH₃— | 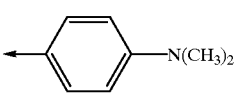 | oil |
| 61 | CH₃— | 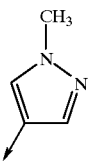 | — |
| 62 | CH₃— | 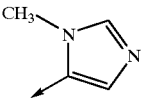 | solid foam |
| 63 | CH₃— | 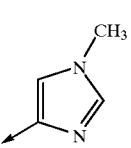 | solid foam |
| 64 | CH₃— | 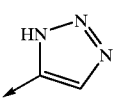 | — |

-continued
| | | | |
|---|---|---|---|
| 65 | CH₃— | 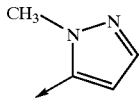 | solid foam |
| 66 | CH₃— | 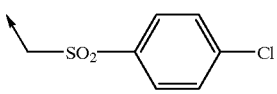 | 222–225 |
| 67 | CH₃— | —CO₂CH₂CH₃ | 196–198 |
| 68 | CH₃— | 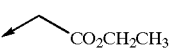 | oil |
| 69 | CH₃— | 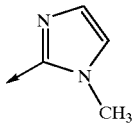 | 242–245 |
| 70 | CH₃— | 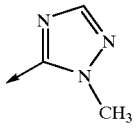 | 248–249 |
| 71 | CH₃— | 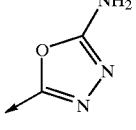 | — |
| 72 | CH₃— | 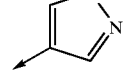 | 171–173 |
| 73 | CH₃— | 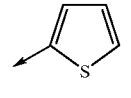 | — |
| 74 | CH₃— | 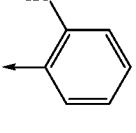 | — |
| 75 | CH₃— | 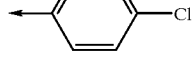 | — |
| 76 | CH₃— | 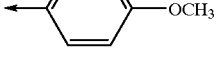 | — |
| 77 | CH₃— | —CH₃ | — |
| 78 | CH₃— | H | — |
| 79 | CH₃— |  | — |

-continued
| | | | |
|---|---|---|---|
| 80 | CH₃— | 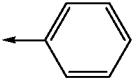 | — |
| 81 | CH₃— | —OH<br>note 1 | — |
| 82 | CH₃OCH₂— | 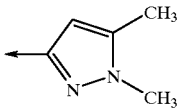 | 204–207 |
| 83 | CH₃OCH₂— | 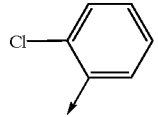 | 212–214 |
| 84 | CH₃OCH₂— | 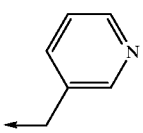 | — |
| 85 | CH₃OCH₂— | 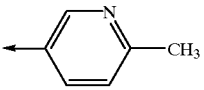 | — |
| 86 | CH₃OCH₂— | 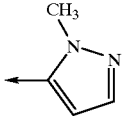 | — |
| 87 | CH₃OCH₂— | —CH₂OCH₃<br>note 2 | — |
| 88 | CH₃OCH₂— | 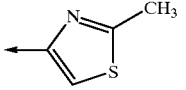 | — |
| 89 | CH₃OCH₂— | 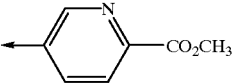 | 197–198 |
| 90 | CH₃O(CH₂)₂— | 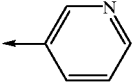 | — |
| 91 | CH₃O₂C(CH₂)₃— | 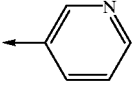 | — |
| 92 | —CO₂CH₂CH₃ | H | — |
| 93 | —CO₂CH₂CH₃ | 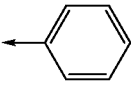 | — |

-continued

| | | | |
|---|---|---|---|
| 94 | —CO₂CH₂CH₃ | pyridine structure | — |
| 95 | phenyl structure | phenyl structure | — |

| Prep. No. | ¹H-NMR (300 MHz, CDCl₃) or m/z or Analysis (%) | Work-up and chromatography eluent variations for step (c) | Reference for hydrazide |
|---|---|---|---|
| 28 | δ = 1.24(3H, t, J=8Hz), 2.45(1H, dq, J=15, 8Hz), 2.59(1H, dq, J=15, 8Hz), 3.88(3H, s), 4.16(3H, s), 7.24(1H, m), 7.86(1H, m), 8.09(1H, s), 8.43 (1H, br s), 8.51–8.55(1H, m). m/z (thermospray) 431 (MH⁺). | No acid wash | — |
| 29 | δ = 1.18(3H, t, J=8Hz), 2.12(3H, s), 2.36–2.50(2H, m), 3.84(3H, s), 4.18 (3H, s), 8.09(1H, s). m/z (thermospray) 368 (MH⁺). | No acid wash | — |
| 30 | δ = 1.20(3H, t J=8Hz), 2.47(1H, dq, J=15, 8Hz), 2.68(1H, dq, J=15, 8Hz), 3.38(3H, s), 3.89(3H, s), 4.10(3H, s), 6.63(1H, d, J=9Hz), 6.86(1H, J=9Hz), 7.23(1H, m, obscured), 7.48(1H, d, J=9Hz), 7.94(1H, s). m/z (thermospray) 460 (MH⁺). | — | — |
| 31 | δ = 1.24(3H, t, J=8Hz), 2.48–2.58(2H, m), 3.98(3H, s), 4.13(3H, s), 7.05 (1H, m), 7.26(3H, m, obscured), 7.98 (1H, s). m/z (thermospray) 460 (MH⁺). | — | — |
| 32 | δ = 1.24(3H, t, J=8Hz), 2.55(2H, m), 3.89(3H, s), 4.19(3H, s), 8.09(1H, s), 8.11(1H, s). m/z (thermospray) 354 (MH⁺). | — | — |
| 33 | δ = 1.24(3H, t, J=8Hz), 2.50(2H, m), 3.81(3H, s), 4.17(3H, s), 4.21(3H, s), 5.29(1H, s), 5.44(1H, s), 7.19(1H, s), 8.08(1H, s). m/z (thermospray) 433.6 (MH⁺). | — | Preparation 121 |
| 34 | δ = 1.19(3H, t, J=8Hz), 1.99(6H, s), 2.44(2H, m), 3.38(2H, q, J=12Hz), 3.86(3H, s), 4.18(3H, s), 8.15(1H, s). m/z (thermospray) 410.6 (MH⁺). | No acid wash | — |
| 35 | δ = 1.20(3H, t, J=8Hz), 2.21(2H, br d), 2.49(2H, m), 3.21(2H, br d), 3.51 (2H, m), 3.83(3H, s), 4.18(3H, s), 8.19(1H, s). m/z (thermospray) 452.9 (MH⁺). | No acid wash | Eur. J. Med. Chem., 1994, 389. |
| 36 | δ = 2.04(3H, s), 3.80(3H, s), 4.14(3H, s), 7.23(2H, d, J=6Hz), 8.13(1H, s), 8.50(2H, d, J=6Hz). m/z (thermospray) 417 (MH⁺). | No acid wash; 99:1, by volume, ethyl acetate: methanol | — |
| 37 | δ = 2.13(3H, s), 3.77(3H, s), 4.11(3H, s), 7.07(1H, m), 7.67(1H, t, J=8Hz), 7.98(1H, d, J=5Hz), 8.05(1H, s), 8.28 (1H, d, J=8Hz). m/z (thermospray) 417 (MH⁺). | No acid wash; 99:1, by volume, ethyl acetate: methanol | Aust. J. Chem., 38(10), 1491 (1985) |
| 38 | δ = 2.27(3H, s), 3.75(3H, s), 4.15(3H, s), 7.99(1H, m), 8.07(1H, s), 8.39 (1H, m), 9.52(1H, m). m/z (thermospray) 418 (MH⁺). | No acid wash; ethyl acetate | Chem. Abstr., 103, 104893e (1985) |
| 39 | δ = 2.27(3H, s), 3.77(3H, s), 4.14(3H, s), 7.09(1H, t, J=5Hz), 8.05(1H, s), 8.50(2H, d, J=5Hz). m/z (thermospray) 418 (MH⁺). | — | Preparation 117 |
| 40 | δ = 2.23(3H, s), 3.85(3H, s), 4.17(3H, s), 7.25(1H, m), 7.88(1H, m), 8.08 (1H, s), 8.43(1H, m), 8.52(1H, m). m/z (thermospray) 417 (MH⁺). | No acid wash. | — |

| | | | |
|---|---|---|---|
| 41 | δ = 2.21(3H, s), 2.32(3H, s), 3.78 (3H, s), 4.13(3H, s), 7.69(1H, s), 8.08 (1H, s). m/z (thermospray) 437 (MH$^+$). | No acid wash. | Aust. J. Chem., 38(8), 1257 (1985) |
| 42 | δ = 2.20(3H, s), 3.86(3H, s), 3.99 (3H, s), 4.12(3H, s), 5.4(1H, m), 5.85 (1H, m), 6.65(1H, m), 8.10(1H, s). m/z (thermospray) 419 (MH$^+$). | No acid wash. | — |
| 43 | δ = 2.16(3H, s), 3.74(3H, s), 4.08 (3H, s), 7.24(1H, m), 8.30(1H, s), 9.08(1H, m), 9.24(1H, s). m/z (thermospray) 418 (MH$^+$). | hexane:ethyl acetate (1:1, by volume) | J. Am. Chem. Soc., 75, 4086 (1953). |
| 44 | δ = 2.27(3H, s), 2.71(3H, s), 3.89 (3H, s), 4.15(3H, s), 8.00(1H, s), 8.08 (1H, s). m/z (thermospray) 437 (MH$^+$). | No acid wash. | J. Chem. Soc., 1963, 2032 |
| 45 | δ = 2.16(3H, s), 3.75(3H, s), 4.12 (1H, s), 4.17(1H, s), 6.91(1H, t, J=4Hz), 7.26(1H, obscured), 7.42 (1H, t, J=4Hz), 8.00(1H, s). m/z (thermospray) 430.8 (MH$^+$). | No acid wash. | J. Am. Chem. Soc., 75, 1933 (1953). |
| 46 | δ = 2.15(3H, s), 3.76(3H, s), 3.78 (1H, d, J=15Hz), 4.05(1H, d, J=15Hz), 4.17(3H, s), 6.98(1H, m), 7.30(1H, d, J=9Hz), 7.86(1H, s), 8.06(1H, s), 8.14(1H, d, J=5Hz). m/z (thermospray) 430.8 (MH$^+$). | No acid wash. | Preparation 120 |
| 47 | δ = 2.17(3H, s), 3.78(3H, s), 3.80 (1H, d, J=15Hz), 4.01(1H, d, J=15Hz), 4.17(3H, s), 6.79(2H, d, J=5Hz), 8.05 (1H, s), 8.22(2H, d, J=15Hz). m/z (thermospray) 431.0 (MH$^+$). | No acid wash. | J. Am. Chem. Soc., 1953, 1933. |
| 48 | δ = 2.20(3H, s), 2.22(3H, s), 3.80 (3H, s), 4.16(3H, s), 6.19(1H, broad s), 8.08(1H, s). m/z (thermospray) 420.0 (MH$^+$). | — | — |
| 49 | δ = 2.28(3H, s), 3.03(3H, s), 3.81 (3H, s), 4.18(3H, s), 8.18(1H, s). m/z (thermospray) 437.6 (MH$^+$). | — | — |
| 50 | δ = 2.29(3H, s), 4.00(3H, s), 4.15 (3H, s), 7.09(1H, t, J=8Hz), 7.25(2H, m, obscured), 7.34(1H, d, J=8Hz), 8.01(1H, s). m/z (thermospray) 451.2 (MH$^+$). | — | — |
| 51 | δ = 2.23(3H, s), 2.46(3H, s), 3.97 (3H, s), 4.17(3H, s), 6.89(2H, s), 7.18 (3H, s), 7.99(1H, s). m/z (thermospray) 429.2 (MH$^+$). | — | — |
| 52 | δ = 2.22(3H, s), 2.69(3H, s), 3.96 (3H, s), 4.15(3H, s), 6.96(1H, m), 7.35 (1H, d, J=8Hz), 8.01(1H, s), 8.42(1H, d, J=4Hz). m/z (thermospray) 431.1 (MH$^+$). | No acid wash. | Preparation 118 |
| 53 | δ = 2.28(3H, s), 3.38(3H, s), 3.91 (3H, s), 4.11(3H, s), 6.62(1H, d, J=8Hz), 6.86(1H, t, J=5Hz) 7.25(1H, obscured), 7.51(1H, d, J=8Hz), 7.97 (1H, s). m/z (thermospray) 446.1 (MH$^+$). | — | — |
| 54 | δ = 2.21(3H, s), 2.49(3H, s), 3.82 (3H, s), 4.16(3H, s), 7.19(1H, s), 8.03 (1H, s). m/z (thermospray) 420.0 (MH$^+$). | No acid wash. | Preparation 119 |
| 55 | δ = 2.21(3H, s), 2.48(3H, s), 3.83 (3H, s), 4.16(3H, s), 7.11(1H, d, J=8Hz), 7.83(1H, d, J=8Hz), 8.06 (1H, s), 8.17(1H, s). m/z (thermospray) 431.1 (MH$^+$). | No acid wash. | J. Prak. Chem., 1932, 133 |
| 56 | δ = 2.22(3H, s), 3.65(3H, s), 3.84(3H, s), 4.11(3H, s), 6.82 (2H, m), 7.06(2H, m), 8.05 (1H, s). m/z (thermospray) 446 (MH$^+$). | ethyl acetate | — |
| 57 | δ = 2.03(3H, s), 2.20(3H, s), 3.84(3H, s), 4.15(3H, s), 4.17 (3H, s), 5.25(1H, s), 8.10(1H, s). m/z (thermospray) 434 (MH$^+$) | ethyl acetate | Bull. Pharm. Sci., Assiut Univ., 13(2), 145 (1990). |
| 58 | δ = 2.23(3H, s), 3.83(3H, s), 4.14(3H, s), 7.50(4H, m), 8.08 | gradient elution using hexane: | — |

-continued

| | | | |
|---|---|---|---|
| | (1H, s).<br>m/z (thermospray) 484.5 (MH⁺). | ethyl acetate (1:1 changing to 1:3 changing to 0:1, by volume) | |
| 59 | δ = 0.90(3H, t, J=8Hz), 1.58(2H, m), 2.20(3H, s), 2.50(2H, t, J=6Hz), 3.80(3H, s), 4.13 (3H, s), 6.30(1H, s), 8.06(1H, s).<br>m/z (thermospray) 448.5 (MH⁺). | gradient elution using hexane: ethyl acetate (1:3 changing to 0:1, by volume) | Preparation 123 |
| 60 | δ = 2.18(3H, s), 2.87(6H, s), 3.84(3H, s), 4.13(3H, s), 6.47 (2H, dd, J=8Hz), 7.22(2H, dd, J=8Hz), 8.04(1H, s).<br>m/z (thermospray) 459.5 (MH⁺). | no acid wash; gradient elution using dichloromethane: methanol (100:0 changing to 99:1, by volume) | — |
| 61 | δ = 2.20(3H, s), 3.80(3H, s), 3.83(3H, s), 4.15(3H, s), 6.94 (1H, s), 7.51(1H, s), 8.05(1H, s).<br>m/z (thermospray) 420.3 (MH⁺). | ethyl acetate: methanol (2:98, by volume) | Preparation 124 |
| 62 | δ = 2.22(3H, s), 3.83(3H, s), 4.02(3H, s), 4.17(3H, s), 6.21 (1H, s), 7.48(1H, s), 8.10(1H, s).<br>m/z (thermospray) 419.8 (MH⁺). | no acid wash; gradient elution using ethyl acetate:methanol (100:0 changing to 98:2, by volume) | J. Am. Chem. Soc., 1949, 2444 |
| 63 | δ = 2.20(3H, s), 3.60(3H, s), 3.80(3H, s), 4.16(3H, s), 7.03 (1H, s), 7.50(1H, s), 8.05(1H, s).<br>m/z (thermospray) 420.1 (MH⁺). | no acid wash; gradient elution using ethyl acetate:methanol (100:0 changing to 98:2, by volume) | J. Chem. Soc., 1928, 31 |
| 64 | δ = 2.26(3H, s), 3.79(3H, s), 4.17(3H, s), 8.12(1H, s), 8.15 (1H, br s).<br>m/z (thermospray) 407 (MH⁺). | ethyl acetate | Preparation 126 |
| 65 | δ = 2.23(3H, s), 3.85(3H, s), 4.15(3H, s), 4.23(3H, s), 5.48 (1H, s), 7.2(1H, s), 8.10(1H, s).<br>m/z (thermospray) 420.5 (MH⁺). | ethyl acetate | Preparation 121 |
| 66 | δ = 2.25(3H, s), 3.90(3H, s), 4.20(3H, s), 4.38(3H, s), 7.48 (2H, d, J=10Hz), 7.66(2H, d, J=10Hz), 8.13(1H, s).<br>m/z (thermospray) 528 (MH⁺). | gradient using ethyl acetate: hexane (95:5 changing to 100:0 by volume) | — |
| 67 | δ = 1.24(3H, t, J=7Hz), 2.24 (3H, s), 3.82(3H, s), 4.16 (3H, s), 4.24(2H, q, J=7Hz), 8.07(1H, s).<br>m/z (thermospray) 412 (MH⁺). | — | J. Prak. Chem., 91, 431 (1915). |
| 68 | δ = 1.17(3H, t, J=5Hz), 2.19 (3H, s), 3.53(1H, d, J=14Hz), 3.66(1H, d, J=14Hz), 3.91 (3H, s), 3.93(2H, q, obscured), 4.18(3H, s), 8.08(1H, s).<br>m/z (thermospray) 426 (MH⁺). | — | J. Prak. Chem., 125, 218 (1930). |
| 69 | δ = 2.23(3H, s), 3.81(3H, s), 4.12(3H, s), 4.16(3H, s), 7.03 (1H, s), 7.50(1H, s), 8.05 (1H, s).<br>m/z (thermospray) 420 (MH⁺). | no acid wash. | Preparation 125 |
| 70 | δ = 2.27(3H, s), 3.78(3H, s), 4.14(3H, s), 4.38(3H, s), 7.53 (1H, s), 8.08(1H, s).<br>m/z (thermospray) 421 (MH⁺). | no acid wash; gradient elution using hexane: ethyl acetate (1:1 changing to 1:3 changing to 0:1, by volume) | Preparation 128 |
| 71 | δ = 2.28(3H, s), 3.80(3H, s), 4.17(3H, s), 5.26(2H, br s), 8.09(1H, s).<br>m/z (thermospray) 423 (MH⁺). | no acid wash; ethyl acetate | Preparation 122 |
| 72 | δ = 2.21(3H, s), 3.82(3H, s), 4.15(3H, s), 7.43(2H, s), 8.11 (1H, s).<br>m/z (thermospray) 406 (MH⁺). | no acid wash; gradient elution using ethyl acetate: | Preparation 127 |

| | | | |
|---|---|---|---|
| | | methanol (1:0 changing to 95:5, by volume) | |
| 73 | δ = 2.21(3H, s), 3.82(3H, s), 4.17(3H, s), 6.83(1H, m), 6.92(1H, d, J=4Hz), 7.21(1H, d, J=5Hz), 8.12(1H, s). m/z (thermospray) 422 (MH$^+$). | no acid wash; gradient elution using hexane: ethyl acetate (70:30 changing to 25:75, by volume) | — |
| 74 | δ = 2.23(3H, s), 3.77(3H, s), 4.16(3H, s), 6.42(2H, m), 7.03(1H, d, J=5Hz), 7.17 (1H, m), 8.18(1H, s). m/z (thermospray) 432 (MH$^+$). | no acid wash; gradient elution using hexane: ethyl acetate (90:10 changing to 3:1, by volume) | — |
| 75 | δ = 2.40(3H, s), 3.82(3H, s), 4.17(3H, s), 7.22(2H, d, J=6Hz), 7.30(2H, d, J=6Hz), 8.13(1H, s). m/z (thermospray) 450 (MH$^+$). | no acid wash; gradient elution using hexane: ethyl acetate (2:3 changing to 1:4, by volume) | — |
| 76 | δ = 2.23(3H, s), 3.73(3H, s), 3.85(3H, s), 4.15(3H, s), 6.74 (2H, d, J=5Hz), 7.29(2H, d, J=5Hz), 8.07(1H, s). m/z (thermospray) 446 (MH$^+$). | no acid wash; gradient elution using hexane: ethyl acetate (3:7 changing to 0:1, by volume) | — |
| 77 | δ = 2.14(6H, s), 3.88(3H, s), 4.18(3H, s), 8.18(1H, s). m/z (thermospray) 354 (MH$^+$). | no acid wash; gradient elution using ethyl acetate: methanol (1:0 changing to 95:5, by volume) | — |
| 78 | δ = 2.25(3H, s), 3.86(3H, s), 4.15(3H, s), 8.07(1H, s), 8.12 (1H, s). m/z (thermospray) 340 (MH$^+$). | no acid wash; gradient elution using ethyl acetate: methanol (1:0 changing to 94:6, by volume) | — |
| 79 | δ = 1.0(5H, m), 2.14(3H, s), 3.86 (3H, s), 4.15(3H, s), 8.09(1H, s). m/z (thermospray) 380 (MH$^+$). | no acid wash; gradient elution using ethyl acetate: methanol (1:0 changing to 95:5, by volume) | — |
| 80 | δ = 2.20(3H, s), 3.82(3H, s), 4.10 (3H, s), 7.22(3H, m), 7.35(2H, m), 8.06(1H, s). m/z (thermospray) 416 (MH$^+$). | no acid wash; gradient elution using ethyl acetate: methanol (1:0 changing to 97:3, by volume) | — |
| 81 | δ = 1.98(3H, s), 4.00(3H, s), 4.15(3H, s), 8.05(1H, s), 8.74(1H, s). m/z (thermospray) 356 (MH$^+$). | no acid wash; hexane:ethyl acetate (1:1 by volume) | — |
| 82 | δ = 2.05(3H, s), 3.20(3H, s), 3.82 (3H, s), 4.15(6H, s), 4.37(1H, d, J=13Hz), 4.47(1H, d, J=13Hz), 5.28 (1H, s, obscured), 8.08(1H, s). m/z (thermospray) 464.4 (MH$^+$). | gradient elution using hexane:ethyl acetate (3:1 changing to 1:3 changing to 0:1, by volume) | Bull. Pharm. Sci., Assiut Univ., 13(2), 145 (1990). |
| 83 | δ = 3.20(3H, s), 3.95(3H, s), 4.14 (3H, s), 4.45(1H, d, J=14Hz), 4.56 (1H, d, J=14Hz), 7.10(1H, m), 7.20–7.35(3H, m, obscured), 7.95 (1H, s). m/z (thermospray) 480.3 (MH$^+$). | gradient elution using hexane:ethyl acetate (3:1 changing to 1:3 changing to 0:1, by volume) | — |
| 84 | δ = 3.15(3H, s), 3.70(3H, s), 3.79 (1H, d, J=15Hz), 4.08(1H, d, J=15Hz), 4.15(3H, s), 4.28(1H, d, J=12Hz), 4.40(1H, d, J=12Hz), 6.90(1H, m), 7.85(1H, d, J=3Hz), 8.03(1H, s), 8.21 (1H, d, J=5Hz). m/z (thermospray) 461.4 (MH$^+$). | no acid wash; ethyl acetate: methanol (95:5, by volume) | — |
| 85 | δ = 2.50(3H, s), 3.18(3H, s), 3.84(3H, s), 4.14(3H, s), 4.48 (2H, m), 7.10(1H, m), 7.80 | no acid wash. | J. Prakt. Chem., 1932, 133 |

| | | | |
|---|---|---|---|
| | (1H, m), 8.04(1H, s), 8.32 (1H, m). m/z (thermospray) 461 (MH$^+$). | | |
| 86 | δ = 3.06(3H, s), 3.78(3H, s), 4.06(3H, s), 4.08(3H, s), 4.40 (2H, m), 5.60(1H, m), 7.28 (1H, m), 8.22(1H, s). m/z (thermospray) 450 (MH$^+$). | no acid wash; gradient elution using dichloromethane: methanol (1:0 changing to 98:2, by volume) | Preparation 121 |
| 87 | δ = 3.16(6H, s), 3.82(3H, s), 4.16(3H, s), 4.40(4H, m), 8.08(1H, s). m/z (thermospray) 414 (MH$^+$). | no acid wash; gradient elution using dichloromethane: methanol (1:0 changing to 98:2, by volume) | — |
| 88 | δ = 2.34(3H, s), 3.20(3H, s), 3.78(3H, s), 4.14(3H, s), 4.48 (2H, m), 7.70(1H, s), 8.04 (1H, s). m/z (thermospray) 467 (MH$^+$). | no acid wash; gradient elution using dichloromethane: methanol (1:0 changing to 99:1, by volume) | Aust. J. Chem., 38(8), 1257 (1985) |
| 89 | Analysis (%): Found: C, 49.78; H, 3.60; N, 16.50. $C_{21}H_{18}Cl_2N_6O_2$ requires C, 49.92; H, 3.59; N, 16.63. | no acid wash; dichloromethane: methanol (99:1, by volume) | Preparation 116 |
| 90 | δ = 2.74(2H, m), 3.20(3H, s), 3.72(2H, m), 3.84(3H, s), 4.16 (3H, s), 7.20(1H, m), 7.84 (1H, m), 8.08(1H, s), 8.42 (1H, m), 8.52(1H, m). m/z (thermospray) 461 (MH$^+$). | no acid wash; gradient elution using dichloromethane: methanol (1:0 changing to 98:2, by volume) | — |
| 91 | δ = 1.98(2H, m), 2.38(2H, m), 2.46(1H, m), 2.62(1H, m), 3.56 (3H, s), 3.84(3H, s), 4.16 (3H, s), 7.20(1H, m), 7.82 (1H, m), 8.06(1H, s), 8.44 (1H, s), 8.50(1H, m). m/z (APCI) 503 (MH$^+$). | no acid wash; gradient elution using dichloromethane: methanol (1:0 changing to 99:1, by volume) | — |
| 92 | δ = 1.26(3H, t, J=5Hz), 3.84 (3H, s), 4.15(3H, s), 4.27 (2H, q, J=5Hz), 8.04(1H, s), 8.30(1H, s). m/z (thermospray) 398 (MH$^+$). | gradient elution using dichloromethane: methanol (1:0 changing to 98:2, by volume) | — |
| 93 | δ = 1.24(3H, t, J=5Hz), 3.80 (3H, s), 4.12(3H, s), 4.26 (2H, q, J=5Hz), 7.24(2H, m), 7.35(1H, m), 7.40(2H, m), 8.05 (1H, s). m/z (thermospray) 474 (MH$^+$). | gradient elution using hexane: ethyl acetate (7:3 changing to 3:2, by volume) | — |
| 94 | δ = 1.23(3H, t, J=5Hz), 3.80 (3H, s), 4.10(3H, s), 4.25 (2H, q, J=5Hz), 7.20(1H, m, obscured), 7.83(1H, m), 8.03 (1H, s), 8.51(1H, m), 8.60 (1H, m). m/z (thermospray) 475 (MH$^+$). | no acid wash; dichloromethane: methanol (99:1, by volume) | — |
| 95 | δ = 3.84(3H, s), 4.12(3H, s), 7.28(6H, m), 7.38(4H, m), 8.00 (1H, s). m/z (thermospray) 478 (MH$^+$). | hexane:ethyl acetate (3:1, by volume) | |

Notes
1) Prepared using ethyl carbazate as the "hydrazide" starting material. The final cyclisation was effected by heating in xylene.
2) The product was an unexpected product from the reaction of the hydrazide from Preparation 118.

PREPARATION 96

6,7-Dichloro-2,3-dimethoxy-5-[3-(3-methyl-1,2,4-oxadiazol-5-yl)-5-(3-pyridyl)-4H-1,2,4-triazol-4-yl]quinoxaline

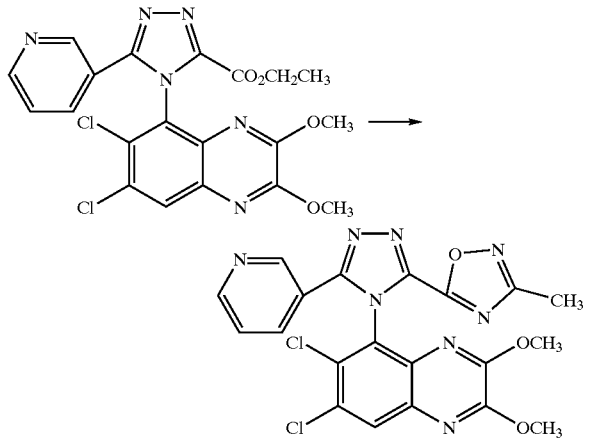

Acetamide oxime (120 mg, 1.62 mmol) followed by sodium hydride (80% w/w dispersion in oil, 8 mg, 0.27 mmol) were added to a stirred suspension of 6,7-dichloro-2,3-dimethoxy-5-[3-ethoxycarbonyl-5-(3-pyridyl)-4H-1,2,4-triazol-4-yl]quinoxaline (Preparation 94, 250 mg, 0.53 mmol) in dry toluene (15 mL) at room temperature under nitrogen. The mixture was heated under reflux for 3.5 hours, cooled and the solution partitioned between ethyl acetate and brine. The aqueous phase was extracted with ethyl acetate (2×20 mL), the combined organic extracts dried (MgSO$_4$) and concentrated under reduced pressure. The residue was purified by flash chromatography on silica gel, by gradient elution using hexane:ethyl acetate (7:3 changing to 1:1, by volume) to give the title compound (210 mg, 82%) as a white solid.

$^1$H-NMR (300 MHz, CDCl$_3$): δ=2.25 (3H, s), 3.77 (3H, s), 4.14 (3H, s), 7.28 (1H, m, obscured), 7.93 (1H, m), 8.10 (1H, s), 8.58 (2H, m).

m/z (thermospray) 485 (MH$^+$).

PREPARATION 97

6,7-Dichloro-2,3-dimethoxy-5-[5-methyl-3-(3-methyl-1,2,4-oxadiazol-5-yl)-4H-1,2,4-triazol-4-yl]quinoxaline

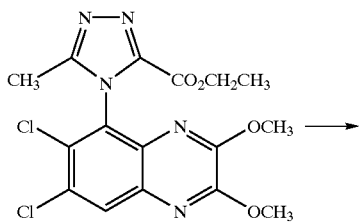

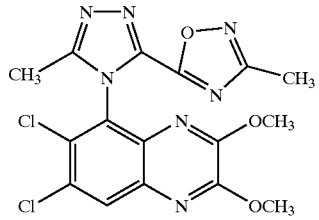

The title compound was prepared by a similar method to that of Preparation 96 using 6,7-dichloro-2,3-dimethoxy-5-(3-ethoxycarbonyl-5-methyl-4H-1,2,4-triazol-4-yl)quinoxaline (Preparation 67) in place of 6,7-dichloro-2,3-dimethoxy-5-[3-ethoxycarbonyl-5-(3-pyridyl)-4H-1,2,4-triazol-4-yl]quinoxaline. Purification by flash chromatography on silica gel, by gradient elution using dichloromethane:methanol (1:0 changing to 95:5, by volume) gave a white solid.

$^1$H-NMR (300 MHz, CDCl$_3$): δ=2.26 (3H, s), 2.33 (3H, s), 3.79 (3H, s), 4.20 (3H, s), 8.15 (1H, s).

m/z (thermospray) 422 (MH$^+$).

PREPARATION 98

6,7-Dichloro-2,3-dimethoxy-5-[3-(3-pyridyl)-4H-1,2,4-triazol-4-yl]quinoxaline

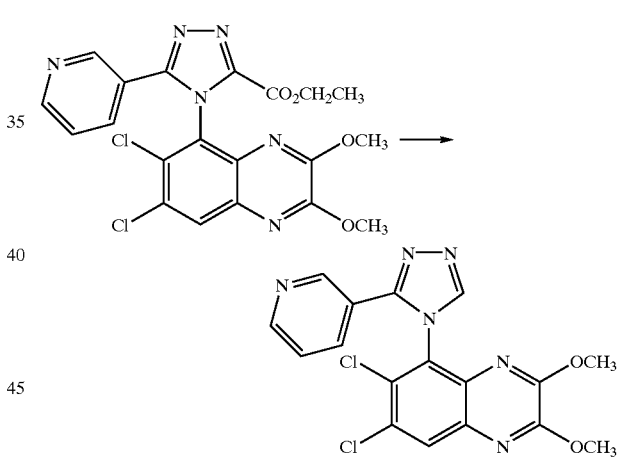

1M Aqueous sodium hydroxide solution (17.25 mL, 17.25 mmol) was added dropwise to a stirred solution of 6,7-dichloro-2,3-dimethoxy-5-[3-ethoxycarbonyl-5-(3-pyridyl)-4H-1,2,4-triazol-4-yl]quinoxaline (Preparation 94, 8.2 g, 17.25 mmol) in 1,4-dioxane (68 mL) and water (50 mL) at 10° C. The solution was warmed to room temperature and stirred for 20 hours, diluted with water (50 mL), acidified with glacial acetic acid and extracted with ethyl acetate (1×100 mL, 2×50 mL). The combined organic extracts were washed with brine, dried (MgSO$_4$) and concentrated under reduced pressure. The residue was purified by flash chromatography on silica gel, by gradient elution using dichloromethane:methanol (1:0 changing to 9:1, by volume) to give the title compound (5.82 g, 84%) as a white solid, mp 206–207° C.

Analysis (%): Found C, 50.49; H, 3.06; N, 20.44. C$_{17}$H$_{12}$Cl$_2$N$_6$O$_2$ requires: C, 50.63; H, 3.00; N, 20.84.

PREPARATION 99

6.7-Dichloro-2,3-dimethoxy-5-[5-bromo-3-(3-pyridyl)-4H-1,2,4-triazol-4-yl]quinoxaline

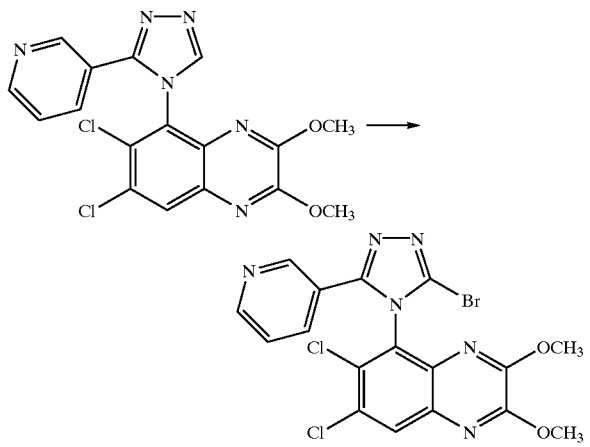

N-Bromosuccinimide (58 mg, 0.33 mmol) was added to a stirred suspension of 6,7-dichloro-2,3-dimethoxy-5-[3-(3-pyridyl)-4H-1,2,4-triazol-4-yl]quinoxaline (Preparation 98, 102 mg, 0.25 mmol) in 1,1,1-trichloroethane (6 mL) at room temperature under nitrogen and the mixture was heated under reflux for 18 hours. The mixture was concentrated under reduced pressure and the residue purified by flash chromatography on silica gel, by gradient elution using hexane:ethyl acetate (7:3 changing to 1:1, by volume) to give the title compound (87 mg, 71%) as a white solid.

$^1$H-NMR (300 MHz, CDCl$_3$): δ=3.86 (3H, s), 4.16 (3H, s), 7.28 (1H, m, obscured), 7.88 (1H, m), 8.12 (1H, s), 8.49 (1H, m), 8.58 (1H, m).

m/z (thermospray) 481 (MH$^+$).

PREPARATION 100

6,7-Dichloro-2,3-dimethoxy-5-[3-(1-imidazolyl)-5-methyl-4H-1,2,4-triazol-4-yl]quinoxaline

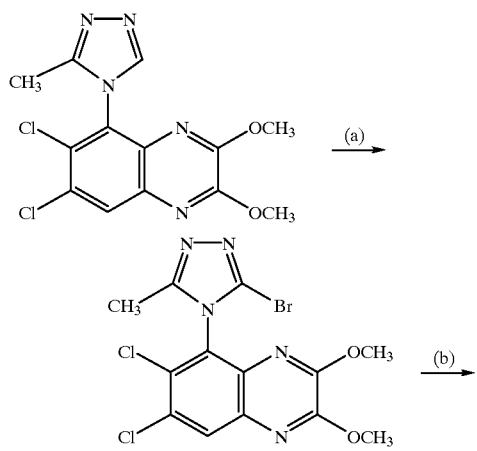

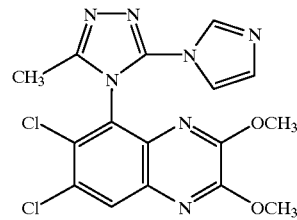

(a) 6,7-Dichloro-2,3-dimethoxy-5-(3-bromo-5-methyl-4H-1,2,4-triazol-4-yl)quinoxaline was prepared by a similar method to that of Preparation 99 using 6,7-dichloro-2,3-dimethoxy-5-(3-methyl-4H-1,2,4-triazol-4-yl)quinoxaline (Preparation 78, 50 mg, 0.147 mmol) in place of 6,7-dichloro-2,3-dimethoxy-5-[3-(3-pyridyl)-4H-1,2,4-triazol-4-yl]quinoxaline. It was obtained as a pale brown solid (53 mg, 86%).

$^1$H-NMR (300 MHz, DMSO-d$_6$): δ=2.27 (3H, s), 3.91 (3H, s), 4.19 (3H, s), 8.16 (1H, s).

m/z (thermospray) 419 (MH$^+$).

(b) A mixture of imidazole (78 mg, 1.15 mmol) and 6,7-dichloro-2,3-dimethoxy-5-(3-bromo-5-methyl-4H-1,2,4-triazol-4-yl)quinoxaline (48 mg, 0.115 mmol) was heated at 100° C. for 1 hour then at 120° C. for 3 hours. After being cooled the mixture was partitioned between water (15 mL) and dichloromethane (2×15 mL). The combined organic extracts were dried (MgSO$_4$), filtered and concentrated under reduced pressure. The residue was purified by flash chromatography on silica gel, by gradient elution using dichloromethane:methanol (98:2 changing to 95:5, by volume) to give the title compound (15 mg, 32%) as a brown solid.

$^1$H-NMR (300 MHz, DMSO-d$_6$): δ=2.27 (3H, s), 4.11 (6H, s), 7.16 (2H, br s), 7.79 (1H, br s), 7.95 (1H, s).

m/z (thermospray) 406 (MH$^+$).

PREPARATION 101

6,7-Dichloro-2,3-dimethoxy-5-[3-hydroxymethyl-5-(3-pyridyl)-4H-1,2,4-triazol-4-yl]quinoxaline

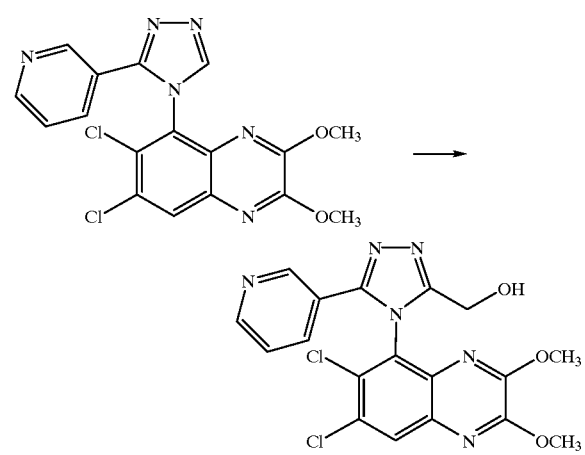

A suspension of 6,7-dichloro-2,3-dimethoxy-5-[3-(3-pyridyl)-4H-1,2,4-triazol-4-yl]quinoxaline (Preparation 98, 1.008 g, 2.5 mmol) and paraformaldehyde (0.75 g, 25 mmol) in acetic acid (14 mL) was heated at 125° C. for 3 hours in a sealed vessel. After being cooled, the mixture was concentrated under reduced pressure and the residue was purified by flash chromatography on silica gel, by gradient elution using dichloromethane:methanol (1:0 changing to 95:5, by volume) to afford the title compound (0.60 g, 56%) as a white solid, mp 209–210° C.

Analysis (%): Found: C, 49.86; H, 3.31; N, 19.18. $C_{18}H_{14}Cl_2N_6O_3$ requires: C, 49.90; H, 3.26; N, 19.39.

PREPARATION 102

6,7-Dichloro-2,3-dimethoxy-5-[3-hydroxymethyl-5-methyl-4H-1,2,4-triazol-4-yl]quinoxaline

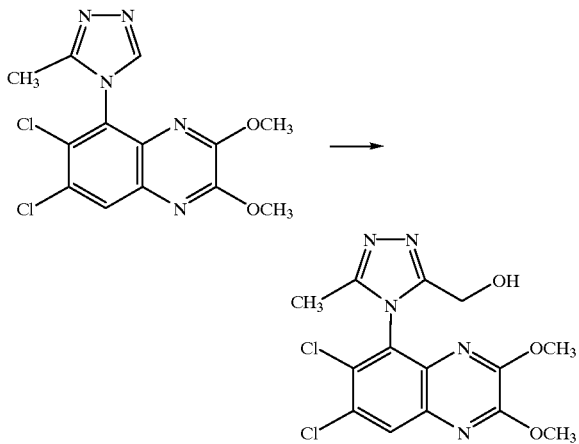

The title compound was prepared as a white solid by a similar method to that of Preparation 101 using 6,7-dichloro-2,3-dimethoxy-5-(3-methyl-4H-1,2,4-triazol-4-yl) quinoxaline (Preparation 78) in place of 6,7-dichloro-2,3-dimethoxy-5-[3-(3-pyridyl)-4H-1,2,4-triazol-4-yl] quinoxaline.

$^1$H-NMR (300 MHz, DMSO-$d_6$): δ=2.20 (3H, s), 3.89 (3H, s), 4.18 (3H, s), 4.54 (2H, s), 8.11 (1H, s).

m/z (thermospray) 370 (MH$^+$).

PREPARATION 103

6,7-Dichloro-2,3-dimethoxy-5-[3-dimethylaminomethyl-5-(3-pyridyl)-4H-1,2,4-triazol-4-yl]quinoxaline

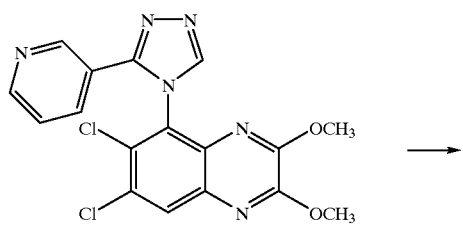

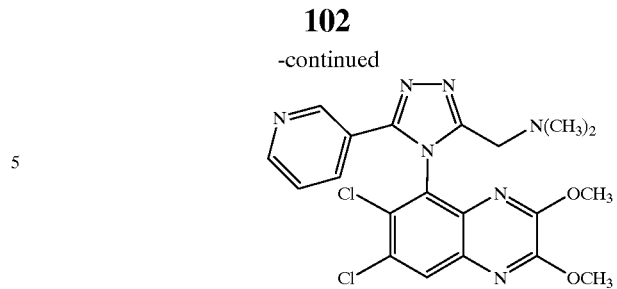

A mixture of 6,7-dichloro-2,3-dimethoxy-5-[3-(3-pyridyl)-4H-1,2,4-triazol-4-yl]quinoxaline (Preparation 98, 101 mg, 0.25 mmol), paraformaldehyde (15 mg, 0.5 mmol) and dimethylamine hydrochloride (22 mg, 0.27 mmol) in acetic acid (5 mL) was heated under reflux for 5 hours. After being cooled, the mixture was concentrated under reduced pressure, water (20 mL) was added, the solution basified with aqueous potassium carbonate solution and extracted with ethyl acetate (3×20 mL). The combined organic extracts were dried (MgSO$_4$) and concentrated under reduced pressure. The residue was purified by flash chromatography on silica gel, by gradient elution using dichloromethane:methanol (1:0 changing to 95:5, by volume) to afford the title compound (75 mg, 65%) as a white solid, mp 192–194° C.

$^1$H-NMR (300 MHz, CDCl$_3$): δ=2.0 (6H, s), 3.48 (2H, m), 3.82 (3H, s), 4.15 (3H, s), 7.2 (1H, m), 7.85 (1H, m), 8.05 (1H, s), 8.5 (2H, m).

m/z (thermospray) 460 (MH$^+$).

PREPARATION 104

6,7-Dichloro-2,3-dimethoxy-5-[3-morpholinomethyl-5-(3-pyridyl)-4H-1,2,4-triazol-4-yl]quinoxaline

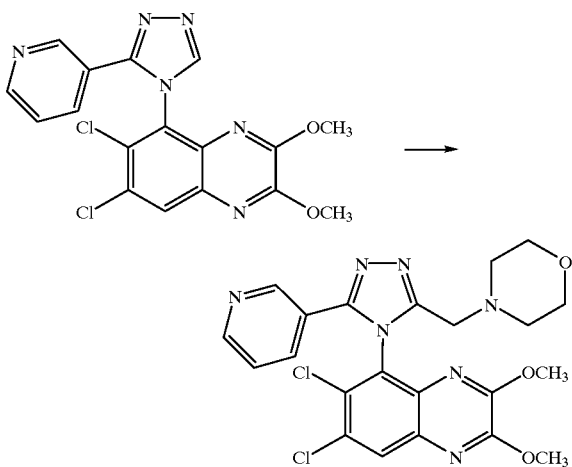

The title compound was prepared by a similar method to that of Preparation 103, using morpholine hydrochloride in place of dimethylamine hydrochloride. It was obtained as a white solid, mp 178–179° C.

$^1$H-NMR (300 MHz, CDCl$_3$): δ=2.10 (4H, m), 3.10 (4H, m), 3.56 (2H, m), 3.80 (3H, s), 4.18 (3H, s), 7.21 (1H, m), 7.80 (1H, m), 8.05 (1H, s), 8.55 (2H, m).

m/z (thermospray) 502 (MH$^+$).

PREPARATION 105

6,7-Dichloro-2,3-dimethoxy-5-(3-hydroxymethyl-5-phenyl-4H-1,2,4-triazol-4-yl)quinoxaline

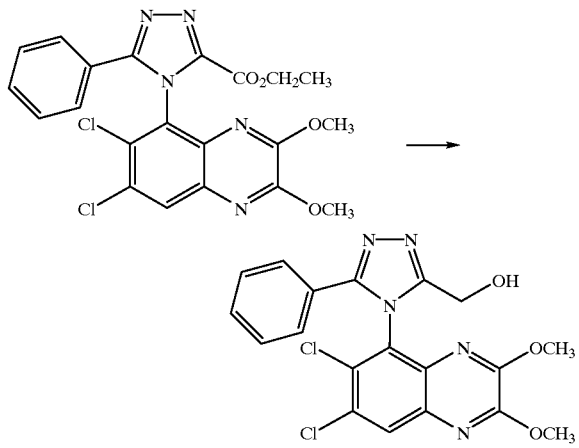

Diisobutylaluminium hydride (1M in tetrahydrofuran, 2.5 mL, 2.5 mmol) was added to a solution of 6,7-dichloro-2,3-dimethoxy-5-(3-ethoxycarbonyl-5-phenyl-4H-1,2,4-triazol-4-yl)quinoxaline (Preparation 93, 237 mg, 0.5 mmol) in dichloromethane (10 mL) at room temperature under nitrogen. After 1 hour, a further portion of diisobutylaluminium hydride (1M in tetrahydrofuran, 1 mL, 1 mmol) was added, the mixture was stirred for a further 1 hour, then saturated aqueous ammonium chloride solution (10 mL) was added. Dichloromethane (50 mL) and water (50 mL) were added and the mixture was filtered through ARBOCEL (trade mark), washing the residue with warm dichloromethane:methanol (9:1, by volume, 100 mL). The organic layer was separated, dried (MgSO$_4$) and evaporated under reduced pressure. The residue was purified by flash chromatography on silica gel, by gradient elution using hexane:ethyl acetate:methanol (1:1:0 changing to 0:1:0 changing to 0:95:5, by volume) to give the title compound (70 mg, 79%) as an off-white solid.

$^1$H-NMR (300 MHz, CDCl$_3$): δ=2.78 (1H, s), 3.85 (3H, s), 4.14 (3H, s), 4.6 (2H, m), 7.25 (2H, m), 7.32 (2H, m), 7.38 (1H, m), 8.08 (1H, s).

m/z (thermospray) 432 (MH$^+$).

PREPARATION 106

6,7-Dichloro-2,3-dimethoxy-5-(3-hydroxymethyl-4H-1,2,4-triazol-4-yl)quinoxaline

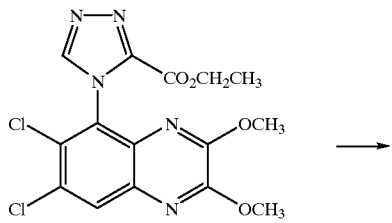

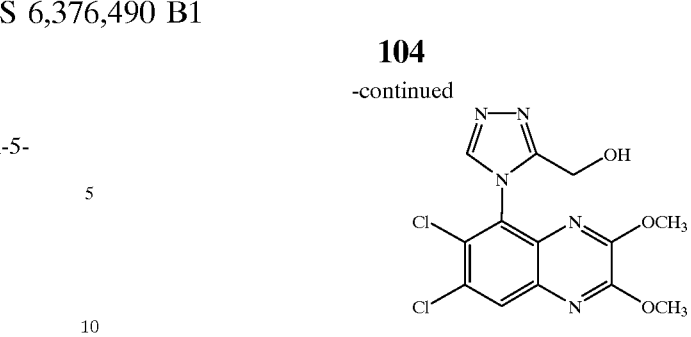

The title compound was prepared as an off-white solid by a similar method to that of Preparation 105 using 6,7-dichloro-2,3-dimethoxy-5-(3-ethoxycarbonyl-4H-1,2,4-triazol-4-yl)quinoxaline (Preparation 92) in place of 6,7-dichloro-2,3-dimethoxy-5-(3-ethoxycarbonyl-5-phenyl-4H-1,2,4-triazol-4-yl)quinoxaline.

$^1$H-NMR (300 MHz, CDCl$_3$): δ=3.89 (3H, s), 4.14 (3H, s), 4.64 (2H, m), 8.08 (1H, s, 8.16 (1H, s).

m/z (thermospray) 356 (MH$^+$).

PREPARATION 107

6,7-Dichloro-2,3-dimethoxy-5-[3-(2-hydroxyethyl)-5-methyl-4H-1,2,4-triazol-4-yl]quinoxaline

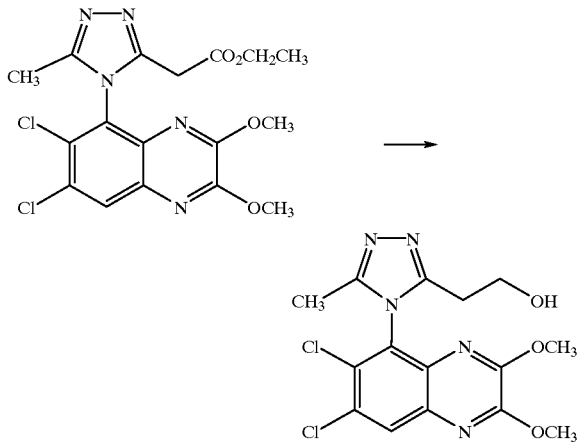

The title compound was prepared by a similar method to that of Preparation 105 using 6,7-dichloro-2,3-dimethoxy-5-[3-ethoxycarbonylmethyl-5-methyl-4H-1,2,4-triazol-4-yl]quinoxaline (Preparation 68) in place of 6,7-dichloro-2,3-dimethoxy-5-(3-ethoxycarbonyl-5-phenyl-4H-1,2,4-triazol-4-yl)quinoxaline. The reaction was carried out in toluene instead of dichloromethane and purification was by flash chromatography on silica gel, by gradient elution using dichloromethane:methanol (1:0 changing to 95:5, by volume). Crystallisation from diisopropyl ether gave an off-white solid.

$^1$H-NMR (300 MHz, CDCl$_3$): δ=2.1 (3H, s), 2.5 (2H, m), 3.5 (2H, m), 3.9 (3H, s), 4.18 (3H, s), 8.1 (1H, s).

m/z (thermospray) 384 (MH$^+$).

PREPARATION 108

6,7-Dichloro-2,3-dimethoxy-5-iodoquinoxaline

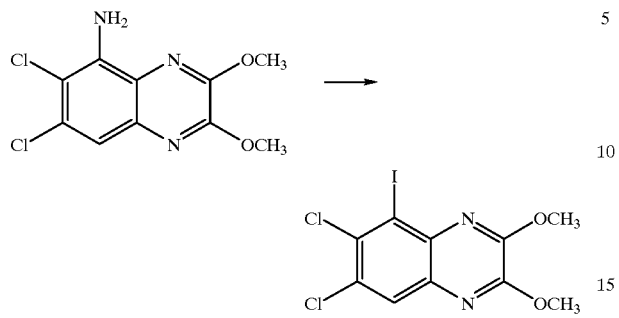

To a mechanically stirred solution of 5-amino-6,7-dichloro-2,3-dimethoxyquinoxaline (Preparation 26, 38.12 g, 0.14 mol) in acetone at 0° C. was added 2M aqueous hydrochloric acid solution (396 mL, 0.79 mol), followed dropwise by addition of 1M aqueous sodium nitrite solution (208 mL, 0.28 mol). After 0.25 hour at 0° C., 5M aqueous potassium iodide solution (278 mL, 1.39 mol) was added maintaining the reaction temperature below 5° C. The mixture was then warmed to 10° C. over 0.5 hour, the acetone removed under reduced pressure and the residue partitioned between water and ethyl acetate. The organic extract was washed with 10% aqueous sodium bisulphite solution, then saturated aqueous sodium bicarbonate solution, dried ($MgSO_4$) and concentrated under reduced pressure. The residue was purified by flash chromatography on silica gel, eluting with toluene to give the title compound (16.9 g, 32%).

$^1$H-NMR (300 MHz, $CDCl_3$): δ=4.17 (3H, s), 4.24 (3H, s), 7.91 (1H, s).

PREPARATION 109

6,7-Dichloro-2,3-dimethoxy-5-(3-pyridyl)quinoxaline

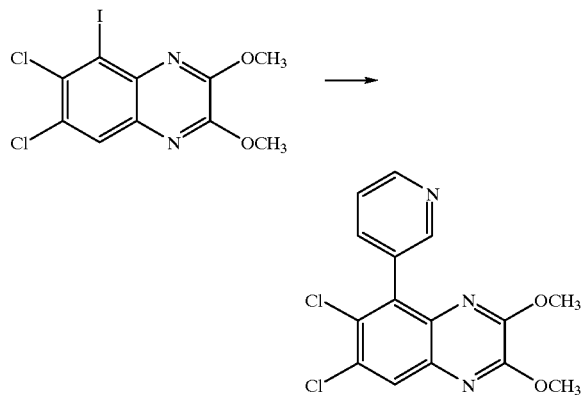

A mixture of 6,7-dichloro-2,3-dimethoxy-5-iodoquinoxaline (Preparation 108, 0.2 g, 0.519 mmol), 3-pyridylboronic acid (*Rec. Trav. Chim. Pays-Bas.* 84, 439 (1965)) (0.077 g, 0.623 mmol), tetrakis(triphenylphosphine)palladium(0) (0.03 g, 0.026 mmol) and potassium carbonate (0.143 g, 1.038 mmol) in 1,4-dioxane (12 mL) and water (4 mL) was heated under reflux for 16 hours. After being cooled, the mixture was concentrated under reduced pressure and the residue partitioned between ethyl acetate (20 mL) and water (20 mL). The phases were separated and the aqueous phase extracted with ethyl acetate (2×40 mL). The combined organic extracts were dried ($MgSO_4$) and concentrated under reduced pressure. The residue was purified by flash chromatography on silica gel, by gradient elution using dichloromethane:methanol (1:0 changing to 99:1, by volume) to afford the title compound (0.051 g, 29%) as a yellow solid.

$^1$H-NMR (300 MHz, $CDCl_3$): δ=3.84 (3H, s), 4.18 (3H, s), 7.42 (1H, m), 7.75 (1H, m), 7.99 (1H, s), 8.63 (2H, m).

m/z (thermospray) 336 ($MH^+$).

PREPARATION 110

6,7-Dichloro-2,3-dimethoxy-5-[5-phenyl-1H-1,2,3-triazol-4-yl]quinoxaline

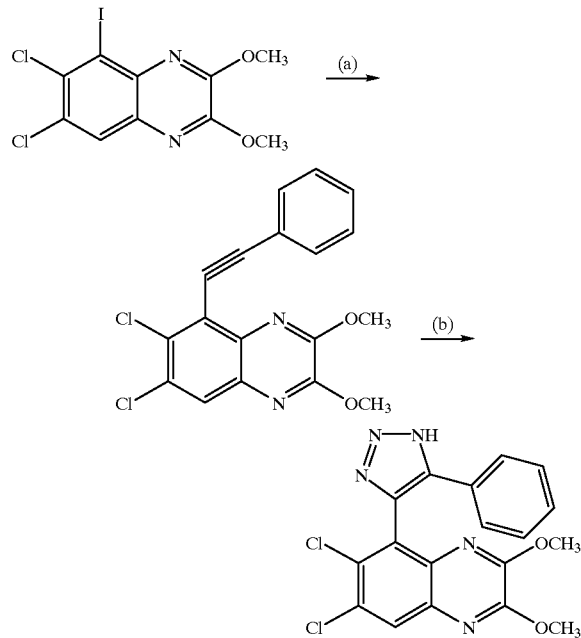

(a) A mixture of 6,7-dichloro-2,3-dimethoxy-5-iodoquinoxaline (Preparation 108, 5.0 g, 13 mmol), phenylacetylene (3.98 g, 39 mmol), bis(triphenylphosphine)palladium(II) chloride (0.913 g, 1.3 mmol) and copper(I) iodide (0.248 g, 1.3 mmol) in triethylamine (100 mL) was heated under reflux for 4 hours. After being cooled, the mixture was concentrated under reduced pressure and the residue partitioned between dichloromethane (200 mL) and brine (200 mL). The phases were separated and the aqueous phase extracted with dichloromethane (2×100 mL). The combined organic extracts were dried ($MgSO_4$) and concentrated under reduced pressure. The residue was purified by flash chromatography on silica gel, by gradient elution using hexane:dichloromethane (1:0 changing to 1:1, by volume) to afford 6,7-dichloro-2,3-dimethoxy-5-(2-phenylethynyl)quinoxaline (3.60 g, 77%) as a yellow solid, mp 170–172° C.

$^1$H-NMR (300 MHz, $CDCl_3$): δ=4.14 (3H, s), 4.26 (3H, s), 7.39 (3H, m), 7.67 (2H, m), 7.87 (1H, s).

m/z (thermospray) 359 ($MH^+$).

(b) A mixture of 6,7-dichloro-2,3-dimethoxy-5-(2-phenylethynyl)quinoxaline (2.0 g, 5.57 mmol) and trimethylsilyl azide (20 mL) was heated at 170° C. in a sealed vessel for 18 hours. After cooling, water (20 mL) was added followed by saturated aqueous sodium hydrogen carbonate solution (50 mL) and the mixture extracted with ethyl acetate (3×50 mL). The combined organic extracts were dried (MgSO$_4$) and concentrated under reduced pressure. The residue was purified by flash chromatography on silica gel, by gradient elution using dichloromethane:methanol (1:0 changing to 98:2, by volume) to afford the title compound (1.3 g, 58%) as a brown foam.

$^1$H-NMR (300 MHz, CDCl$_3$): δ=3.67 (3H, s), 4.13 (3H, s), 7.23 (3H, m), 7.40 (2H, m), 8.02 (1H, s).

m/z (thermospray) 402 (MH$^+$).

PREPARATION 111

6,7-Dichloro-2,3-dimethoxy-5-[2-methyl-5-phenyl-2H-1,2,3-triazol-4-yl]quinoxaline (isomer 1), 6,7-dichloro-2,3-dimethoxy-5-[1-methyl-5-phenyl-1H-1,2,3-triazol-4-yl]quinoxaline (isomer 2) and 6,7-dichloro-2,3-dimethoxy-5-[1-methyl-4-phenyl-1H-1,2,3-triazol-5-yl]quinoxaline (isomer 3)

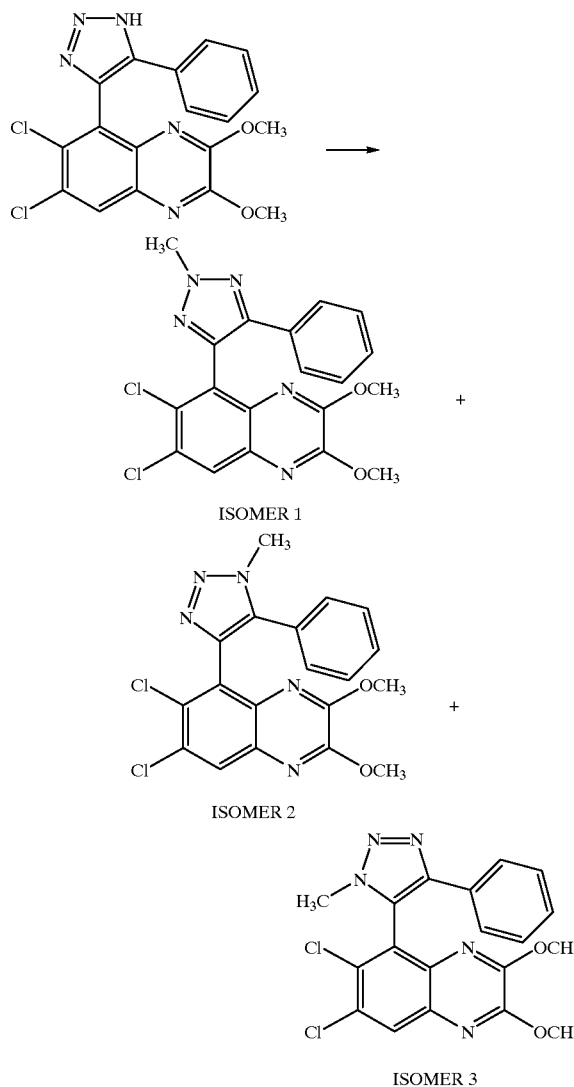

Sodium hydride (80% w/w dispersion in oil, 0.041 g, 1.37 mmol) was added to a stirred solution of 6,7-dichloro-2,3-dimethoxy-5-[5-phenyl-1H-1,2,3-triazol-4-yl]quinoxaline (Preparation 110, 0.5 g, 1.24 mmol) in dry N,N-dimethylformamide (20 mL) at 0° C., under nitrogen. After 0.5 hour at 0° C., iodomethane (0.194 g, 1.37 mmol) was added. The mixture was stirred at 0° C. for 0.5 hour and then at room temperature for 0.5 hour. Brine (50 mL) was added and the mixture extracted with dichloromethane (3×50 mL). The combined organic extracts were dried (MgSO$_4$) and concentrated under reduced pressure. The residue was purified by flash chromatography on silica gel, by gradient elution using toluene:ethyl acetate (1:0 changing to 9:1, by volume) to afford as the first eluted product, isomer 1, tentatively assigned as 6,7-dichloro-2,3-dimethoxy-5-[2-methyl-5-phenyl-2H-1,2,3-triazol-4-yl]quinoxaline (0.19 g, 37%) was a pale yellow solid, mp 233–235° C.

$^1$H-NMR (300 MHz, CDCl$_3$): δ=3.67 (3H, s), 4.14 (3H, s), 4.38 (3H, s), 7.23 (3H, m), 7.38 (2H, m), 8.05 (1H, s).

m/z (thermospray) 416 (MH$^+$).

The second eluted product, isomer 2, tentatively assigned as 6,7-dichloro-2,3-dimethoxy-5-[1-methyl-5-phenyl-1H-1,2,3-triazol-4-yl]quinoxaline (0.135 g, 26%), was obtained as a pale yellow solid, mp 189–190° C.

$^1$H-NMR (300 MHz, CDCl$_3$): δ=3.75 (3H, s), 3.84 (3H, s), 4.17 (3H, s), 7.26 (3H, m), 7.48 (2H, m), 8.13 (1H, s).

m/z (thermospray) 416 (MH$^+$).

The third eluted product, isomer 3, tentatively assigned as 6,7-dichloro-2,3-dimethoxy-5-[1-methyl-4-phenyl-1H-1,2,3-triazol-5-yl]quinoxaline (0.046 g, 9%), was obtained as an orange oil.

$^1$H-NMR (300 MHz, CDCl$_3$): δ=3.84 (3H, s), 4.11 (3H, s), 4.16 (3H, s), 7.20 (3H, m), 7.33 (2H, m), 7.96 (1H, s).

m/z (thermospray) 416 (MH$^+$).

PREPARATION 112

6,7-Dichloro-2,3-dimethoxy-5-[5-phenyl-2-(2-(triphenylmethoxy)ethyl)-2H-1,2,3-triazol-4-yl]quinoxaline (isomer 1), 6,7-dichloro-2,3-dimethoxy-5-[5-phenyl-1-(2-(triphenylmethoxy)ethyl)-1H-1,2,3-triazol-4-yl]quinoxaline (isomer 2) and 6,7-dichloro-2,3-dimethoxy-5-[4-phenyl-1-(2-(triphenylmethoxy)ethyl)-1H-1,2,3-triazol-5-yl]quinoxaline (isomer 3)

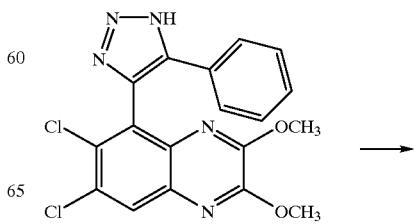

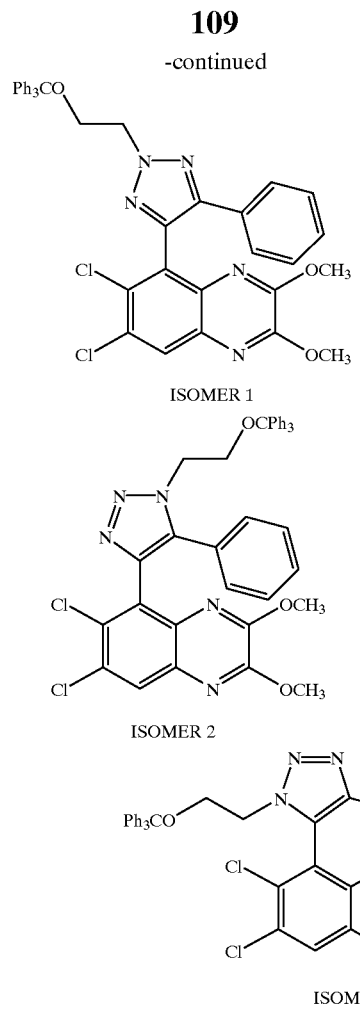

The title compounds were prepared by a similar method to that of Preparation 111 using 2-(triphenylmethoxy)ethyl bromide (Liebigs Ann., 635, 3 (1960)) instead of iodomethane and were purified by flash chromatography on silica gel, by gradient elution using toluene:diethyl ether (1:0 changing to 9:1, by volume) to afford as the first eluted product, isomer 1, tentatively assigned as 6,7-dichloro-2,3-dimethoxy-5-[5-phenyl-2-(2-(triphenylmethoxy)ethyl)-2H-1,2,3-triazol-4-yl]quinoxaline (0.336 g, 45%) as a white solid.

$^1$H-NMR (300 MHz, CDCl$_3$): δ=3.32 (3H, s), 3.73 (2H, m), 4.11 (3H, s), 4.73 (2H, m), 7.22 (12H, m), 7.40 (6H, m), 7.47 (2H, m), 8.02 (1H, s).

m/z (thermospray) 688 (MH$^+$).

The second eluted product, isomer 2, tentatively assigned as 6,7-dichloro-2,3-dimethoxy-5-[5-phenyl-1-(2-triphenylmethoxy)ethyl)-1H-1,2,3-triazol-4-yl]quinoxaline (0.104 g, 14%), was obtained as a white solid.

$^1$H-NMR (300 MHz, CDCl$_3$): δ=3.40 (2H, m), 3.44 (3H, s), 4.17 (3H, s), 4.25 (2H, m), 7.22 (18H, m), 7.39 (2H, m), 8.02 (1H, s).

m/z (thermospray) 688 (MH$^+$).

The third eluted product, isomer 3, tentatively assigned as 6,7-dichloro-2,3-dimethoxy-5-[4-phenyl-1-(2-(triphenylmethoxy)ethyl)-1H-1,2,3-triazol-5-yl]quinoxaline (0.037 g, 5%), was obtained as an off-white solid.

$^1$H-NMR (300 MHz, CDCl$_3$): δ=3.47 (3H, s), 3.73 (2H, m), 4.10 (3H, s), 4.58 (2H, m), 7.24 (20H, m), 7.94 (1H, s).

m/z (thermospray) 688 (MH$^+$).

PREPARATION 113

5-Amino-6-chloro-2,3-dimethoxy-7-methylquinoxaline and 5-amino-7-chloro-2,3-dimethoxy-6-methylquinoxaline

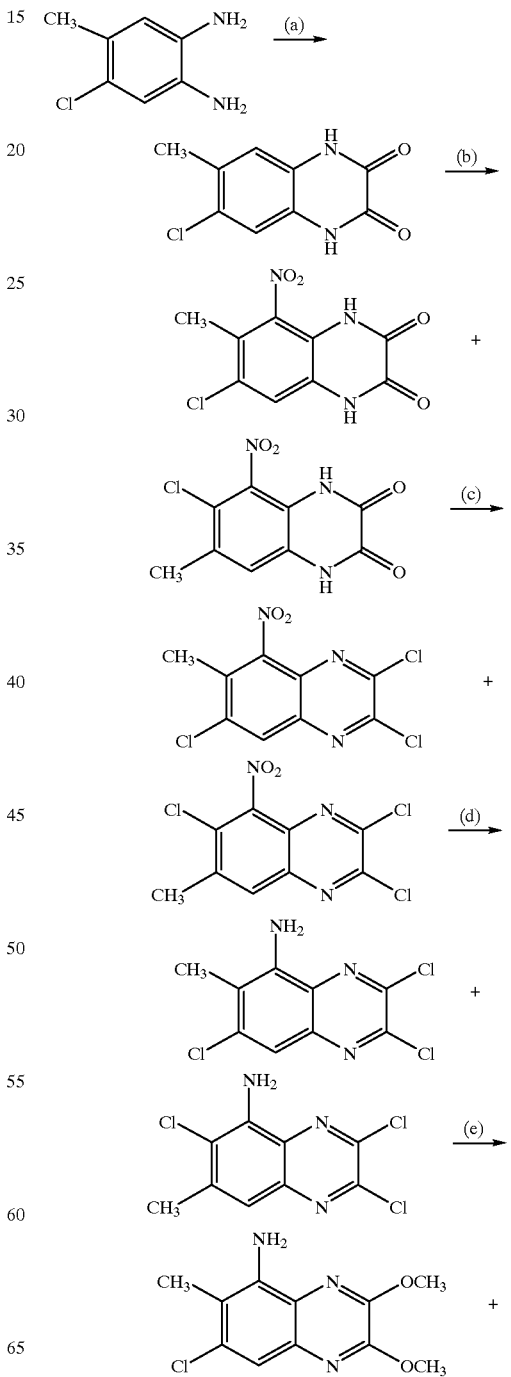

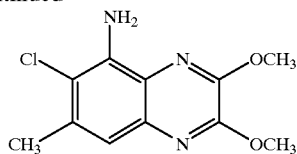

(a) A mixture of 1,2-diamino-4-chloro-5-methylbenzene hydrochloride (1.90 g, 9.84 mmol), oxalic acid (1.24 g, 13.8 mmol) and 4M aqueous hydrochloric acid solution (49 mL) was heated under reflux for 4.5 hours. After being cooled, the solid precipitate was collected by filtration, washed well with water and dried under reduced pressure at 80° C. to afford 6-chloro-7-methyl-2,3(1H, 4H)-quinoxalinedione (1.68 g, 81%) as a dark grey solid, mp >330° C.

Analysis (%): Found: C, 51.58; H, 2.98; N, 13.27. $C_9H_7ClN_2O_2$ requires C, 51.32; H, 3.35; N, 13.30.

(b) 6-Chloro-7-methyl-2,3(1H, 4H)-quinoxalinedione (1.26 g, 5.98 mmol) was added in portions over 3 minutes to vigorously stirred concentrated nitric acid (10 mL, d=1.42) at room temperature. The resulting heterogeneous mixture was then warmed to 40° C. and stirred for 12 hours. After being cooled the yellow mixture was poured into ice-water (100 mL) and stirred for 30 minutes. The resulting yellow precipitate was collected by filtration, washed with water and dried by suction to afford a mixture of 6-chloro-7-methyl-5-nitro-2,3(1H, 4H)-quinoxalinedione and 7-chloro-6-methyl-5-nitro-2,3(1H, 4H)-quinoxalinedione (1:2 molar ratio, 1.35 g, 88%) as a yellow solid.

$^1$H-NMR (300 MHz, CDCl$_3$): δ=2.23 (2H, s), 2.35 (1H, s), 7.19 (0.3H, s), 7.30 (0.7H, s), 11.9–12.25 (2H, br m).

(c) The above mixture of 6-chloro-7-methyl-5-nitro-2,3 (1H, 4H)-quinoxalinedione and 7-chloro-6-methyl-5-nitro-2,3(1H, 4H)-quinoxalinedione (1.35 g, 5.73 mmol), thionyl chloride (12.5 mL, 20.4 g, 0.172 mol) and dimethylformamide (44 μL, 42 mg, 0.573 mmol) was heated under reflux for 4 hours. After being cooled the mixture was cautiously added to vigorously stirred ice-water (300 mL). The resulting precipitate was collected by filtration, washed with water and dried by suction to give a mixture of 2,3,7-trichloro-6-methyl-5-nitroquinoxaline and 2,3,6-trichloro-7-methyl-5-nitroquinoxaline (2:1 molar ratio, 1.45 g, 87%) as a straw-coloured powder. This mixture could be separated with difficulty for characterisation purposes by flash chromatography on silica gel, by gradient elution using hexane:dichloromethane (9:1 changing to 3:1, by volume) to give, as the first eluted isomer, 2,3,7-trichloro-6-methyl-5-nitroquinoxaline as a white solid, mp 164–165° C.

Analysis (%): Found: C, 36.76; H, 1.37; N, 14.43. $C_9H_4Cl_3N_3O_2$ requires: C, 36.96; H, 1.38; N, 14.37.

The second eluted isomer 2,3,6-trichloro-7-methyl-5-nitroquinoxaline, was obtained as a straw-coloured solid, mp 121–122° C.

Analysis (%): Found: C, 39.78; H, 2.02; N, 13.23. $C_9H_4Cl_3N_3O_2$. 0.22 hexane requires: C, 39.80; H, 2.29; N, 13.49.

(d) The above mixture of 2,3,7-trichloro-6-methyl-5-nitroquinoxaline and 2,3,6-trichloro-7-methyl-5-nitroquinoxaline (250 mg, 0.855 mmol) and stannous chloride dihydrate (1.35 g, 5.98 mmol) in ethyl acetate (8.5 mL) was heated under reflux for 3 hours under nitrogen. After being cooled the mixture was diluted with ethyl acetate (50 mL) and washed with 10% aqueous sodium carbonate solution (2×25 mL), brine (25 mL), dried (MgSO$_4$), filtered and concentrated under reduced pressure to afford a mixture of 5-amino-2,3,7-trichloro-6-methylquinoxaline and 5-amino-2,3,6-trichloro-7-methylquinoxaline (2:1 molar ratio, 217 mg, 97%) as an orange solid.

$^1$H-NMR (300 MHz, CDCl$_3$): δ=2.41 (2H, s), 2.55 (1H, s), 5.03 (1.3H, br s), 5.08 (0.7H, br s), 7.23 (0.3H, s), 7.44 (0.7H, s).

m/z (thermospray) 262 (MH$^+$).

(e) A 25% w/w solution of sodium methoxide in methanol (433 μL, 1.89 mmol) was added dropwise to a solution of the above mixture of 5-amino-2,3,7-trichloro-6-methylquinoxaline and 5-amino-2,3,6-trichloro-7-methylquinoxaline (200 mg, 0.788 mmol) in dry tetrahydrofuran (7.9 mL) at 0° C. under nitrogen. The mixture was stirred for 3 hours, diluted with ethyl acetate (30 mL), washed with water (2×10 mL), brine (10 mL), dried (MgSO$_4$), filtered and concentrated under reduced pressure. The solid residue was purified by flash chromatography on silica gel, by gradient elution using hexane:ethyl acetate (95:5 changing to 1:1, by volume) to give as the first eluted isomer, 5-amino-6-chloro-2,3-dimethoxy-7-methylquinoxaline (48 mg, 25%) as an off-white solid, mp 169–170° C.

Analysis (%): Found: C, 53.80; H, 5.16; N, 16.18. $C_{11}H_{12}ClN_3O_2$. 0.15 hexane requires: C, 53.61; H, 5.33; N, 15.76.

The second eluted isomer, 5-amino-7-chloro-2,3-dimethoxy-6-methylquinoxaline (85 mg, 44%), was obtained as an orange solid, mp 181–182° C.

Analysis (%): Found: C, 52.55; H, 4.72; N, 16.61. $C_{11}H_{12}ClN_3O_2$. 0.05 hexane requires: C, 52.61; H, 4.96; N, 16.29.

PREPARATION 114

6-Chloro-2,3-dimethoxy-7-methyl-5-[5-methoxymethyl-3-(3-pyridyl)-4H-1,2,4-triazol-4-yl]quinoxaline

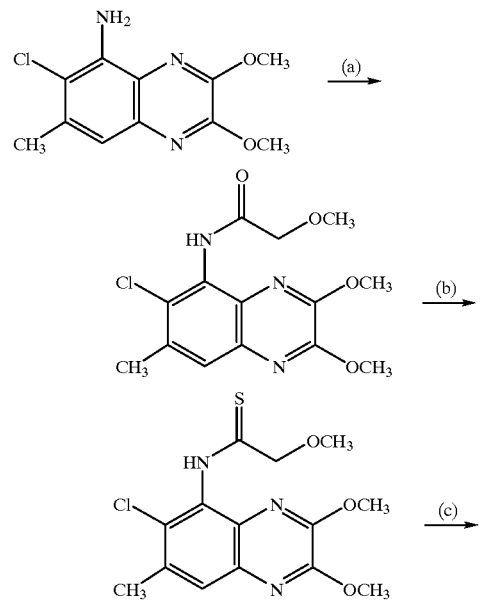

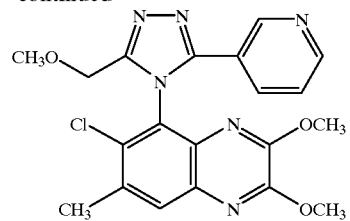

(a) Methoxyacetylchloride (2.16 mL, 2.57 g, 23.66 mmol) was added to a solution of 5-amino-6-chloro-2,3-dimethoxy-7-methylquinoxaline (Preparation 113, 5 g, 19.72 mmol) and pyridine (1.91 mL, 1.89 g, 23.66 mmol) in dichloromethane (80 mL) at 0° C. After a further 1 hour at this temperature, the mixture was washed with 2M aqueous hydrochloric acid solution, brine, dried (MgSO$_4$) and concentrated under reduced pressure. The residue was triturated with diisopropyl ether and filtered to give 6-chloro-2,3-dimethoxy-5-methoxyacetamido-7-methylquinoxaline (6.06 g, 98%) as an off white solid, mp 170–171° C.

$^1$H-NMR (300 MHz, CDCl$_3$): δ=2.55 (3H, s), 3.6 (3H, s), 4.1 (3H, s), 4.13 (3H, s), 4.18 (2H, s) 7.61 (1H, s), 8.47 (1H, br s).

m/z (thermospray) 326 (MH$^+$).

(b) 2,4-bis(4-Methoxyphenyl)-1,3-dithia-2,4-diphosphetane-2,4-disulphide (Lawesson's reagent) (4.47 g, 11.06 mmol) was added to 6-chloro-2,3-dimethoxy-5-methoxyacetamido-7-methylquinoxaline (6 g, 18.43 mmol) in tetrahydrofuran (120 mL) and the mixture stirred for 18 hours, then evaporated under reduced pressure. The residue was purified by flash chromatography on silica gel, by gradient elution using hexane:dichloromethane (1:1 changing to 1:4 changing to 0:1, by volume) to give 6-chloro-2,3-dimethoxy-5-methoxythioacetamido-7-methylquinoxaline (5.48 g, 87%) as a yellow foam, mp 174–176° C.

$^1$H-NMR (300 MHz, CDCl$_3$): δ=2.55 (3H, s), 3.65 (3H, s), 4.05 (3H, s), 4.15 (3H, s), 4.55 (2H, s), 7.7 (1H, s), 9.65 (1H, br s).

m/z (thermospray) 342 (MH$^+$).

(c) A mixture of 6-chloro-2,3-dimethoxy-5-methoxythioacetamido-7-methylquinoxaline (1.45 g, 4.25 mmol), nicotinic acid hydrazide (1.16 g, 8.5 mmol), mercury (II) oxide (1.84 g, 8.5 mmol), powdered 4 Å molecular sieves (1.06 g) and n-butanol (60 mL) was heated under reflux for 8 hours. After being cooled, the mixture was filtered through ARBOCEL (trade mark) filter aid and the residue washed with dichloromethane. The filtrate was concentrated under reduced pressure to afford a light brown solid which was partitioned between ethyl acetate and 2M aqueous hydrochloric acid solution. The aqueous layer was extracted with dichloromethane (4×50 mL), the combined dichloromethane extracts dried (MgSO$_4$) and concentrated under reduced pressure. The residue was crystallised from diisopropyl ether/methanol to give a solid (394 mg). The mother liquors from the crystallisation were evaporated under reduced pressure and the residue purified by flash chromatography on silica gel, eluting with ethyl acetate to give, after trituration with diisopropyl ether, a further amount of solid (364 mg). The two solids were combined together to give the title compound (740 mg, 41%) as a pale yellow solid, mp 183–184° C.

$^1$H-NMR (300 MHz, CDCl$_3$): δ=2.5 (3H, s), 3.18 (3H, s), 3.8 (3H, s), 4.16 (3H, s), 4.45 (2H, m), 7.58 (1H, m), 7.86 (1H, s), 8.35 (1H, m), 8.45 (1H, m), 8.65 (1H, m).

m/z (thermospray) 427 (MH$^+$).

PREPARATION 115

7-Chloro-2,3-dimethoxy-6-methyl-5-[5-methoxymethyl-3-(3-pyridyl)-4H-1,2,4-triazol-4-yl]quinoxaline

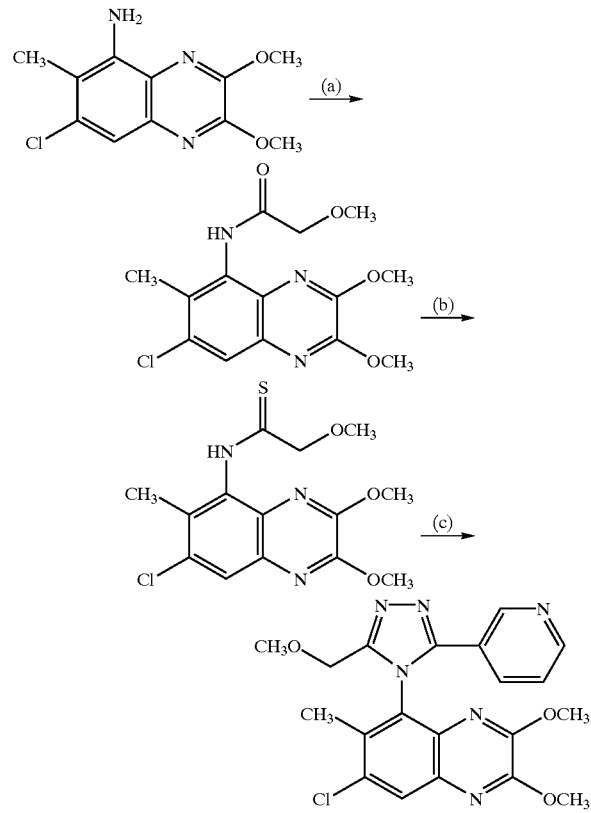

The title compound was prepared by a similar method to that of Preparation 114 using 5-amino-7-chloro-2,3-dimethoxy-6-methylquinoxaline (Preparation 113) in place of 5-amino-6-chloro-2,3-dimethoxy-7-methylquinoxaline. It was obtained as an off-white solid, mp 166–168° C.

$^1$H-NMR (300 MHz, CDCl$_3$): δ=2.25 (3H, s), 3.2 (3H, s), 3.78 (3H, s), 4.15 (3H, s), 4.35 (2H, m), 7.2 (1H, m), 7.82 (1H, m), 8.0 (1H, s) 8.45 (1H, m), 8.55 (1H, m).

m/z (thermospray) 427 (MH$^+$).

PREPARATION 116

2-Methoxycarbonylpyridine-5-carboxylic acid hydrazide

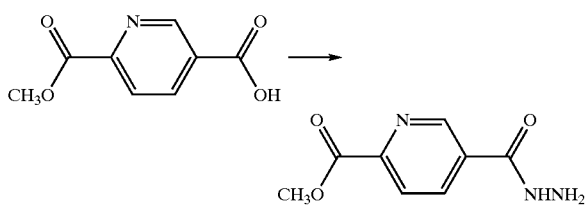

A mixture of 2-methoxycarbonylpyridine-5-carboxylic acid (Chem. Abstr., 68, 68840 h (1968)) (0.40 g, 2.2 mmol)

and N-ethoxycarbonyl-2-ethoxy-1,2-dihydroquinoline (0.60 g, 2.4 mmol) in dichloromethane (10 mL) was stirred at room temperature under nitrogen for 0.75 hour. Hydrazine hydrate (0.110 mL, 2.2 mmol) was then added and after a further 5 minutes the precipitate formed was collected by filtration, washed with dichloromethane and dried to give the title compound (0.349 g, 81%) as white solid, mp 177–180° C.

$^1$H-NMR (300 MHz, DMSO-d$_6$): δ=4.90 (3H, s), 5.00 (2H, br s), 8.10 (1H, d, J=10 Hz), 8.27 (1H, dd, J=2 and 10 Hz), 9.05 (1H, d, J=2 Hz), 10.05 (1H, br s).

m/z (thermospray) 196 (MH$^+$).

PREPARATION 117

Pyrimidine-2-carboxylic acid hydrazide

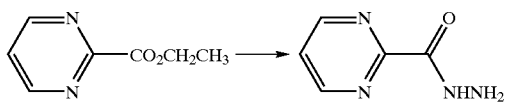

A mixture of pyrimidine-2-carboxylic acid ethyl ester (Ann. Chim., 5, 351 (1960)) (0.866 g, 5.7 mmol) and hydrazine hydrate (0.332 mL, 6.8 mmol) in ethanol (20 mL) was heated under reflux for 3 hours, then concentrated under reduced pressure. The residue was triturated with diethyl ether, collected by filtration and washed with ethyl acetate to give the title compound (0.542 g, 69%) as a yellow solid, mp 173–175° C.

$^1$H NMR (300 MHz, DMSO-d$_6$): δ=4.20 (2H, br s), 7.50 (1H, t, J=4 Hz), 8.83 (2H, d, J=4 Hz), 9.93 (1H, br s).

m/z (thermospray) 139 (MH$^+$).

PREPARATIONS 118–132

The following tabulated compounds were prepared by a similar method to that of Preparation 117 using hydrazine hydrate and the appropriate ethyl ester (R$^B$CO$_2$C$_2$H$_5$).

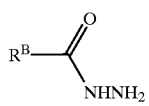

| Prep. No. | R$^B$ | mp (° C.) | $^1$H-NMR (300 MHz, DMSO-d$_6$) or m/z or microanalysis | Reference for the ethyl ester |
|---|---|---|---|---|
| 118 | (2-methyl-pyridin-3-yl) | 98–100 | δ = 2.45(3H, obscured), 4.46(2H, br s), 7.22 (1H, s), 7.62(1H, d, J=8Hz), 8.46(1H, m), 9.44 (1H, s). (thermospray) 151.7 (MH$^+$). | — |
| 119 | (4-methyl-1H-imidazol-5-yl) | 209–212 | δ = 2.39(3H, s), 4.20(2H, br s), 7.44(1H, s), 8.56(1H, s). (thermospray) 140.6 (MH$^+$). | — |
| 120 | (pyridin-3-yl-methyl) | — | δ = 3.39(2H, s), 4.20(2H, br s), 7.30(1H, m), 7.64(1H, d, J=8Hz), 8.41(1H, m), 9.18 (1H, br s). (thermospray) 152.0 (MH$^+$). | — |
| 121 | (1-methyl-1H-pyrazol-5-yl) | 154–155 | δ = 4.02(3H, s), 4.22(2H, br s), 6.78(1H, m), 7.40(1H, s), 9.62(1H, br s). (thermospray) 141 (MH$^+$). | J. Org. Chem., 33, 4451 (1968). |
| 122 | (5-amino-1,3,4-oxadiazol-2-yl) | 265–266 | δ = 4.58(2H, br s), 7.51(2H, s), 10.07(1H, br s). (thermospray) 160 (MNH$_4^+$). | Ric. Sci., 36(5), 332 (1966). |
| 123 | (3-ethyl-1H-pyrazol-5-yl) | 121–123 | δ = 0.90(3H, t, J=7Hz), 1.59(2H, m), 2.54(2H, q, J=7Hz), 4.27(2H, br s), 6.38(1H, s), 9.10 (1H, s). (thermospray) 168.7 (MH$^+$). | Chem. Pharm. Bull., 32(4), 1568 (1984). |

-continued

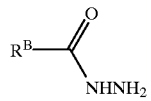

| Prep. No. | R$^B$ | mp (° C.) | $^1$H-NMR (300 MHz, DMSO-d$_6$) or m/z or microanalysis | Reference for the ethyl ester |
|---|---|---|---|---|
| 124 | 1-methyl-pyrazol-4-yl (CH$_3$ on N) | 188–191 | δ = 3.83(3H, s), 4.27(2H, br s), 7.79(1H, s), 8.05(1H, s), 9.20(1H, br s) (thermospray) 141.1 (MH$^+$) | J. Het. Chem., 30, 865 (1993). |
| 125 | 1-methyl-imidazol-2-yl (CH$_3$ on N) | 111–113 | δ = 3.96(2H, br s), 4.03(3H, s), 6.94(1H, s), 7.01(1H, s), 8.60(1H, br s). (thermospray) 141 (MH$^+$). | J. Org. Chem., 52, 3496 (1987). |
| 126 | 1H-1,2,3-triazol-4-yl | 266–268 | δ = 4.24(2H, br s), 8.07(1H, s), 8.04 (1H, br s). (thermospray) 128 (MH$^+$). | J. Chem. Soc., Perk. Trans. 1, 627 (1982). |
| 127 | 1H-pyrazol-4-yl | 178–180 | δ = 4.34(2H, br s), 6.68(1H, s), 7.69(1H, s), 9.25(1H, br s), 13.01(1H, br s). (thermospray) 127 (MH$^+$). | — |
| 128 | 1-methyl-1,2,4-triazol-5-yl (CH$_3$ on N) | 170–172 | δ = 4.10(3H, s), 4.56(2H, br s), 7.97(1H, s), 9.92(1H, br s). (thermospray) 127 (MH$^+$). | Chem. Zeit., 110, 101 (1986). |
| 129 | 5-phenyl-pyridin-3-yl | — | δ = 4.58(2H, br.s), 7.40–7.58(3H, m), 7.79 (2H, d, J=8Hz), 8.40(1H, s), 8.92(1H, s), 8.99(1H, s), 10.01(1H, br.s) | Eur. J. Med. Chem., 22, 383 (1987) |
| 130 | 1H-1,2,4-triazol-3-yl | 290–292 | δ = 4.48(2H, broad s), 8.39(1H, s), 9.63(1H, broad s) (thermospray) 145 (MNH$_4^+$) | — |
| 131 | 6-phenyl-pyridin-3-yl | 196–197 | Found: C, 67.34; H, 5.18; N, 19.62. C$_{12}$H$_{11}$N$_3$O requires: C, 67.59; H, 5.20; N, 19.71% | Preparation 133 |
| 132 | 1-phenyl-imidazol-4-yl | 188–189 | Found: C, 58.86; H, 4.98; N, 27.09. C$_{10}$H$_{10}$N$_4$O. 0.1 H$_2$O requires: C, 58.87; H, 5.04; N, 27.46% | Preparation 134 |

PREPARATION 133

2-Phenylpyridine-5-carboxylic acid ethyl ester

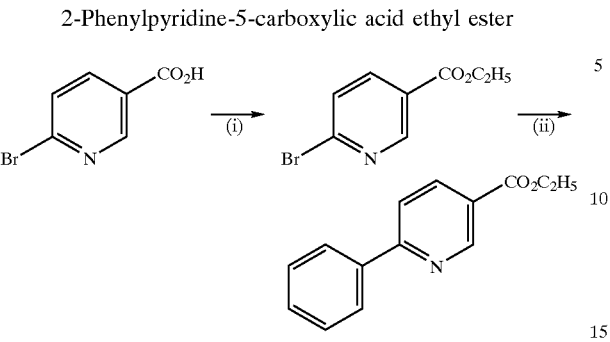

(i) 2-Bromopyridine-5-carboxylic acid ethyl ester

A mixture of 2-bromopyridine-5-carboxylic acid (J.Org.Chem., 12, 456 (1947)) (2.32 g, 11.49 mmol) and N-ethoxycarbonyl-2-ethoxy-1,2-dihydroquinoline (3.12 g, 12.64 mmol) in dichloromethane (30 ml) was stired at room temperature for 1 hour under nitrogen. Absolute ethanol (5 ml) was added and the mixture stirred for 30 minutes and then concentrated under reduced pressure. The residue was partitioned between dichloromethane (40 ml) and 10% w/w aqueous potassium carbonate solution (40 ml). The aqueous layer was extracted with dichloromethane (25 ml) and the combined organic layers were dried ($MgSO_4$) and concentrated under reduced pressure. Purification by flash chromatography on silica gel, eluting with dichloromethane gave 2-bromopyridine-5-carboxylic acid ethyl ester (2.18 g, 83%) as a colourless oil.

Analysis (%): Found: C,41.57; H,3.45; N,5.98. $C_8H_8NO_2Br$ required: C, 41.77; H,3.50; N,6.09.

(ii) 2-Phenylpyridine-5-carboxylic acid ethyl ester

A mixture of 2-bromopyridine-5-carboxylic acid ethyl ester (see part (i)) (1.855 g, 8.065 mmol), phenyltrimethyl tin (3.89 g, 16.13 mmol), bis(triphenylphosphine)palladium (II) chloride (371 mg) and lithium chloride (1.03 g. 24. 195 mmol) in dry dimethylformamide (40 ml) was heated at 100° C. for 1.5 hours under nitrogen. After cooling the mixture was concentrated under reduced pressure and the residue purified by flash chromatography on silica gel eluting with hexane:ethyl acetate (10:1, by volume) to give the title compound (0.843 g, 46%) as a white solid.

$^1$H-NMR (300 MHz, $CDCl_3$): δ=1.43 (3H,t, J=8 Hz), 4.42 (2H,q, J=8 Hz), 7.49 (3H,m), 7.80 (1H,m), 8.07 (2H,m), 8.36 (1H,m), 9.29 (1H,m).

m/z (thermospray) 228 ($MH^+$).

PREPARARTION 134

1-Phenylimidazole-4-carboxylic acid ethyl ester

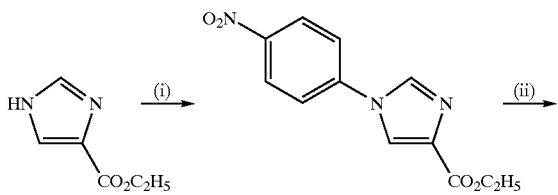

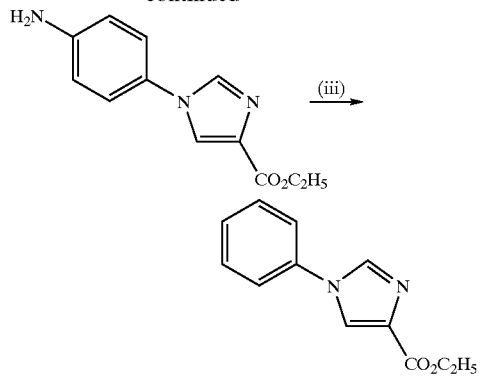

(i) 1-(4-Nitrophenyl)imidazole-4-carboxylic acid ethyl ester

A mixture of 1H-imidazole-4-carboxylic acid ethyl ester (J.Het.Chem., 19, 253 (1982)) (584 mg, 4.17 mmol), 4-fluoronitrobenzene (588 mg, 4.17 mmol) and anhydrous sodium carbonate (487 mg, 4.59 mmol) in dry dimethylformamide (10 ml) was heated at 50° C. for 24 hours under nitrogen. After cooling to room temperature the mixture was poured into ice-cold water (60 ml) and the resulting solid collection by filtration, washed with water and dried under reduced pressure at 60° C. to give 1-(4-nitrophenyl) imidazole-4-carboxylic acid ethyl ester (980 mg, 90%) as an off-white solid, m.p. 198–200° C.

Analysis (%): Found: C,55.06; H,4.21; N,15.99. $C_{12}H_{11}N_3O_4$ requires: C,55.17; H,4.24; N,16.08.

(ii) 1-(4-Aminophenyl)imidazole-4-carboxylic acid ethyl ester

A mixture of 1-(4-nitrophenyl)imidazole-4-carboxylic acid ethyl ester (see part (i)) (950 mg, 3.64 mmol) and tin (II) chloride (4.11 g, 18.2 mmol) in absolute ethanol (30 ml) was heated under reflux for 30 minutes under nitrogen. After cooling to room temperature the mixture was concentrated under reduced pressure and then partitioned between ethyl acetate (30 ml) and saturated sodium hydrogen carbonate solution (20 ml). The aqueous layer was extracted with ethyl acetate (30 ml) and the combined organic layers were dried ($MgSO_4$) and concentrated under reduced pressure to give 1-(4-aminophenyl)imidazole-4-carboxylic acid ethyl ester (810 mg, 96%) as a yellow oil.

$^1$H-NMR (300 MHz, $CDCl_3$): δ=1.40 (3H,t,J=7 Hz), 2.86 (2H,broad s), 4.39 (2H,q, J=7 Hz), 6.76 (2H,d, J=9 Hz), 7.18 (2H,d, J=9 Hz), 7.72 (1H,s), 7.83 (1H,s).

m/z (thermospray) 232 ($MH^+$).

(iii) 1-Phenylimidazole-4-carboxylic acid ethyl ester

Tert-butyl nitrite (535 mg, 5.19 mmol) in dry dimethylformamide (15 ml) was heated to 65° C. under nitrogen and then 1-(4-aminophenyl)imidazole-4-carboxylic acid ethyl ester (see part (ii)) (800 mg, 3.463 mmol) in dry dimethylformamide (5 ml) was added over 10 minutes. The mixture was heated at 65° C. for a further 20 minutes and then cooled to room temperature. The mixture was poured into saturated brine (50 ml) and extracted with dichloromethane (3×20 ml). The combined organic layers were dried ($MgSO_4$) and concentrated under reduced pressure. Purification by flash chromatography on silica gel eluting with dichloromethane gave the title compound (520 mg, 70%) as an off-white solid.

$^1$H-NMR (400 MHz, $CDCl_3$): δ=1.43 (3H,t, J=7 Hz), 4.42 (2H,q, J=7 Hz), 7.45 (3H,m), 7.54 (2H,m), 7.88 (1H,s), 7.98 (1H,s).

m/z (thermospray) 217 ($MH^+$).

PREPARATIONS 135 to 149

The following tabulated compound were prepared by a similar method to that of Preparation 27 using 5-amino-6,7-dichloro-2,3-dimethoxyquinoxaline and the appropriate acid chloride ($R^A$COCl) and hydrazide ($R^B$CONHNH$_2$).

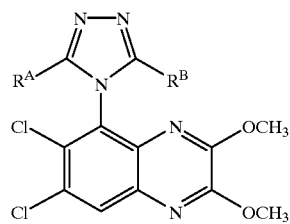
| Prep. No. | R^A from acid chloride | R^B from hydrazide | mp (° C.) |
|---|---|---|---|
| 135 | phenyl-OCH$_2$— | 3-pyridyl | — |
| 136 | phenyl-CH$_2$OCH$_2$— | 3-pyridyl | — |
| 137 | —CH$_2$OCH$_3$ | 5-phenyl-3-pyridyl | — |
| 138 | —CH$_2$OCH$_2$-cyclohexyl | 3-pyridyl | — |
| 139 | —CH$_2$OCH$_2$-cyclopentyl | 3-pyridyl | — |
| 140 | —CH$_2$OCH$_2$CF$_3$ | 3-pyridyl | — |
| 141 | CH$_3$ | 1H-1,2,4-triazol-3-yl | 224–226 |
| 142 | phenyl-CH$_2$CH$_2$— | 3-pyridyl | — |
| 143 | phenyl-CH$_2$— | 3-pyridyl | — |
| 144 | CH$_3$CH$_2$OCH$_2$— | 3-pyridyl | — |

-continued

| | | | |
|---|---|---|---|
| 145 | CH₃O⤴ | (quinoline-3-yl) | 210–212 |
| 146 | C₂H₅OCH₂CH₂— | (pyridin-3-yl) | — |
| 147 | CH₃OCH₂— | (quinolin-6-yl) | 212–214 |
| 148 | CH₃OCH₂— | (1-phenyl-1H-imidazol-4-yl) | 219–220 |
| 149 | CH₃OCH₂— | (6-phenylpyridin-3-yl) | 195–197 |

| Prep. No. | ¹H-NMR (300 MHz, CDCl₃) or m/z or Analysis (%) | Work-up and chromatography eluent variations for step (c) | Reference for hydrazide |
|---|---|---|---|
| 135 | δ = 3.50(3H, s), 4.10(3H, s), 5.18 (1H, d, J=14Hz), 5.28(1H, d, J=14Hz), 6.50(2H, d, J=10Hz), 6.82(1H, t, J=8Hz), 7.04(2H, t, J=8Hz), 7.20(1H, m), 7.84(1H, m), 8.04(1H, s), 8.52(2H, br.s). m/z (thermospray) 509 (MH⁺) | No acid wash | — |
| 136 | δ = 3.74(3H, s), 4.08(3H, s), 4.32 (2H, m), 4.60(2H, m), 6.82(2H, m), 7.18(3H, m), 7.20(1H, m), 7.86 (1H, m), 8.00(1H, s), 8.50(2H, m). m/z (thermospray) 523 (MH⁺). | No acid wash | — |
| 137 | δ = 3.20(3H, s), 3.82(3H, s), 4.16(3H, s), 4.48(2H, q, J=14Hz), 7.38–7.49(5H, m), 8.08(1H, s), 8.17(1H, t, J=3Hz), 8.37(1H, s), 8.77 (1H, s). m/z (thermospray) 523 (MH⁺) | — | Preparation 129 |
| 138 | δ = 0.40–0.65(2H, m), 0.91–1.16(3H, m), 1.18–1.31 (2H, m), 1.43–1.76(4H, m), 2.95–3.08(2H, m), 3.83 (3H, s), 4.15(3H, s), 4.51 (2H, q, J=15Hz), 7.89(1H, d, J=8Hz), 8.05(1H, s), 8.50 (1H, s), 8.55(1H, d, J=3Hz). m/z (thermospray) 529 (MH⁺). | — | — |
| 139 | (NMR. 400 MHz): δ = 0.74–0.91(2H, m), 1.30–1.47 (4H, m), 1.60–1.78(2H, m), 3.08–3.20(2H, m), 3.83(3H, s), 4.16 (3H, s), 4.48–4.62(2H, doublet of doublets, J=13Hz, 28Hz), 7.26(1H, obs), 7.90(1H, d, J=8Hz), 8.08(1H, s), 8.50 | elution with dichloromethane: methanol (99:1, by volume) | — |

-continued

| | | | |
|---|---|---|---|
| | (1H, s), 8.57(1H, s).<br>m/z (thermospray) 515 (MH⁺) | | |
| 140 | δ = 1.58(2H, s), 3.73(2H, q, J=8Hz), 3.82(3H, s), 4.16 (3H, s), 4.66(2H, AB doublet, J=7Hz, 12Hz), 7.26(1H, obs), 7.87(1H, d, J=8Hz), 8.05(1H, s), 8.48(1H, s), 8.56(1H, d, J=4Hz).<br>m/z (thermospray) 515 (MH⁺). | — | — |
| 141 | Found: C, 43.47, H, 3.35; N, 26.61.<br>$C_{15}H_{12}N_8O_2Cl$. 0.5 $H_2O$) requires:<br>C, 43.29; H, 3.15; N, 26.92. | No acid wash; elution with ethyl acetate:methanol (98:2, by volume) | Preparation 130 |
| 142 | (NMR. 400 MHz):<br>δ = 2.59–2.67(1H, m), 2.82–2.91 (1H, m), 3.00–3.06(2H, m), 3.72 (3H, s), 4.11(3H, s), 6.93–6.98 (2H, m), 7.02–7.11(3H, m), 7.17–7.20(1H, m), 7.79–7.83(1H, m), 8.03(1H, s), 8.39–8.42(1H, m), 8.44–8.48(1H, m).<br>m/z (thermospray) 507 (MH⁺) | Elution with ethyl acetate: methanol (98:2, by volume). | |
| 143 | δ = 3.66(3H, s), 3.77(1H, d, J=15Hz), 4.10(3H, s), 4.28(1H, d, J=15Hz), 6.64–6.68(2H, m), 6.81–6.93(3H, m), 7.18–7.24(1H, m), 7.83–7.89(1H, m), 7.99(1H, s), 8.47–8.52(1H, m).<br>m/z (thermospray) 493 (MH⁺) | Elution with ethyl acetate: methanol (98:2, by volume) | |
| 144 | δ = 0.83(3H, t, J=8Hz), 3.30 (2H, m), 3.80(3H, s), 4.13(3H, s), 4.44(1H, d, J=12Hz), 4.57(1H, d, J=12Hz), 7.58(1H, m), 8.08(1H, s), 8.18(1H, m), 8.53(1H, m), 8.69 (1H, m).<br>m/z (thermospray) 461 (MH⁺). | Elution with ethyl acetate | |
| 145 | δ = 3.19(3H, s), 3.85(3H, s), 4.12 (3H, s), 4.47(1H, d, J=11Hz), 4.56 (1H, d, J=11Hz), 7.56(1H, m), 7.71 (2H, m), 8.00(1H, m), 8.07(1H, s), 8.32(1H, m), 8.78(1H, m).<br>m/z (thermospray) 497 (MH⁺). | Elution with ethyl acetate | J. Chem. Soc., 1943, 413 |
| 146 | δ = 1.05(3H, t, J=9Hz), 2.78 (2H, m), 3.41(2H, m), 3.79(2H, m), 3.87(3H, s), 4.17(3H, s), 7.28 (1H, m), 7.92(1H, m), 8.10(1H, s), 8.44(1H, m), 8.54(1H, m).<br>m/z (thermospray) 475 (MH⁺) | Elution with ethyl acetate: methanol (99:1, by volume) | |
| 147 | Found: C, 54.65; H, 3.81; N, 16.05.<br>$C_{23}H_{18}N_6O_3Cl_2.0.2CH_3CO_2C_2H_5$.<br>0.4 $H_2O$ requires: C, 54.75; H, 3.94; N, 16.09. | Elution with ethyl acetate | J. Chem. Soc., 1943, 413 |
| 148 | Found: C, 53.57; H, 3.70; N, 18.89.<br>$C_{23}H_{19}N_7O_3Cl_2$. 0.25 $H_2O$ requires: C, 53.45; H, 3.80; N, 18.97 | Elution with ethyl acetate | Preparation 132 |
| 149 | δ = 3.19(3H, s), 3.86(3H, s), 4.14 (3H, s), 4.44(1H, d, J=11Hz), 4.53 (1H, d, J=11Hz), 7.42(3H, m), 7.70 (1H, m), 7.91(2H, m), 8.01(1H, m), 8.08(1H, s), 8.47(1H, m).<br>m/z (thermospray) 523 (MH⁺). | Elution with ethyl acetate | Preparation 131 |

PREPARATION 150

5-Amino-6,7-dichloro-2,3-dimethoxyquinoxaline

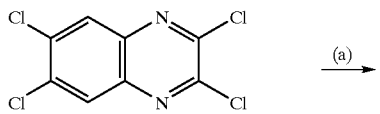

(a) →

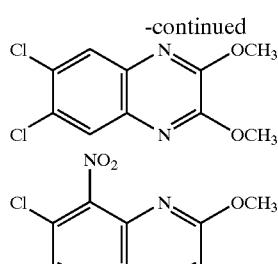

-continued (b) →

(c) →

-continued

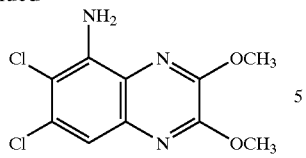

(a) A 25% w/w solution of sodium methoxide in methanol (700 ml, 5.15 mmol) was added to a suspension of 2,3,6,7-tetrachloroquinoxaline (175 g, 0.653 mol) in methanol (1.4 L) at the reflux temperature and the mixture was maintained at the reflux temperature for 4 hours. The mixture was cooled and water (2.1 L) added. The slurry was filtered, the solid was washed with water (0.35 L) and isopropanol (0.175 L) to give 6,7-dichloro-2,3-dimethoxyquinoxaline (159 g, 94%) as a beige solid, m.p. 146–148° C.

$^1$H-NMR (300 MHz, CDCl$_3$); δ=4.13 (6H, s), 7.83 (2H, s).

(b) 6,7-Dichloro-2,3-dimethoxyquinoxaline (25 g, 0.096 mol) was added, portionwise, to fuming nitric acid (0.113 L) which had been pre-cooled to −5° C. The solution was allowed to warm to 10° C. and stirring continued for 2 hours. The solution was then poured into an ice/water mixture (0.5 L). The slurry was filtered and the solid was washed with water and isopropanol (0.05 L) to give 6,7-dichloro-2,3-dimethoxy-5-nitroquinoxaline(27 g, 92%) as a beige solid. m.p. 184–186° C.

$^1$H NMR (300 MHz, CDCl$_3$): δ=4.12 (3H, s), 4.17 (3H, s), 7.98 (1H, s).

(c) 6,7-Dichloro-2,3-dimethoxy-5-nitroquinoxaline (20 g, 0.066 mol) and 5% w/w palladium-on-carbon (50% wet) (1.2 g) were suspended in a mixture of tetrahydrofuran (0.12 L) and ethyl acetate (0.12 L). The mixture was hydrogenated at 60° C. and 414 kPa (60 psi) for 22 hours, cooled, diluted with dichloromethane (0.48 L) and the catalyst removed by filtration through celite (trade mark) filter aid. The solution was concentrated under reduced pressure with the gradual addition of toluene. The mixture was then filtered and the solid was washed with toluene (20 ml) to give the title compound as a brown solid (14.2 g, 78%), m.p. 182–4° C.

$^1$H NMR (300 MHz, CDCl$_3$): δ=4.13 (3H, s), 4.14 (3H, s), 5.07 (2H, br s), 7.26 (1H, s).

PHARMACOLOGICAL DATA

The binding affinities of a selection of the compounds of the Examples for the glycine site of the NMDA receptor were measured using the [$^3$H]-L-689,560 method described on page 20 of the description. The results obtained are tabulated below.

| Example No. | IC$_{50}$ (nM) |
|---|---|
| 5 | 3 |
| 20 | 19 |
| 73 | 4 |

What is claimed is:

1. A compound of the formula:

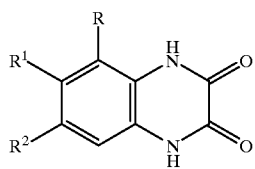

or a pharmaceutically acceptable salt thereof,
wherein

R is a 1,2,3-triazol-4-yl, 1,2,4-triazol-3-yl, 1,2,4-triazol-4-yl or tetrazol-5-yl said R being optionally substituted by 1 or 2 substituents each independently selected from C$_1$–C$_4$ alkyl, C$_2$–C$_4$ alkenyl, C$_3$–C$_7$ cycloalkyl, halo, hydroxy, C$_1$–C$_4$ alkoxy, C$_3$–C$_7$ cycloalkyloxy, —COOH, C$_1$–C$_4$alkoxycarbonyl, —CONR$^3$R$^4$, —NR$^3$R$^4$, —S(O)$_p$(C$_1$–C$_4$ alkyl), —SO$_2$NR$^3$R$^4$, aryl, aryloxy, aryl(C$_1$–C$_4$)alkoxy quinolinyl and het, said C$_1$–C$_4$alkyl being optionally substituted by C$_3$–C$_7$ cycloalkyl, halo, hydroxy, C$_1$–C$_4$ alkoxy, halo(C$_1$–C$_4$) alkoxy, C$_3$–C$_7$ cycloalkyloxy, C$_3$–C$_7$ cycloalkyl (C$_1$–C$_4$)alkoxy, —COOH, C$_1$–C$_4$ alkoxycarbonyl, —CONR$^3$R$^4$, —NR$^3$R$^4$, —S(O)$_p$(C$_1$–C$_4$ alkyl), —SO$_2$ (aryl), —SO$_2$NR$^3$R$^4$, morpholino, aryl, aryloxy, aryl (C$_1$–C$_4$)alkoxy or het, and said C$_2$–C$_4$ alkenyl being optionally substituted by aryl;

R$^1$ and R$^2$ are each independently selected from H, fluoro, chloro, bromo, C$_1$–C$_4$ alkyl and halo(C$_1$–C$_4$)alkyl;

R$^3$ and R$^4$ are either each independently selected from H and C$_1$–C$_4$ alkyl or, when taken together, are C$_5$–C$_7$ alkylene;

p is 0, 1 or 2;

"aryl", used in the definition or aryl, aryloxy, aryl(C$_1$–C$_4$) alkoxy moieties in R and in the definition or aryl and arylalkyl moieties in "het", means phenyl or naphthyl, each optionally substituted by 1 or 2 substituents each independently selected from C$_1$–C$_4$ alkyl, C$_1$–C$_4$ alkoxy, hydroxy, halo, halo(C$_1$–C$_4$)alkyl and —NR$^3$R$^4$;

"het", used in the definition or R, means furyl, thienyl, pyrrolyl, pyrazolyl, imidazolyl, triazolyl, tetrazolyl, oxazolyl, isoxazolyl, triazolyl, isothiazolyl, oxadiazolyl, thiadiazolyl, pyridinyl, pyridazinyl, pyrimidinyl or pyrazinyl, each being optionally substituted by 1 or 2 substituents each independently selected from C$_1$–C$_4$ alkyl, C$_3$–C$_7$ cycloalkyl, C$_1$–C$_4$ alkoxy, halo, hydroxy, —COOH, C$_1$–C$_4$ alkoxycarbonyl, allyloxycarbonyl, —CONR$^3$R$^4$, —NR$^3$R$^4$ —S(O)$_p$ (C$_1$–C$_4$alkyl), —SO$_2$—NR$^3$R$^4$, halo (C$_1$–C$_4$)alkyl, hydroxy(C$_1$–C$_4$)alkyl, C$_1$–C$_4$ alkoxy(C$_1$–C$_4$)alkyl, R$^3$R$^4$NCO(C$_1$–C$_4$)alkyl, aryl, arylalkyl, and/or by an oxido substituent on a ring nitrogen heteroatom when "het" a pyridinyl, pyridazinyl, pyrimidinyl or pyrazinyl group.

2. A compound as claimed in claim 1 wherein R is triazolyl or tetrazolyl, each substituted by 1 or 2 substituents each independently selected from C$_1$–C$_4$ alkyl, C$_2$–C$_4$ alkenyl, C$_3$–C$_7$ cycloalkyl, halo, hydroxy, C$_1$–C$_4$ alkoxycarbonyl, aryl and het, said C$_1$–C$_4$ alkyl being optionally substituted by halo, hydroxy, C$_1$–C$_4$ alkoxy, halo (C$_1$–C$_4$)alkoxy, C$_3$–C$_7$ cycloalkyl(C$_1$–C$_4$)alkoxy, —COOH, C$_1$–C$_4$ alkoxycarbonyl, —NR$^3$R$^4$, —SO$_2$(aryl), morpholino, aryl, aryloxy, aryl(C$_1$–C$_4$)alkoxy or het; or is pyridinyl or pyrimidinyl.

3. A compound as claimed in claim 1 wherein R is 1,2,3-triazol-4-yl, 1,2,4-triazol-3-yl, 1,2,4-triazol-4-yl or tetrazol-5-yl, each substituted by 1 or 2 substituents each independently selected from $C_1$–$C_4$ alkyl, $C_2$–$C_4$ alkenyl, $C_3$–$C_7$ cycloalkyl, halo, hydroxy, $C_1$–$C_4$ alkoxycarbonyl, aryl and het, said $C_1$–$C_4$ alkyl being optionally substituted by halo, hydroxy, $C_1$–$C_4$ alkoxy, halo($C_1$–$C_4$)alkoxy, $C_3$–$C_7$ cycloalkyl($C_1$–$C_4$)alkoxy, —COOH, $C_1$–$C_4$ alkoxycarbonyl, —NR$^3$R$^4$, —SO$_2$(aryl), morpholino, aryl, aryloxy, aryl($C_1$–$C_4$)alkoxy or het; or is pyridin-2-yl, pyridin-3-yl, pyridin-4-yl, pyrimidin-2-yl or pyrimidin-5-yl.

4. A compound as claimed in claim 1 wherein R$^3$R$^4$ and are each independently selected from H and $C_1$–$C_4$ alkyl.

5. A compound as claimed in claim 1 wherein "aryl" means phenyl optionally substituted by 1 or 2 substituents each independently selected from methyl, methoxy, hydroxy, chloro, trifluoromethyl and dimethylamino.

6. A compound as claimed in claim 1 wherein "het" means thienyl, pyrrolyl, pyrazolyl, imidazolyl, triazolyl, thiazolyl, isothiazolyl, oxadiazolyl, thiadiazolyl, pyridinyl, pyridazinyl, pyrimidinyl or pyrazinyl, and optionally substituted by 1 or 2 substituents each independently selected from $C_1$–$C_4$ alkyl, —COOH, —NR$^3$R$^4$ and phenyl, and/or by an oxido substituent on a ring nitrogen heteroatom of said pyridinyl, pyridazinyl, pyrimidinyl or pyrazinyl group.

7. A compound as claimed in claim 1 wherein R is 1,2,3-triazol-4-yl, 1,2,4-triazol-3-yl, 1,2,4-triazol-4-yl or tetrazol-5-yl, each substituted by 1 or 2 substituents each independently selected from:

(I) methyl, ethyl, or propyl, said methyl, ethyl or propyl being optionally substituted by fluoro, hydroxy, methoxy, ethoxy, 2,2,2-trifluoroethoxy, cyclohexylmethoxy, cyclopentylmethoxy, —COOH, methoxycarbonyl, dimethylamino, 4-chlorophenylsulphonyl, morpholino, phenyl, phenoxy, benzyloxy, pyridin-2-yl, pyridin-3-yl or pyridin-4-yl; and (II) allyl, cyclopropyl, cyclohexyl, bromo, hydroxy, ethoxycarbonyl, 2-chlorophenyl, 3-chlorophenyl, 4-chlorophenyl, 4-dimethylaminophenyl, 2-hydroxyphenyl, 2-methoxyphenyl, 3-methoxyphenyl, 4-methoxyphenyl, 2-methylphenyl, phenyl, 4-trifluoromethylphenyl, 2-amino-1,3,4-oxadiazol-5-yl, 2-carboxypyridin-5-yl 1,5-dimethyl-1H-pyrazol-3-yl, 1H-imidazol-1-yl, 1-methylimidazol-2-yl, 1-methylimidazol-4-yl, 1-methylimidazol-5-yl, 3-methylisothiazol-4-yl, 4-methyl-1H-imidazol-5-yl, 3-methyl-1,2,4-oxadiazol-5-yl, 1-methyl-1H-pyrazol-4-yl, 5-methyl-1H-pyrazol-3-yl, 1-methyl-1H-pyrazol-5-yl, 1-oxidopyridin-3-yl, 2-methylpyridin-3-yl, 2-methylpyridin-5-yl, 1-phenylimidazol-4-yl, 5-phenylpyridin-3-yl, 2-phenylpyridin-5-yl, 1-methylpyrrol-2-yl, 4-methyl-1,2,3-thiadiazol-5-yl, 2-methylthiazol-4-yl, 1-methyl-1H-1,2,4-triazol-5-yl, 3-(prop-1-yl)-1H-pyrazol-5-yl, pyrazin-2-yl, 1H-pyrazol-4-yl, pyridazin-4-yl, pyridin-2-yl, pyridin-3-yl, pyridin-4-yl, pyrimidin-2-yl, thien-2-yl, 1H-1,2,4-triazol-5-yl, 1H-1,2,3-triazol-5-yl, quinolin-3-yl or quinolin-6-yl.

8. A compound as claimed in claim 1 wherein R is
1-(2-hydroxyethyl)-5-1,2,3-triazol-4-yl,
1-(2-hydroxyethyl)-4-1,2,3-triazol-5-yl,
2-(2-hydroxyethyl)-5-1,2,3-triazol-4-yl,
1-methyl-5-phenyl-1,2,3-triazol-4-yl,
1-methyl-4-phenyl-1,2,3-triazol-5-yl,
2-methyl-5-phenyl-1,2,3-triazol-4-yl,
5-phenyl-1H-1,2,3-triazol-4-yl,
1-methyl-1H-1,2,4-triazol-3-yl,
2-methyl-2H-1,2,4-triazol-3-yl,
4-(2-hydroxyethyl)-4H-1,2,4-triazol-3-yl,
4-methyl-4H-1,2,4-triazol-3-yl,
3-(2-amino-1,3,4-oxadiazol-5-yl)-5-methyl-4H-1,2,4-triazol-4-yl,
3-benzyl-5-(pyridin-3-yl)-4H-1,2,4-triazol-4-yl,
3-benzyloxymethyl-5-(pyridin-3-yl)-4H-1,2,4-triazol-4-yl,
3-bromo-5-(pyridin-3-yl)-4H-1,2,4-triazol-4-yl,
3-(3-carboxyprop-1-yl)-5-(pyridin-3-yl)-4H-1,2,4-triazol-4-yl,
3-(2-carboxypyridin-5-yl)-5-methoxymethyl-4H-1,2,4-triazol-4-yl,
3-(2-chlorophenyl)-5-methoxymethyl-4H-1,2,4-triazol-4-yl,
3-(2-chlorophenyl)-5-methyl-4H-1,2,4-triazol-4-yl,
3-(3-chlorophenyl)-5-methyl-4H-1,2,4-triazol-4-yl,
3-(4-chlorophenyl)-5-methyl-4H-1,2,4-triazol-4-yl,
3-(4-chlorophenylsulphonylmethyl)-5-methyl-4H-1,2,4-triazol-4-yl,
3-cyclohexylmethoxymethyl-5-(pyridin-3-yl)-4H-1,2,4-triazol-4-yl,
3-cyclopentylmethoxymethyl-5-(pyridin-3-yl)-4H-1,2,4-triazol-4-yl,
3-cyclopropyl-5-methyl-4H-1,2,4--triazol-4-yl,
3,5-di(methoxymethyl)-4H-1,2,4-triazol-4-yl,
3-(N,N-dimethylaminomethyl)-5-ethyl-4H-1,2,4-triazol-4-yl,
3-(N,N-dimethylaminomethyl)-5-(pyridin-3-yl)-4H-1,2,4-triazol-4-yl,
3-(4-dimethylaminophenyl)-5-methyl-4H-1,2,4-triazol-4-yl,
3-(1,5-dimethyl-1 H-pyrazol-3-yl)-5-methoxymethyl-4H-1,2,4-triazol-4-yl,
3-(1,5-dimethyl-1 H-pyrazol-3-yl)-5-methyl-4H-1,2,4-triazol-4-yl,
3,5-dimethyl-4H-1,2,4-triazol-4-yl,
3,5-diphenyl-4H-1,2,4-triazol-4-yl,
3-(2-ethoxyethyl)-5-(pyridin-3-yl)-4H-1,2,4-triazol-4-yl,
3-ethoxymethyl-5-(pyridin-3-yl)-4H-1,2,4-triazol-4-yl,
3-ethoxycarbonyl-4H-1,2,4-triazol-4-yl,
3-ethyl-5-(2-chlorophenyl)-4H-1,2,4-triazol-4-yl,
3-ethyl-5-(2-methoxyphenyl)-4H-1,2,4-triazol-4-yl,
3-ethyl-5-(1-methylpyrazol-5-yl)-4H-1,2,4-triazol-4-yl,
3-ethyl-5-methyl-4H-1,2,4-triazol-4-yl,
3-ethyl-5-morpholinomethyl-4H-1,2,4-triazol-4-yl,
3-ethyl-5-(pyridin-3-yl)-4H-1,2,4-triazol-4-yl,
3-ethyl-4H-1,2,4-triazol-4-yl,
3-(2-hydroxyethyl)-5-methyl-4H-1,2,4-triazol-4-yl,
3-hydroxymethyl-5-methyl-4H-1,2,4-triazol-4-yl,
3-hydroxymethyl-5-phenyl-4H-1,2,4-triazol-4-yl,
3-hydroxymethyl-5-(pyridin-3-yl)-4H-1,2,4-triazol-4-yl,
3-hydroxymethyl-4H-1,2,4-triazol-4-yl,
3-hydroxy-5-methyl-4H-1,2,4-triazol-4-yl,
3-(2-hydroxyphenyl)-5-methyl-4H-1,2,4-triazol-4-yl,
3-(1H-imidazol-1-yl)-5-methyl-4H-1,2,4-triazol-4-yl,
3-(2-methoxyethyl)-5-(pyridin-3-yl)-4H-1,2,4-triazol-4-yl, 3-methoxymethyl-5-(1-methyl-1H-pyrazol-5-yl)-4H-1,2,4-triazol-4-yl,
3-methoxymethyl-5-(2-methylpyridin-5-yl)-4H-1,2,4-triazol-4-yl,
3-methoxymethyl-5-(1-oxidopyridin-3-yl)-4H-1,2,4-triazol-4-yl,
3-methoxymethyl-5-(2-methylthiazol-4-yl)-4H-1,2,4-triazol-4-yl,
3-methoxymethyl-5-(1-phenylimidazol-4-yl)-4H-1,2,4-triazol-4-yl,
3-methoxymethyl-5-(5-phenylpyridin-3-yl)-4H-1,2,4-triazol-4-yl,
3-methoxymethyl-5-(2-phenylpyridin-5-yl)-4H-1,2,4-triazol-4-yl,
3-methoxymethyl-5-(pyridin-3-yl)-4H-1,2,4-triazol-4-yl,
3-methoxymethyl-5-(pyridin-3-yl-methyl)-4H-1,2,4-triazol-4-yl,
3-methoxymethyl-5-(quinolin-3-yl)-4H-1,2,4-triazol-4-yl,
3-methoxymethyl-5-(quinolin-6-yl)-4H-1,2,4-triazol-4-yl,
3-(2-methoxyphenyl)-5-methyl-4H-1,2,4-triazol-4-yl,
3-(3-methoxyphenyl)-5-methyl-4H-1,2,4-triazol-4-yl,
3-(4-methoxyphenyl)-5-methyl-4H-1,2,4-triazol-4-yl,
3-methyl-5-(1-methylimidazol-2-yl)-4H-1,2,4-triazol-4-yl,
3-methyl-5-(1-methylimidazol-4-yl)-4H-1,2,4-triazol-4-yl,
3-methyl-5-(1-methylimidazol-5-yl)-4H-1,2,4-triazol-4-yl,
3-(3-methylisothiazol-4-yl)-5-methyl-4H-1,2,4-triazol-4-yl,
3-methyl-5-(4-methyl-1H-imidazol-5-yl)-4H-1,2,4-triazol-4-yl,
3-methyl-5-(3-methyl-1,2,4-oxadiazol-5-yl)-4H-1,2,4-triazol-4-yl,
3-methyl-5-(2-methylpyridin-3-yl)-4H-1,2,4-triazol-4-yl,
3-methyl-5-(2-methylpyridin-5-yl)-4H-1,2,4-triazol-4-yl,
3-methyl-5-(1-methylpyrazol-5-yl)-4H-1,2,4-triazol-4-yl,
3-methyl-5-(5-methyl-1H-pyrazol-3-yl)-4H-1,2,4-triazol-4-yl,
3-methyl-5-(2-methylphenyl)-4H-1,2,4-triazol-4-yl,
3-methyl-5-(1-methylpyrrol-2-yl)-4H-1,2,4-triazol-4-yl,
3-methyl-5-(4-methyl-1,2,3-thiadiazol-5-yl)-4H-1,2,4-triazol-4-yl,
3-methyl-5-(2-methylthiazol-4-yl)-4H-1,2,4-triazol-4-yl,
3-methyl-5-(1-methyl-1H-1,2,4-triazol-5-yl)-4H-1,2,4-triazol-4-yl,
3-methyl-5-(1-methyl-1H-pyrazol-4-yl)-4H-1,2,4-triazol-4-yl,
3-(3-methyl-1,2,4-oxadiazol-5-yl)-5-(pyridin-3-yl)-4H-1,2,4-triazol-4-yl,
3-methyl-5-phenyl-4H-1,2,4-triazol-4-yl,
3-methyl-5-(3-[prop-1-yl]-1H-pyrazol-5-yl)-4H-1,2,4-triazol-4-yl,
3-methyl-5(pyrazin-2-yl)-4H-1,2,4-triazol-4-yl,
3-methyl-5-(1H-pyrazol-4-yl)-4H-1,2,4-triazol-4-yl,
3-methyl-5-(pyridin-2-yl)-4H-1,2,4-triazol-4-yl,
3-methyl-5-(pyridin-3-yl)-4H-1,2,4-triazol-4-yl,
3-methyl-5-(pyridin-4-yl)-4H-1,2,4-triazol-4-yl,
3-methyl-5-(pyridin-2-ylmethyl)-4H-1,2,4-triazol-4-yl,
3-methyl-5-(pyridin-3-ylmethyl)-4H-1,2,4-triazol-4-yl,
3-methyl-5-(pyridin-4-ylmethyl)-4H-1,2,4-triazol-4-yl,
3-methyl-5-(pyridin-4-yl)-4H-1,2,4-triazol-4-yl,
3-methyl-5-(pyridin-2-yl)-4H-1,2,4-triazol-4-yl,
3-methyl-5-(thien-2-yl)-4H-1,2,4-triazol-4-yl,
3-methyl-4H-1,2,4-triazol-4-yl,
3-methyl-5-(1H-1,2,3-triazol-5-yl)-4H-1,2,4-triazol-4-yl,
3-methyl-5-(1H-1,2,4-triazol-5-yl)-4H-1,2,4-triazol-4-yl,
3-morpholinomethyl-5-(pyridin-3-yl)-4H-1,2,4-triazol-4-yl,
3-phenoxymethyl-5-(pyridin-3-yl)-4H-1,2,4-triazol-4-yl,
3-(2-phenylethyl)-5-(pyridin-3-yl)-4H-1,2,4-triazol-4-yl,
3-(pyridin-3-yl)-5-(2,2,2-trifluoroethoxy)methyl-4H-1,2,4-triazol-4-yl,
3-(pyridin-3-yl)-4H-1,2,4-triazol-4-yl,
3-methyl-5-(4-trifluoromethylphenyl)-4H-1,2,4-triazol-4-yl,
1-allyltetrazol-5-yl,
1-benzyltetrazol-5-yl,
1-carboxymethyltetrazol-5-yl,
1-cyclohexyltetrazol-5-yl,
1-ethyltetrazol-5-yl,
1-(2-hydroxyethyl)tetrazol-5-yl,
1-(3-hydroxypropyl)tetrazol-5-yl,
1-methoxycarbonylmethyltetrazol-5-yl,
1-(2-methoxyethyl)tetrazol-5-yl,
1-methyltetrazol-5-yl,
1-(2-phenylethyl)tetrazol-5-yl,
1-phenyltetrazol-5-yl,
1-(prop-2-yl)tetrazol-5-yl,
1-(2,2,2-trifluoroethyl)tetrazol-5-yl,
pyridin-2-yl,
pyridin-3-yl,
pyridin-4-yl,
pyrimidin-2-yl or
pyrimidin-5-yl.

9. A compound as claimed in claim 1 wherein R is
1-(3-hydroxypropyl)tetrazol-5-yl,
4-methyl-4H-1,2,4-triazol-3-yl,
1-(2-hydroxyethyl)-5-phenyl-1,2,3-triazol-4-yl,
3-methyl-5-(pyridin-3-yl)-4H-1,2,4-triazol-4-yl,
3-methyl-5-(pyridin-3-ylmethyl)-4H-1,2,4-triazol-4-yl,
3-methoxymethyl-5-(pyridin-3-yl)-4H-1,2,4-triazol-4-yl,
3-methoxymethyl-5-(quinolin-3-yl)-4H-1,2,4-triazol-4-yl,
3-methoxymethyl-5-(quinolin-6-yl)-4H-1,2,4-triazol-4-yl
or
3-(1,5-dimethyl-) H-pyrazol-3-yl)-5-methyl-4H-1,2,4-triazol-4-yl.

10. A compound as claimed in claim 1 wherein $R^1$ and $R^2$ are each independently selected from chloro and $C_1$–$C_4$ alkyl.

11. A compound as claimed in claim 1 wherein $R^1$ and $R^2$ are each chloro.

12. A compound as claimed in claim 1 wherein
(i) R is 1-(3-hydroxypropyl)tetrazol-5-yl, $R^1$ is chloro and $R^2$ is chloro;
(ii) R is 4-methyl-4H-1,2,4-triazol-3-yl, $R^1$ is chloro and $R^2$ is chloro;

(iii) R is 1-(2-hydroxyethyl)-5-phenyl-1,2,3-triazol-4-yl, $R^1$ is chloro and $R^2$ chloro;

(iv) R is 3-methyl-5-(pyridin-3-yl)-4H-1,2,4-triazol-4-yl, $R^1$ is chloro and $R^2$ is chloro;

(v) R is 3-methyl-5-(pyridin-3-ylmethyl)-4H-1,2,4-triazol-4-yl, $R^1$ is chloro and $R^2$ is chloro;

(vi) R is 3-methoxymethyl-5-(pyridin-3-yl)-4H-1,2,4-triazol-4-yl, $R^1$ is chloro and $R^2$ is chloro;

(vii) R is 3-(1,5-dimethyl-1H-pyrazol-3-yl)-5-methyl-4H-1,2,4-triazol-4-yl, $R^1$ is chloro and $R^2$ is chloro;

(viii) R is 3-methoxymethyl-5-(pyridin-3-yl)-4H-1,2,4-triazol-4-yl, $R^1$ is chloro and $R^2$ is methyl;

(ix) R is 3-methoxymethyl-5-(pyridin-3-yl)-4H-1,2,4-triazol-4-yl, $R^1$ is methyl and $R^2$ is chloro;

(x) R is 3-methoxymethyl-5-(quinolin-3-yl)-4H-1,2,4-triazol-4-yl, $R^1$ is chloro and $R^2$ is chloro; or (xi) R is 3-methoxymethyl-5-(quinolin-6-yl)-4H-1,2,4-triazol-4-yl, $R^1$ is chloro and $R^2$ is chloro;

or an individual stereoisomer or a pharmaceutically acceptable salt of any thereof.

13. A compound as claimed in claim 1 which is

R-(−)-6,7-dichloro-5-[3-methoxymethyl-5-(3-pyridyl)-4H-1,2,4-triazol-4-yl]-2,3(1H,4H)-quinoxalnedione or a pharmaceutically acceptable salt thereof.

14. A compound as claimed in claim 1 which is

R-(−)-6,7-dichloro-5-[3-methoxymethyl-5-(3-pyridyl)-4H-1,2,4-triazol-4-yl]-2,3(1H,4H)-quinoxalinedione sodium salt.

15. A pharmaceutical composition comprising an amount of a compound of the formula (I) or a pharmaceutically acceptable salt thereof, as claimed in claim 1 together with a pharmaceutically diluent or carrier.

16. A method of treatment of a mammal to treat stroke, transient ischaemic attack, peri-operative ischaemia or traumatic head injury which comprises treating said mammal with an effective amount of a compound of the formula (1), or with a pharmaceutically acceptable salt as claimed in claim 1.

* * * * *